United States Patent
Mahr et al.

(10) Patent No.: US 10,654,904 B2
(45) Date of Patent: May 19, 2020

(54) PEPTIDES AND COMBINATION OF PEPTIDES FOR USE IN IMMUNOTHERAPY AGAINST SMALL CELL LUNG CANCER AND OTHER CANCERS

(71) Applicant: Immatics Biotechnologies GmbH, Tuebingen (DE)

(72) Inventors: Andrea Mahr, Tuebingen (DE); Toni Weinschenk, Aichwald (DE); Valentina Goldfinger, Tuebingen (DE); Oliver Schoor, Tuebingen (DE); Jens Fritsche, Dusslingen (DE); Harpreet Singh, Munich (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/591,323

(22) Filed: Oct. 2, 2019

(65) Prior Publication Data
US 2020/0048320 A1   Feb. 13, 2020

Related U.S. Application Data

(63) Continuation of application No. 16/237,279, filed on Dec. 31, 2018, now Pat. No. 10,487,126, which is a continuation of application No. 15/281,537, filed on Sep. 30, 2016, now Pat. No. 10,253,077.

(60) Provisional application No. 62/237,091, filed on Oct. 5, 2015.

(30) Foreign Application Priority Data

Oct. 5, 2015 (GB) .................................. 1517538.3

(51) Int. Cl.
| | |
|---|---|
| C07K 14/47 | (2006.01) |
| C07K 14/74 | (2006.01) |
| A61K 39/00 | (2006.01) |
| C07K 16/28 | (2006.01) |
| C07K 16/30 | (2006.01) |
| C07K 14/725 | (2006.01) |
| C12N 5/0783 | (2010.01) |
| G01N 33/574 | (2006.01) |
| C07K 7/06 | (2006.01) |
| C12N 15/115 | (2010.01) |
| C12N 15/62 | (2006.01) |

(52) U.S. Cl.
CPC ...... *C07K 14/4748* (2013.01); *A61K 39/0011* (2013.01); *C07K 7/06* (2013.01); *C07K 14/7051* (2013.01); *C07K 14/70539* (2013.01); *C07K 16/2833* (2013.01); *C07K 16/30* (2013.01); *C12N 5/0636* (2013.01); *C12N 15/115* (2013.01); *C12N 15/62* (2013.01); *G01N 33/57423* (2013.01); *A61K 2039/5158* (2013.01); *C07K 2319/40* (2013.01); *C12N 2310/16* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 9,023,803 B2 | 5/2015 | Singh et al. | |
| 9,056,069 B2 | 6/2015 | Singh et al. | |
| 9,943,579 B2 | 4/2018 | Weinschenk et al. | |
| 10,071,148 B2 | 9/2018 | Weinschenk et al. | |
| 2006/0045881 A1* | 3/2006 | Molldrem .......... | A61K 39/0011 424/178.1 |
| 2008/0207497 A1 | 8/2008 | Ramakrishna et al. | |
| 2009/0274714 A1 | 11/2009 | Singh et al. | |
| 2013/0095128 A1 | 4/2013 | Nakamura et al. | |
| 2013/0096016 A1 | 4/2013 | Weinschenk et al. | |
| 2016/0168200 A1 | 6/2016 | Weinschenk et al. | |

FOREIGN PATENT DOCUMENTS

| | | |
|---|---|---|
| EP | 1760089 A1 | 3/2007 |
| WO | 2011151403 A1 | 12/2011 |
| WO | 2015/018805 A1 | 2/2015 |

OTHER PUBLICATIONS

Great Britain Search Report dated Jul. 6, 2016 issued in counterpart GB Application No. 1517538.3.
Walter et al., "Multipeptide immune response to cancer vaccine IMA901 after single-dose cyclophosphamide associates with longer patient survival" Nature Medicine. (Aug. 2012) vol. 18, No. 8: 1254-1266.

(Continued)

*Primary Examiner* — Peter J Reddig
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

30 Claims, 23 Drawing Sheets

Specification includes a Sequence Listing.

(56) References Cited

OTHER PUBLICATIONS

E. Milner et al. The Effect of Proteasome Inhibition on the Generation of the Human Leukocyte Antigen (HLA) Peptidome. Molecular & Cellular Proteomics. vol. 12, No. 7. Mar. 28, 2013. pp. 1853-1864. DOI: 10.1074/mcp.M112.026013, and Supplemental Table 4.
Steffen Walter et al. "Multipeptide immune response to cancer vaccine IMA901 after single-dose cyclophosphamide associates with longer patient survival." Nature Medicine. vol. 18, No. 8. Jul. 29, 2012. pp. 1254-1261. DOI: 10.1038/nm.2883.
International Search Report for PCT/EP2016/073416, dated Jan. 3, 2017.
Dudley and Rosenberg (Nature Reviews Cancer 2003 3:666-675) (Year: 2003).
Marincola et al. (Trends in Immunology, Jun. 2003, 334-341) (Year: 2003).
Gura (Science, 1997, 278: 1041-1042) (Year: 1997).
Kaiser (Science 2006, 31: 1370) (Year: 2006).
Janeway CA Jr, Travers P, Walport M, et al. (Immunobiology: The Immune System in Health and Disease. 5th edition. New York: Garland Science; 2001. Antigen recognition by T cells. Available from: https://www.ncbi.nlm.nih.gov/books/NBK27098/) (Year: 2001).

\* cited by examiner

Peptide: AMLEEVNYI (A*02)
SEQ ID NO: 1

Peptide: VLAEIDPKQLV (A*02)
SEQ ID NO: 3

Figure 1C
Peptide: GLDPTQFRV (A*02)
SEQ ID NO: 39

19 SCLC cancer tissues 257 normal tissues
2 adipose tissues, 3 adrenal glands, 4 blood cells, 10 blood vessels, 6 bone marrows, 7 brains, 6 breasts, 2 cartilages, 1 eye, 3 gallbladders, 5 hearts, 14 kidneys, 19 large intestines, 20 livers, 45 lungs, 4 lymph nodes, 7 nerves, 3 ovaries, 10 pancreases, 1 peritoneum, 5 pituitary glands, 6 placentas, 3 pleuras, 3 prostates, 7 salivary glands, 5 skeletal muscles, 6 skins, 3 small intestines, 4 spleens, 5 stomachs, 6 testis, 3 thymi, 3 thyroid glands, 9 tracheas, 3 ureters, 6 urinary bladders, 2 uteri, 6 esophagi Relative Presentation [Arbitrary Units]

Peptide: GLLEVQVEV (A*02)
SEQ ID NO: 40

Peptide: SLQSLIISV (A*02)
SEQ ID NO: 5

Peptide: GLLGDIAIHL (A*02)
SEQ ID NO: 7

Peptide detected on
1 cell line (blood cells), 2 normal tissues (1 brain, 1 pituitary gland), 35 cancer tissues (27 brain cancers, 1 breast cancer, 1 liver cancer, 4 lung cancers, 2 uterus cancers) (from left to right)

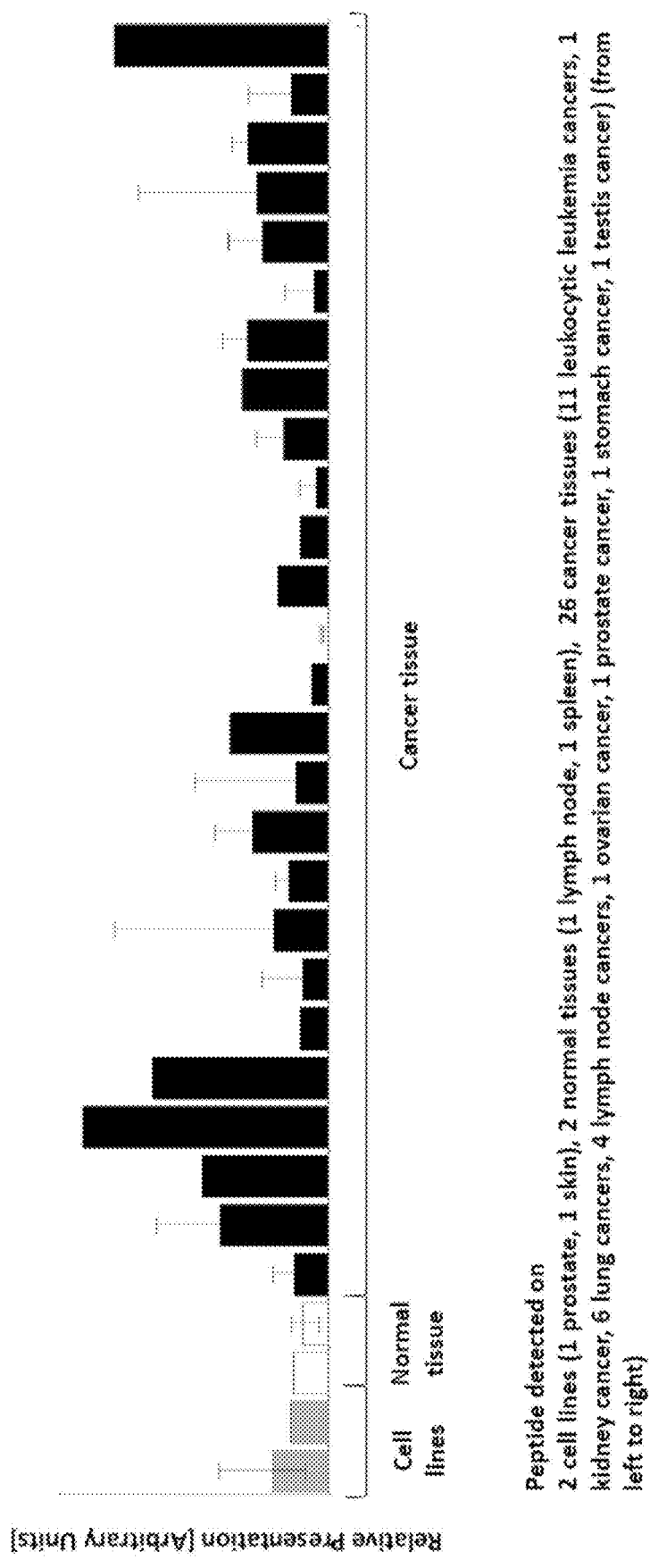

Peptide: GLYSKTSQSV (A*02)
SEQ ID NO: 33

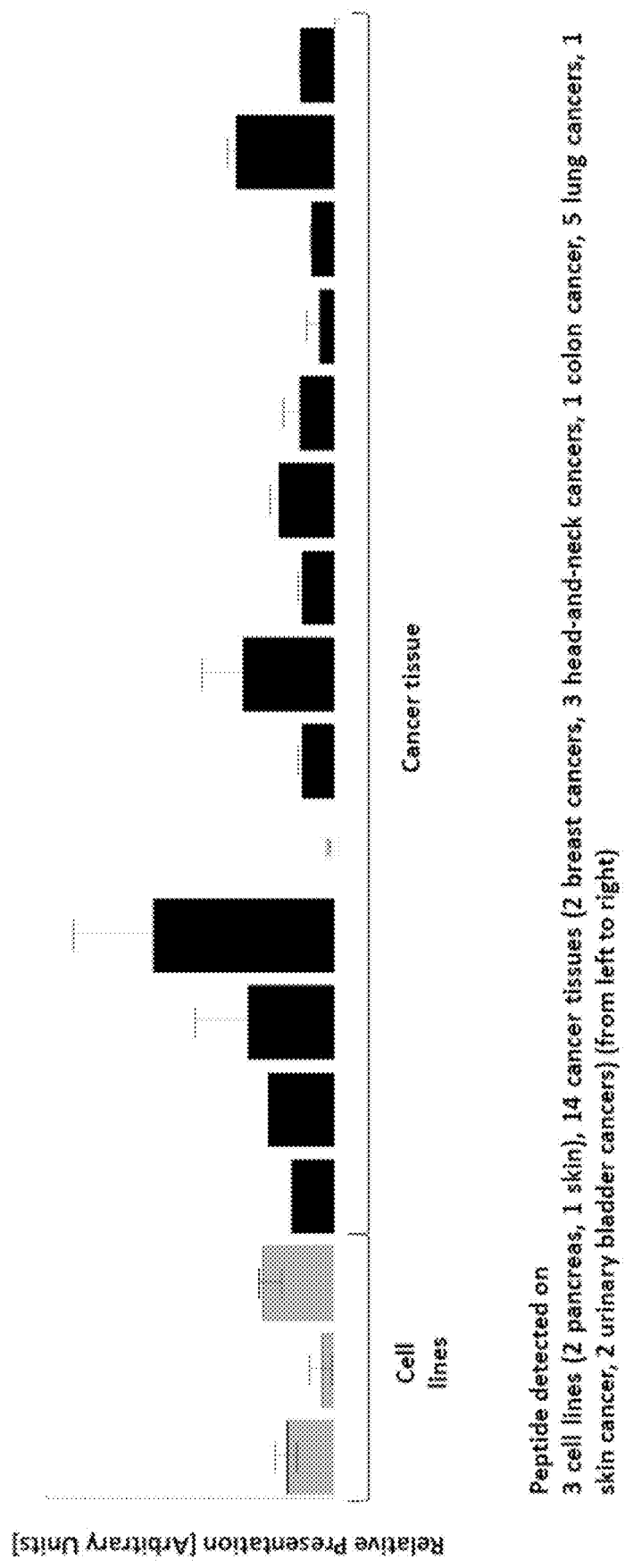

Peptide: VLLSGLTEV (A*02)
SEQ ID NO: 59

Peptide: KAIGSLKEV (A*02)
SEQ ID NO: 72

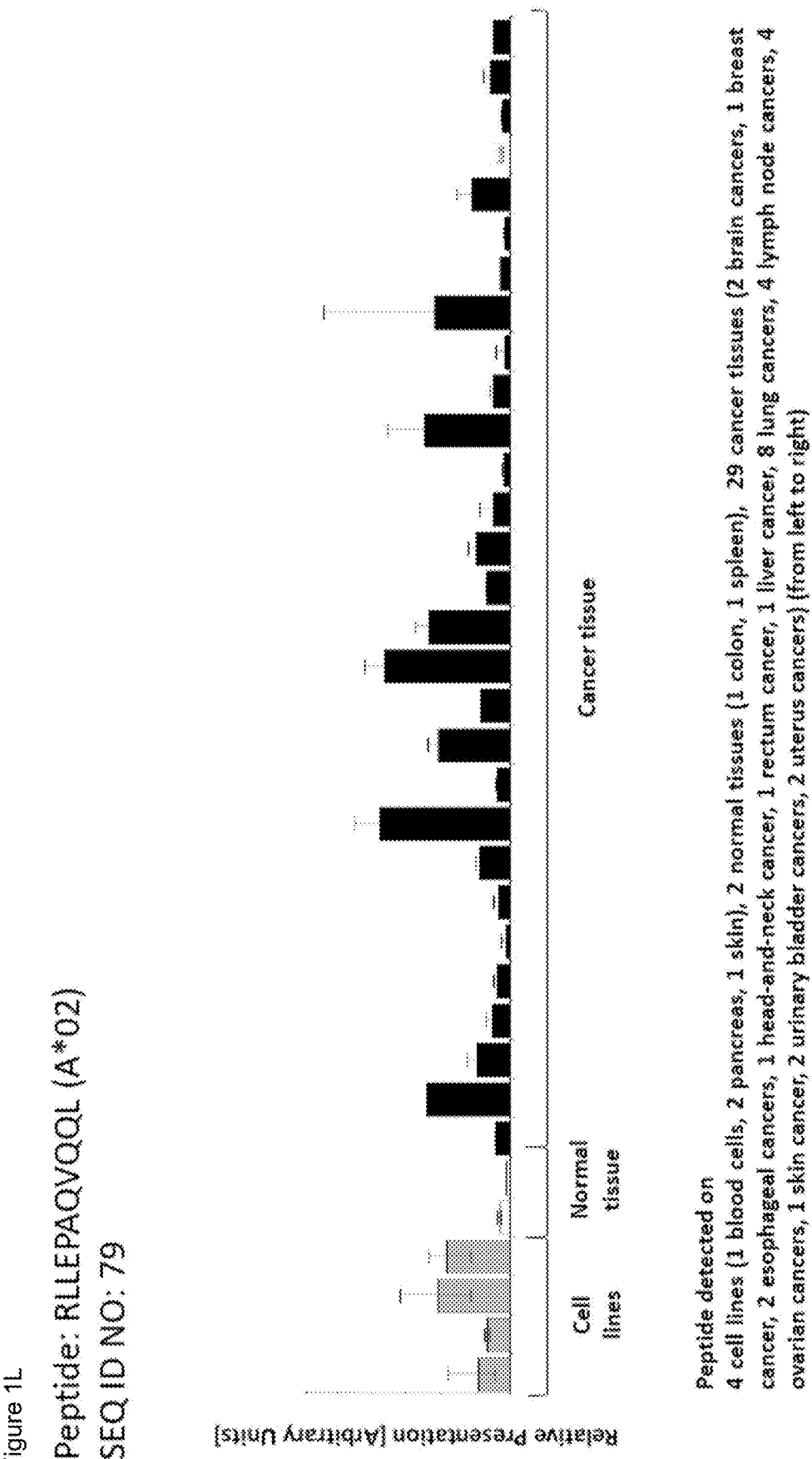

Peptide: LLAEIGAVTLV (A*02)
SEQ ID NO: 81

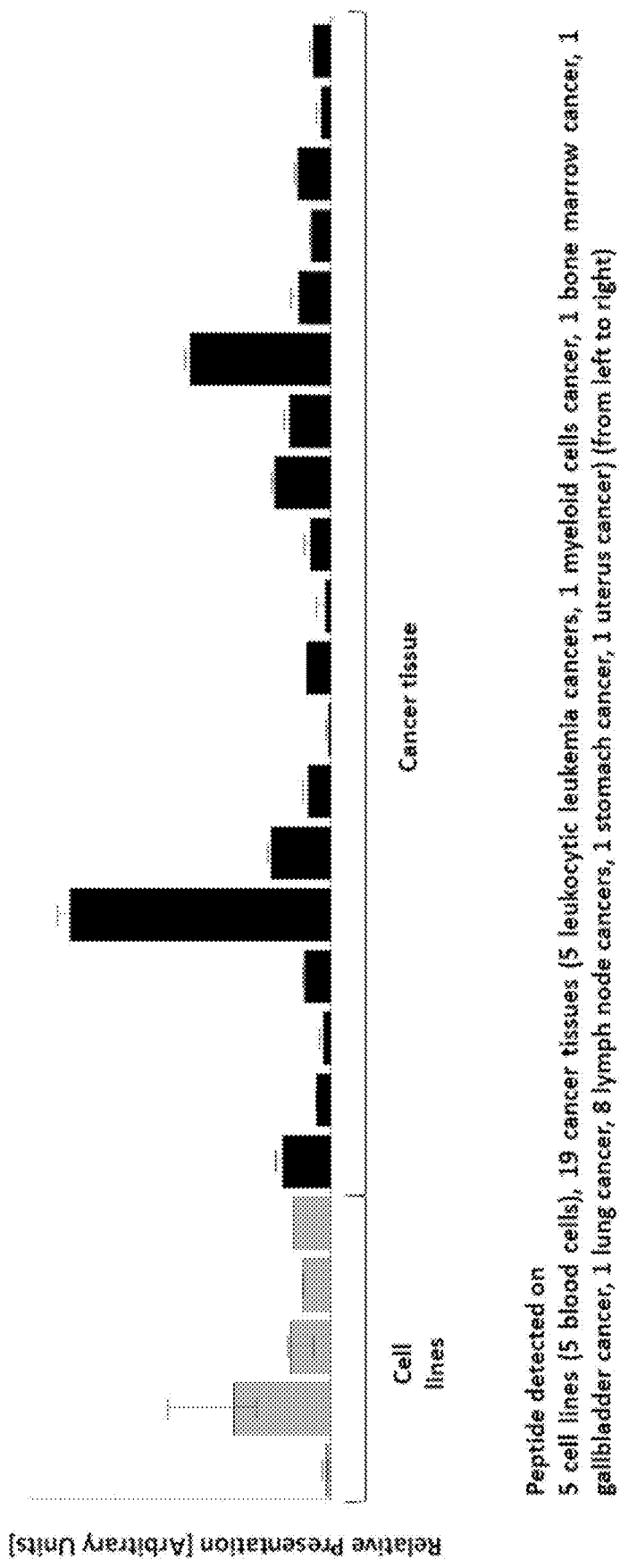

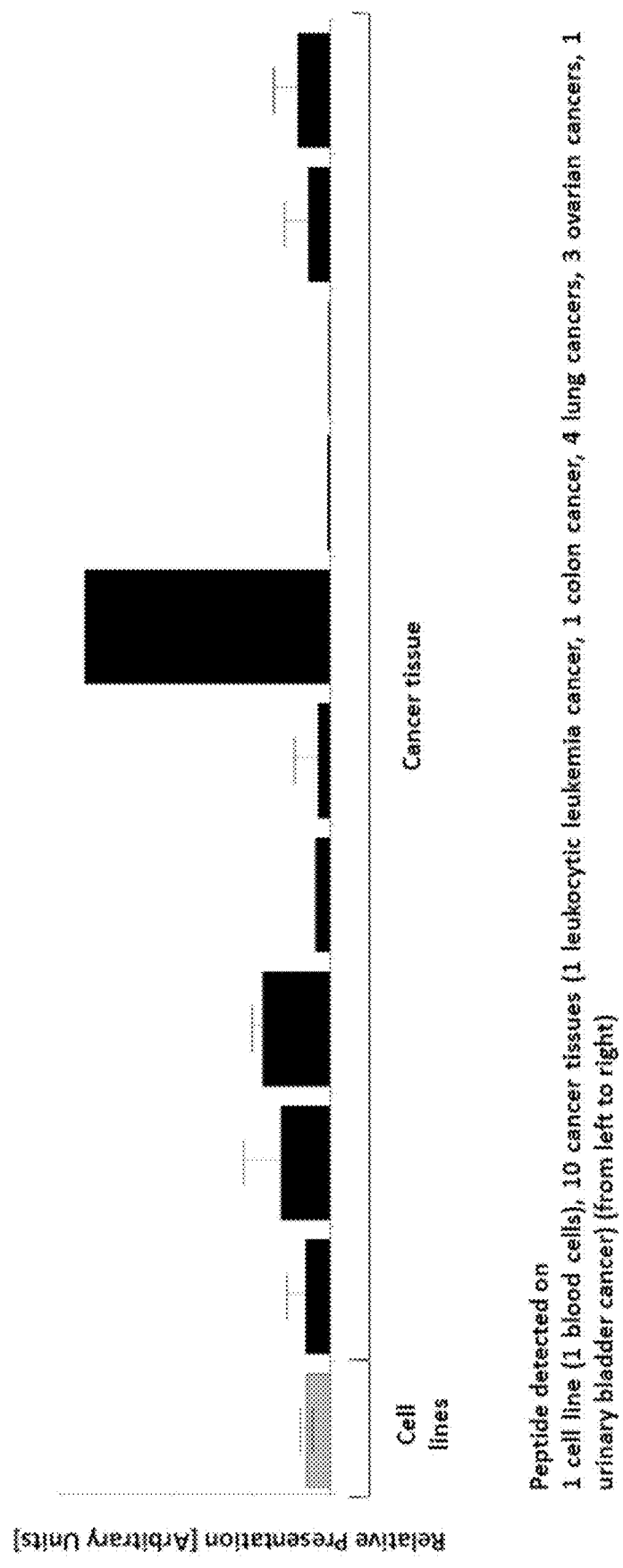

Peptide: SLIDDNNEINL (A*02)
SEQ ID NO: 119

Gene: MEX3A
Peptide: GLLEDERALQL
SEQ ID NO: 42

Gene: ECT2
Peptide: KAIGSLKEV
SEQ ID NO: 72

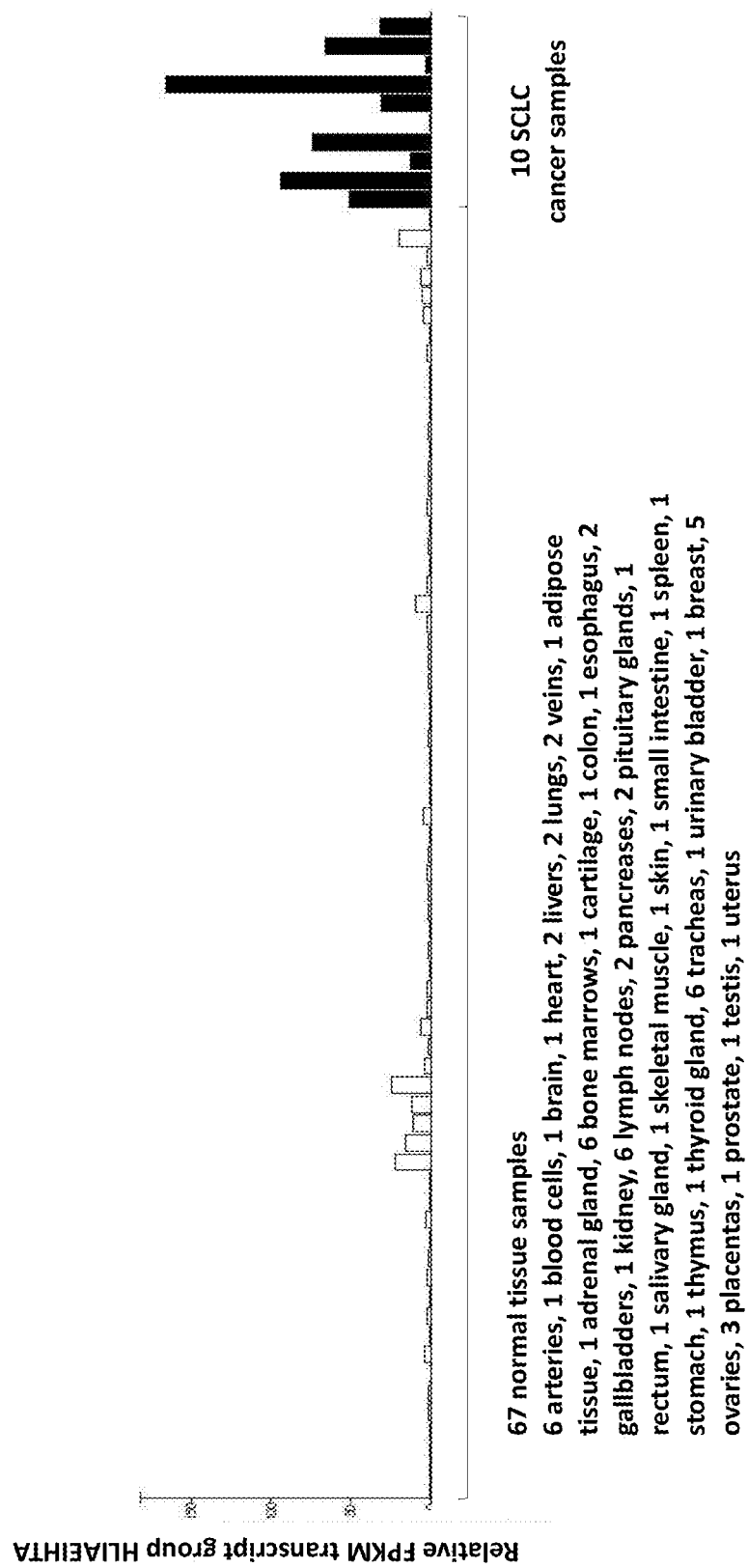

Gene: TIMELESS
Peptide: KAYQELLATV
SEQ ID NO: 41

SEQUENCE LISTING

```
<160> NUMBER OF SEQ ID NOS: 144

<210> SEQ ID NO 1
<211> LENGTH: 9
<212> TYPE: PRT
<213> ORGANISM: Homo sapiens

<400> SEQUENCE: 1

Ala Met Leu Glu Glu Val Asn Tyr Ile
1               5

<210> SEQ ID NO 2
<211> LENGTH: 11
<212> TYPE: PRT
<213> ORGANISM: Homo sapiens

<400> SEQUENCE: 2

Val Met Phe Asn Phe Pro Asp Gln Ala Thr Val
1               5                   10

<210> SEQ ID NO 3
<211> LENGTH: 11
<212> TYPE: PRT
<213> ORGANISM: Homo sapiens

<400> SEQUENCE: 3
```

```
Val Leu Ala Glu Ile Asp Pro Lys Gln Leu Val
1               5                   10
```

<210> SEQ ID NO 4
<211> LENGTH: 11
<212> TYPE: PRT
<213> ORGANISM: Homo sapiens

<400> SEQUENCE: 4

```
Gly Leu Leu Asp Pro Gly Met Leu Val Asn Ile
1               5                   10
```

<210> SEQ ID NO 5
<211> LENGTH: 9
<212> TYPE: PRT
<213> ORGANISM: Homo sapiens

<400> SEQUENCE: 5

```
Ser Leu Gln Ser Leu Ile Ile Ser Val
1               5
```

<210> SEQ ID NO 6
<211> LENGTH: 9
<212> TYPE: PRT
<213> ORGANISM: Homo sapiens

<400> SEQUENCE: 6

```
Ser Ile Met Asp Tyr Val Val Phe Val
1               5
```

<210> SEQ ID NO 7
<211> LENGTH: 10
<212> TYPE: PRT
<213> ORGANISM: Homo sapiens

<400> SEQUENCE: 7

```
Gly Leu Leu Gly Asp Ile Ala Ile His Leu
1               5                   10
```

<210> SEQ ID NO 8
<211> LENGTH: 12
<212> TYPE: PRT
<213> ORGANISM: Homo sapiens

<400> SEQUENCE: 8

```
Val Leu Ile Asp Asp Ser Gln Ser Ile Ile Phe Ile
1               5                   10
```

<210> SEQ ID NO 9
<211> LENGTH: 11
<212> TYPE: PRT
<213> ORGANISM: Homo sapiens

<400> SEQUENCE: 9

```
Ala Ala Ala Pro Gly Glu Ala Leu His Thr Ala
1               5                   10
```

<210> SEQ ID NO 10
<211> LENGTH: 9
<212> TYPE: PRT
<213> ORGANISM: Homo sapiens

<400> SEQUENCE: 10

```
Ile Leu Ala Ala Gly Phe Asp Gly Met
1               5
```

<210> SEQ ID NO 11
<211> LENGTH: 9
<212> TYPE: PRT
<213> ORGANISM: Homo sapiens

<400> SEQUENCE: 11

Lys Leu Phe Ala Ile Pro Ile Leu Leu
1               5

<210> SEQ ID NO 12
<211> LENGTH: 11
<212> TYPE: PRT
<213> ORGANISM: Homo sapiens

<400> SEQUENCE: 12

Met Leu Phe Glu Gly Leu Asp Leu Val Ser Ala
1               5                   10

<210> SEQ ID NO 13
<211> LENGTH: 9
<212> TYPE: PRT
<213> ORGANISM: Homo sapiens

<400> SEQUENCE: 13

Phe Leu Thr Ala Phe Leu Val Gln Ile
1               5

<210> SEQ ID NO 14
<211> LENGTH: 9
<212> TYPE: PRT
<213> ORGANISM: Homo sapiens

<400> SEQUENCE: 14

Ile Leu Ile Glu Thr Lys Leu Val Leu
1               5

<210> SEQ ID NO 15
<211> LENGTH: 9
<212> TYPE: PRT
<213> ORGANISM: Homo sapiens

<400> SEQUENCE: 15

Ser Leu Leu Thr Ala Ile Ser Glu Val
1               5

<210> SEQ ID NO 16
<211> LENGTH: 9
<212> TYPE: PRT
<213> ORGANISM: Homo sapiens

<400> SEQUENCE: 16

Val Ile Leu Asp Leu Pro Leu Val Ile
1               5

<210> SEQ ID NO 17
<211> LENGTH: 9
<212> TYPE: PRT
<213> ORGANISM: Homo sapiens

<400> SEQUENCE: 17

Ser Leu Met Leu Val Thr Val Glu Leu
1               5

<210> SEQ ID NO 18
<211> LENGTH: 9
<212> TYPE: PRT
<213> ORGANISM: Homo sapiens

<400> SEQUENCE: 18

Ala Leu Gly Glu Ile Ser Val Ser Val
1               5

<210> SEQ ID NO 19
<211> LENGTH: 9
<212> TYPE: PRT
<213> ORGANISM: Homo sapiens

<400> SEQUENCE: 19

Val Leu Leu Thr Thr Ala Val Glu Val
1               5

<210> SEQ ID NO 20
<211> LENGTH: 9
<212> TYPE: PRT
<213> ORGANISM: Homo sapiens

<400> SEQUENCE: 20

Met Leu Asp Glu Ile Leu Leu Gln Leu
1               5

<210> SEQ ID NO 21
<211> LENGTH: 9
<212> TYPE: PRT
<213> ORGANISM: Homo sapiens

<400> SEQUENCE: 21

Thr Met Glu Glu Met Ile Phe Glu Val
1               5

<210> SEQ ID NO 22
<211> LENGTH: 9
<212> TYPE: PRT
<213> ORGANISM: Homo sapiens

<400> SEQUENCE: 22

Leu Leu Pro Glu Lys Ser Trp Glu Ile
1               5

<210> SEQ ID NO 23
<211> LENGTH: 9
<212> TYPE: PRT
<213> ORGANISM: Homo sapiens

<400> SEQUENCE: 23

Tyr Gln Ile Asp Thr Val Ile Asn Leu
1               5

<210> SEQ ID NO 24
<211> LENGTH: 9
<212> TYPE: PRT
<213> ORGANISM: Homo sapiens

<400> SEQUENCE: 24

Phe Leu Met Glu Glu Val His Met Ile
1               5

<210> SEQ ID NO 25
<211> LENGTH: 9

-continued

<212> TYPE: PRT
<213> ORGANISM: Homo sapiens

<400> SEQUENCE: 25

Gly Leu Ser Glu Thr Ile Leu Ala Val
1               5

<210> SEQ ID NO 26
<211> LENGTH: 10
<212> TYPE: PRT
<213> ORGANISM: Homo sapiens

<400> SEQUENCE: 26

Lys Met Leu Asp Glu Ala Val Phe Gln Val
1               5                   10

<210> SEQ ID NO 27
<211> LENGTH: 9
<212> TYPE: PRT
<213> ORGANISM: Homo sapiens

<400> SEQUENCE: 27

Ser Leu Asp Ile Ile Thr Ile Thr Val
1               5

<210> SEQ ID NO 28
<211> LENGTH: 9
<212> TYPE: PRT
<213> ORGANISM: Homo sapiens

<400> SEQUENCE: 28

Ile Leu Val Ser Gln Leu Glu Gln Leu
1               5

<210> SEQ ID NO 29
<211> LENGTH: 9
<212> TYPE: PRT
<213> ORGANISM: Homo sapiens

<400> SEQUENCE: 29

Asn Leu Ile Ser Gln Leu Thr Thr Val
1               5

<210> SEQ ID NO 30
<211> LENGTH: 9
<212> TYPE: PRT
<213> ORGANISM: Homo sapiens

<400> SEQUENCE: 30

Lys Met Leu Gly Leu Thr Val Ser Leu
1               5

<210> SEQ ID NO 31
<211> LENGTH: 9
<212> TYPE: PRT
<213> ORGANISM: Homo sapiens

<400> SEQUENCE: 31

Arg Leu Leu Gln Asp Pro Val Gly Val
1               5

<210> SEQ ID NO 32
<211> LENGTH: 9
<212> TYPE: PRT
<213> ORGANISM: Homo sapiens

```
<400> SEQUENCE: 32

Ala Leu Thr Ser Leu Glu Leu Glu Leu
1               5

<210> SEQ ID NO 33
<211> LENGTH: 10
<212> TYPE: PRT
<213> ORGANISM: Homo sapiens

<400> SEQUENCE: 33

Gly Leu Tyr Ser Lys Thr Ser Gln Ser Val
1               5                   10

<210> SEQ ID NO 34
<211> LENGTH: 9
<212> TYPE: PRT
<213> ORGANISM: Homo sapiens

<400> SEQUENCE: 34

Leu Val Phe Glu Gly Ile Met Glu Val
1               5

<210> SEQ ID NO 35
<211> LENGTH: 9
<212> TYPE: PRT
<213> ORGANISM: Homo sapiens

<400> SEQUENCE: 35

Phe Met Gly Asp Val Phe Ile Asn Val
1               5

<210> SEQ ID NO 36
<211> LENGTH: 9
<212> TYPE: PRT
<213> ORGANISM: Homo sapiens

<400> SEQUENCE: 36

Arg Met Asp Gly Ala Val Thr Ser Val
1               5

<210> SEQ ID NO 37
<211> LENGTH: 10
<212> TYPE: PRT
<213> ORGANISM: Homo sapiens

<400> SEQUENCE: 37

Ser Leu Phe Tyr Asn Glu Leu His Tyr Val
1               5                   10

<210> SEQ ID NO 38
<211> LENGTH: 9
<212> TYPE: PRT
<213> ORGANISM: Homo sapiens

<400> SEQUENCE: 38

Gly Leu Ile Ser Ser Leu Asn Glu Ile
1               5

<210> SEQ ID NO 39
<211> LENGTH: 9
<212> TYPE: PRT
<213> ORGANISM: Homo sapiens

<400> SEQUENCE: 39
```

Gly Leu Asp Pro Thr Gln Phe Arg Val
1               5

<210> SEQ ID NO 40
<211> LENGTH: 9
<212> TYPE: PRT
<213> ORGANISM: Homo sapiens

<400> SEQUENCE: 40

Gly Leu Leu Glu Val Gln Val Glu Val
1               5

<210> SEQ ID NO 41
<211> LENGTH: 10
<212> TYPE: PRT
<213> ORGANISM: Homo sapiens

<400> SEQUENCE: 41

Lys Ala Tyr Gln Glu Leu Leu Ala Thr Val
1               5                   10

<210> SEQ ID NO 42
<211> LENGTH: 11
<212> TYPE: PRT
<213> ORGANISM: Homo sapiens

<400> SEQUENCE: 42

Gly Leu Leu Glu Asp Glu Arg Ala Leu Gln Leu
1               5                   10

<210> SEQ ID NO 43
<211> LENGTH: 9
<212> TYPE: PRT
<213> ORGANISM: Homo sapiens

<400> SEQUENCE: 43

Tyr Leu Trp Ser Glu Val Phe Ser Met
1               5

<210> SEQ ID NO 44
<211> LENGTH: 9
<212> TYPE: PRT
<213> ORGANISM: Homo sapiens

<400> SEQUENCE: 44

Ala Leu Ile Val Gly Ile Pro Ser Val
1               5

<210> SEQ ID NO 45
<211> LENGTH: 11
<212> TYPE: PRT
<213> ORGANISM: Homo sapiens

<400> SEQUENCE: 45

Ser Leu Ser Gly Glu Ile Ile Leu His Ser Val
1               5                   10

<210> SEQ ID NO 46
<211> LENGTH: 9
<212> TYPE: PRT
<213> ORGANISM: Homo sapiens

<400> SEQUENCE: 46

Ala Leu Trp Val Ala Val Pro Lys Ala

```
<210> SEQ ID NO 47
<211> LENGTH: 9
<212> TYPE: PRT
<213> ORGANISM: Homo sapiens

<400> SEQUENCE: 47

Gly Leu Leu Glu Ala Leu Leu Lys Ile
1               5

<210> SEQ ID NO 48
<211> LENGTH: 10
<212> TYPE: PRT
<213> ORGANISM: Homo sapiens

<400> SEQUENCE: 48

Ser Leu Ile Gly Leu Asp Leu Ser Ser Val
1               5                   10

<210> SEQ ID NO 49
<211> LENGTH: 9
<212> TYPE: PRT
<213> ORGANISM: Homo sapiens

<400> SEQUENCE: 49

Arg Leu Ala Leu Asn Thr Pro Lys Val
1               5

<210> SEQ ID NO 50
<211> LENGTH: 9
<212> TYPE: PRT
<213> ORGANISM: Homo sapiens

<400> SEQUENCE: 50

Phe Leu Leu Ser Gln Ile Val Ala Leu
1               5

<210> SEQ ID NO 51
<211> LENGTH: 11
<212> TYPE: PRT
<213> ORGANISM: Homo sapiens

<400> SEQUENCE: 51

Ile Leu Asp Glu Ala Gly Val Lys Tyr Phe Leu
1               5                   10

<210> SEQ ID NO 52
<211> LENGTH: 10
<212> TYPE: PRT
<213> ORGANISM: Homo sapiens

<400> SEQUENCE: 52

Ile Leu Ala Ser Phe Met Leu Thr Gly Val
1               5                   10

<210> SEQ ID NO 53
<211> LENGTH: 9
<212> TYPE: PRT
<213> ORGANISM: Homo sapiens

<400> SEQUENCE: 53

Leu Leu Ser Glu Glu His Ile Thr Leu
1               5
```

```
<210> SEQ ID NO 54
<211> LENGTH: 10
<212> TYPE: PRT
<213> ORGANISM: Homo sapiens

<400> SEQUENCE: 54

His Leu Phe Asp Ile Ile Leu Thr Ser Val
1               5                   10

<210> SEQ ID NO 55
<211> LENGTH: 9
<212> TYPE: PRT
<213> ORGANISM: Homo sapiens

<400> SEQUENCE: 55

Leu Leu Ile Ala Asp Asn Pro Gln Leu
1               5

<210> SEQ ID NO 56
<211> LENGTH: 12
<212> TYPE: PRT
<213> ORGANISM: Homo sapiens

<400> SEQUENCE: 56

Ser Leu Phe Ser Gln Met Gly Ser Gln Tyr Glu Leu
1               5                   10

<210> SEQ ID NO 57
<211> LENGTH: 10
<212> TYPE: PRT
<213> ORGANISM: Homo sapiens

<400> SEQUENCE: 57

Val Leu Ile Gly Asp Val Leu Val Ala Val
1               5                   10

<210> SEQ ID NO 58
<211> LENGTH: 10
<212> TYPE: PRT
<213> ORGANISM: Homo sapiens

<400> SEQUENCE: 58

Val Leu Leu Asn Ile Asn Gly Ile Asp Leu
1               5                   10

<210> SEQ ID NO 59
<211> LENGTH: 9
<212> TYPE: PRT
<213> ORGANISM: Homo sapiens

<400> SEQUENCE: 59

Val Leu Leu Ser Gly Leu Thr Glu Val
1               5

<210> SEQ ID NO 60
<211> LENGTH: 9
<212> TYPE: PRT
<213> ORGANISM: Homo sapiens

<400> SEQUENCE: 60

Val Val Ser Gly Ala Thr Glu Thr Leu
1               5

<210> SEQ ID NO 61
```

```
<211> LENGTH: 9
<212> TYPE: PRT
<213> ORGANISM: Homo sapiens

<400> SEQUENCE: 61

Tyr Gln Ala Pro Tyr Phe Leu Thr Val
1               5

<210> SEQ ID NO 62
<211> LENGTH: 11
<212> TYPE: PRT
<213> ORGANISM: Homo sapiens

<400> SEQUENCE: 62

Val Met Leu Pro Ile Gly Ala Val Val Met Val
1               5                   10

<210> SEQ ID NO 63
<211> LENGTH: 9
<212> TYPE: PRT
<213> ORGANISM: Homo sapiens

<400> SEQUENCE: 63

Leu Leu Met Ser Thr Glu Asn Glu Leu
1               5

<210> SEQ ID NO 64
<211> LENGTH: 9
<212> TYPE: PRT
<213> ORGANISM: Homo sapiens

<400> SEQUENCE: 64

Val Leu Phe His Gln Leu Gln Glu Ile
1               5

<210> SEQ ID NO 65
<211> LENGTH: 9
<212> TYPE: PRT
<213> ORGANISM: Homo sapiens

<400> SEQUENCE: 65

Val Met Tyr Asp Leu Ile Thr Glu Leu
1               5

<210> SEQ ID NO 66
<211> LENGTH: 9
<212> TYPE: PRT
<213> ORGANISM: Homo sapiens

<400> SEQUENCE: 66

Tyr Leu Asn Leu Ile Ser Thr Ser Val
1               5

<210> SEQ ID NO 67
<211> LENGTH: 9
<212> TYPE: PRT
<213> ORGANISM: Homo sapiens

<400> SEQUENCE: 67

Met Leu Tyr Asp Ile Val Pro Val Val
1               5

<210> SEQ ID NO 68
<211> LENGTH: 9
<212> TYPE: PRT
```

```
<213> ORGANISM: Homo sapiens

<400> SEQUENCE: 68

Phe Leu Phe Pro Val Tyr Pro Leu Ile
1               5

<210> SEQ ID NO 69
<211> LENGTH: 9
<212> TYPE: PRT
<213> ORGANISM: Homo sapiens

<400> SEQUENCE: 69

Lys Leu Phe Asp Arg Ser Val Asp Leu
1               5

<210> SEQ ID NO 70
<211> LENGTH: 9
<212> TYPE: PRT
<213> ORGANISM: Homo sapiens

<400> SEQUENCE: 70

Thr Leu Leu Trp Lys Leu Val Glu Val
1               5

<210> SEQ ID NO 71
<211> LENGTH: 9
<212> TYPE: PRT
<213> ORGANISM: Homo sapiens

<400> SEQUENCE: 71

Phe Ile Phe Glu Gln Val Gln Asn Val
1               5

<210> SEQ ID NO 72
<211> LENGTH: 9
<212> TYPE: PRT
<213> ORGANISM: Homo sapiens

<400> SEQUENCE: 72

Lys Ala Ile Gly Ser Leu Lys Glu Val
1               5

<210> SEQ ID NO 73
<211> LENGTH: 9
<212> TYPE: PRT
<213> ORGANISM: Homo sapiens

<400> SEQUENCE: 73

Ser Leu Ser Ser Tyr Thr Pro Asp Val
1               5

<210> SEQ ID NO 74
<211> LENGTH: 9
<212> TYPE: PRT
<213> ORGANISM: Homo sapiens

<400> SEQUENCE: 74

Phe Leu Asp Ser Leu Ser Pro Ser Val
1               5

<210> SEQ ID NO 75
<211> LENGTH: 9
<212> TYPE: PRT
<213> ORGANISM: Homo sapiens
```

```
<400> SEQUENCE: 75

Ser Leu Asp Leu His Val Pro Ser Leu
1               5

<210> SEQ ID NO 76
<211> LENGTH: 9
<212> TYPE: PRT
<213> ORGANISM: Homo sapiens

<400> SEQUENCE: 76

Val Leu Thr Thr Val Met Ile Thr Val
1               5

<210> SEQ ID NO 77
<211> LENGTH: 10
<212> TYPE: PRT
<213> ORGANISM: Homo sapiens

<400> SEQUENCE: 77

Ala Ile Ile Asp Gly Lys Ile Phe Cys Val
1               5                   10

<210> SEQ ID NO 78
<211> LENGTH: 12
<212> TYPE: PRT
<213> ORGANISM: Homo sapiens

<400> SEQUENCE: 78

Arg Ile Ile Asp Pro Glu Asp Leu Lys Ala Leu Leu
1               5                   10

<210> SEQ ID NO 79
<211> LENGTH: 11
<212> TYPE: PRT
<213> ORGANISM: Homo sapiens

<400> SEQUENCE: 79

Arg Leu Leu Glu Pro Ala Gln Val Gln Gln Leu
1               5                   10

<210> SEQ ID NO 80
<211> LENGTH: 10
<212> TYPE: PRT
<213> ORGANISM: Homo sapiens

<400> SEQUENCE: 80

Ile Leu Met Asp Pro Ser Pro Glu Tyr Ala
1               5                   10

<210> SEQ ID NO 81
<211> LENGTH: 11
<212> TYPE: PRT
<213> ORGANISM: Homo sapiens

<400> SEQUENCE: 81

Leu Leu Ala Glu Ile Gly Ala Val Thr Leu Val
1               5                   10

<210> SEQ ID NO 82
<211> LENGTH: 9
<212> TYPE: PRT
<213> ORGANISM: Homo sapiens

<400> SEQUENCE: 82
```

```
Ala Leu Ser Ser Val Ile Lys Glu Leu
1               5
```

<210> SEQ ID NO 83
<211> LENGTH: 10
<212> TYPE: PRT
<213> ORGANISM: Homo sapiens

<400> SEQUENCE: 83

```
Lys Leu Leu Glu Ile Asp Ile Asp Gly Val
1               5                   10
```

<210> SEQ ID NO 84
<211> LENGTH: 9
<212> TYPE: PRT
<213> ORGANISM: Homo sapiens

<400> SEQUENCE: 84

```
Lys Met Phe Glu Asn Glu Phe Leu Leu
1               5
```

<210> SEQ ID NO 85
<211> LENGTH: 11
<212> TYPE: PRT
<213> ORGANISM: Homo sapiens

<400> SEQUENCE: 85

```
Phe Ala Tyr Asp Gly Lys Asp Tyr Leu Thr Leu
1               5                   10
```

<210> SEQ ID NO 86
<211> LENGTH: 9
<212> TYPE: PRT
<213> ORGANISM: Homo sapiens

<400> SEQUENCE: 86

```
Lys Val Ile Asp Tyr Val Pro Gly Ile
1               5
```

<210> SEQ ID NO 87
<211> LENGTH: 9
<212> TYPE: PRT
<213> ORGANISM: Homo sapiens

<400> SEQUENCE: 87

```
Leu Leu Gln Asn Asn Leu Pro Ala Val
1               5
```

<210> SEQ ID NO 88
<211> LENGTH: 9
<212> TYPE: PRT
<213> ORGANISM: Homo sapiens

<400> SEQUENCE: 88

```
Thr Leu His Arg Glu Thr Phe Tyr Leu
1               5
```

<210> SEQ ID NO 89
<211> LENGTH: 9
<212> TYPE: PRT
<213> ORGANISM: Homo sapiens

<400> SEQUENCE: 89

```
Ile Gln His Asp Leu Ile Phe Ser Leu
1               5
```

```
<210> SEQ ID NO 90
<211> LENGTH: 11
<212> TYPE: PRT
<213> ORGANISM: Homo sapiens

<400> SEQUENCE: 90

Thr Leu Val Asp Asn Ile Ser Thr Met Ala Leu
1               5                   10

<210> SEQ ID NO 91
<211> LENGTH: 9
<212> TYPE: PRT
<213> ORGANISM: Homo sapiens

<400> SEQUENCE: 91

Lys Leu Gln Asp Gly Val His Ile Ile
1               5

<210> SEQ ID NO 92
<211> LENGTH: 9
<212> TYPE: PRT
<213> ORGANISM: Homo sapiens

<400> SEQUENCE: 92

Tyr Leu Gln Asp Tyr Thr Asp Arg Val
1               5

<210> SEQ ID NO 93
<211> LENGTH: 9
<212> TYPE: PRT
<213> ORGANISM: Homo sapiens

<400> SEQUENCE: 93

Ala Leu Arg Glu Thr Val Val Glu Val
1               5

<210> SEQ ID NO 94
<211> LENGTH: 11
<212> TYPE: PRT
<213> ORGANISM: Homo sapiens

<400> SEQUENCE: 94

Ala Leu Phe Pro Val Ala Glu Asp Ile Ser Leu
1               5                   10

<210> SEQ ID NO 95
<211> LENGTH: 9
<212> TYPE: PRT
<213> ORGANISM: Homo sapiens

<400> SEQUENCE: 95

Ala Leu Tyr Ser Lys Gly Ile Leu Leu
1               5

<210> SEQ ID NO 96
<211> LENGTH: 9
<212> TYPE: PRT
<213> ORGANISM: Homo sapiens

<400> SEQUENCE: 96

Asn Leu Leu Lys Leu Ile Ala Glu Val
1               5
```

```
<210> SEQ ID NO 97
<211> LENGTH: 10
<212> TYPE: PRT
<213> ORGANISM: Homo sapiens

<400> SEQUENCE: 97

Ala Leu Leu Asp Gly Thr Val Phe Glu Ile
1               5                   10

<210> SEQ ID NO 98
<211> LENGTH: 10
<212> TYPE: PRT
<213> ORGANISM: Homo sapiens

<400> SEQUENCE: 98

Ala Leu Val Asp His Leu Asn Val Gly Val
1               5                   10

<210> SEQ ID NO 99
<211> LENGTH: 11
<212> TYPE: PRT
<213> ORGANISM: Homo sapiens

<400> SEQUENCE: 99

Gln Met Leu Glu Ala Ile Lys Ala Leu Glu Val
1               5                   10

<210> SEQ ID NO 100
<211> LENGTH: 9
<212> TYPE: PRT
<213> ORGANISM: Homo sapiens

<400> SEQUENCE: 100

Val Ala Asp Pro Glu Thr Arg Thr Val
1               5

<210> SEQ ID NO 101
<211> LENGTH: 9
<212> TYPE: PRT
<213> ORGANISM: Homo sapiens

<400> SEQUENCE: 101

Ala Met Asn Ser Gln Ile Leu Glu Val
1               5

<210> SEQ ID NO 102
<211> LENGTH: 11
<212> TYPE: PRT
<213> ORGANISM: Homo sapiens

<400> SEQUENCE: 102

Ala Leu Phe Ala Arg Pro Asp Leu Leu Leu Leu
1               5                   10

<210> SEQ ID NO 103
<211> LENGTH: 9
<212> TYPE: PRT
<213> ORGANISM: Homo sapiens

<400> SEQUENCE: 103

Ser Leu Leu Glu Tyr Gln Met Leu Val
1               5

<210> SEQ ID NO 104
<211> LENGTH: 9
```

```
<212> TYPE: PRT
<213> ORGANISM: Homo sapiens

<400> SEQUENCE: 104

Thr Leu Ile Gln Phe Thr Val Lys Leu
1               5

<210> SEQ ID NO 105
<211> LENGTH: 9
<212> TYPE: PRT
<213> ORGANISM: Homo sapiens

<400> SEQUENCE: 105

Ser Met Tyr Asp Lys Val Leu Met Leu
1               5

<210> SEQ ID NO 106
<211> LENGTH: 9
<212> TYPE: PRT
<213> ORGANISM: Homo sapiens

<400> SEQUENCE: 106

Lys Met Pro Asp Asp Val Trp Leu Val
1               5

<210> SEQ ID NO 107
<211> LENGTH: 10
<212> TYPE: PRT
<213> ORGANISM: Homo sapiens

<400> SEQUENCE: 107

Ala Met Tyr Gly Thr Lys Leu Glu Thr Ile
1               5                   10

<210> SEQ ID NO 108
<211> LENGTH: 11
<212> TYPE: PRT
<213> ORGANISM: Homo sapiens

<400> SEQUENCE: 108

Ile Leu Leu Asp Asp Gln Phe Gln Pro Lys Leu
1               5                   10

<210> SEQ ID NO 109
<211> LENGTH: 9
<212> TYPE: PRT
<213> ORGANISM: Homo sapiens

<400> SEQUENCE: 109

Ser Leu Phe Glu Arg Leu Val Val Leu
1               5

<210> SEQ ID NO 110
<211> LENGTH: 10
<212> TYPE: PRT
<213> ORGANISM: Homo sapiens

<400> SEQUENCE: 110

Gly Leu Thr Glu Thr Gly Leu Tyr Arg Ile
1               5                   10

<210> SEQ ID NO 111
<211> LENGTH: 9
<212> TYPE: PRT
<213> ORGANISM: Homo sapiens
```

<400> SEQUENCE: 111

Phe Leu Pro Glu Ala Pro Ala Glu Leu
1               5

<210> SEQ ID NO 112
<211> LENGTH: 10
<212> TYPE: PRT
<213> ORGANISM: Homo sapiens

<400> SEQUENCE: 112

Leu Leu Leu Pro Gly Val Ile Lys Thr Val
1               5                   10

<210> SEQ ID NO 113
<211> LENGTH: 9
<212> TYPE: PRT
<213> ORGANISM: Homo sapiens

<400> SEQUENCE: 113

Leu Thr Asp Pro Asp Ile His Val Leu
1               5

<210> SEQ ID NO 114
<211> LENGTH: 11
<212> TYPE: PRT
<213> ORGANISM: Homo sapiens

<400> SEQUENCE: 114

Ala Leu Leu Glu Pro Gly Gly Val Leu Thr Ile
1               5                   10

<210> SEQ ID NO 115
<211> LENGTH: 11
<212> TYPE: PRT
<213> ORGANISM: Homo sapiens

<400> SEQUENCE: 115

Ala Leu Leu Pro Ser Asp Cys Leu Gln Glu Ala
1               5                   10

<210> SEQ ID NO 116
<211> LENGTH: 9
<212> TYPE: PRT
<213> ORGANISM: Homo sapiens

<400> SEQUENCE: 116

Ala Leu Leu Val Arg Leu Gln Glu Val
1               5

<210> SEQ ID NO 117
<211> LENGTH: 10
<212> TYPE: PRT
<213> ORGANISM: Homo sapiens

<400> SEQUENCE: 117

Phe Leu Leu Asp Ser Ala Pro Leu Asn Val
1               5                   10

<210> SEQ ID NO 118
<211> LENGTH: 9
<212> TYPE: PRT
<213> ORGANISM: Homo sapiens

<400> SEQUENCE: 118

```
Lys Leu Pro Ser Phe Leu Ala Asn Val
1               5
```

<210> SEQ ID NO 119
<211> LENGTH: 11
<212> TYPE: PRT
<213> ORGANISM: Homo sapiens

<400> SEQUENCE: 119

```
Ser Leu Ile Asp Asp Asn Asn Glu Ile Asn Leu
1               5                   10
```

<210> SEQ ID NO 120
<211> LENGTH: 9
<212> TYPE: PRT
<213> ORGANISM: Homo sapiens

<400> SEQUENCE: 120

```
Ser Leu Ala Ala Asp Ile Pro Arg Leu
1               5
```

<210> SEQ ID NO 121
<211> LENGTH: 9
<212> TYPE: PRT
<213> ORGANISM: Homo sapiens

<400> SEQUENCE: 121

```
Tyr Met Leu Glu His Val Ile Thr Leu
1               5
```

<210> SEQ ID NO 122
<211> LENGTH: 11
<212> TYPE: PRT
<213> ORGANISM: Homo sapiens

<400> SEQUENCE: 122

```
Ser Met Met Pro Asp Glu Leu Leu Thr Ser Leu
1               5                   10
```

<210> SEQ ID NO 123
<211> LENGTH: 9
<212> TYPE: PRT
<213> ORGANISM: Homo sapiens

<400> SEQUENCE: 123

```
Lys Leu Asp Lys Asn Pro Asn Gln Val
1               5
```

<210> SEQ ID NO 124
<211> LENGTH: 9
<212> TYPE: PRT
<213> ORGANISM: Homo sapiens

<400> SEQUENCE: 124

```
Ser Leu Ile Thr Asp Leu Gln Thr Ile
1               5
```

<210> SEQ ID NO 125
<211> LENGTH: 11
<212> TYPE: PRT
<213> ORGANISM: Homo sapiens

<400> SEQUENCE: 125

```
Leu Leu Ser Glu Pro Ser Leu Leu Arg Thr Val
```

<210> SEQ ID NO 126
<211> LENGTH: 9
<212> TYPE: PRT
<213> ORGANISM: Homo sapiens

<400> SEQUENCE: 126

Ala Ala Ala Ser Leu Ile Arg Leu Val
1               5

<210> SEQ ID NO 127
<211> LENGTH: 9
<212> TYPE: PRT
<213> ORGANISM: Homo sapiens

<400> SEQUENCE: 127

Ser Gln Ala Pro Val Leu Asp Ala Ile
1               5

<210> SEQ ID NO 128
<211> LENGTH: 10
<212> TYPE: PRT
<213> ORGANISM: Homo sapiens

<400> SEQUENCE: 128

Ser Leu Ala Pro Ala Gly Val Ile Arg Val
1               5                   10

<210> SEQ ID NO 129
<211> LENGTH: 9
<212> TYPE: PRT
<213> ORGANISM: Homo sapiens

<400> SEQUENCE: 129

Arg Val Ala Asp Tyr Ile Val Lys Val
1               5

<210> SEQ ID NO 130
<211> LENGTH: 10
<212> TYPE: PRT
<213> ORGANISM: Homo sapiens

<400> SEQUENCE: 130

Ser Leu Tyr Asp Asn Gln Ile Thr Thr Val
1               5                   10

<210> SEQ ID NO 131
<211> LENGTH: 10
<212> TYPE: PRT
<213> ORGANISM: Homo sapiens

<400> SEQUENCE: 131

Ile Leu Met Gly Thr Glu Leu Thr Gln Val
1               5                   10

<210> SEQ ID NO 132
<211> LENGTH: 9
<212> TYPE: PRT
<213> ORGANISM: Homo sapiens

<400> SEQUENCE: 132

Asn Leu Leu Ala Glu Ile His Gly Val
1               5

<210> SEQ ID NO 133
<211> LENGTH: 9
<212> TYPE: PRT
<213> ORGANISM: Homo sapiens

<400> SEQUENCE: 133

Ile Met Glu Asp Ile Ile Leu Thr Leu
1               5

<210> SEQ ID NO 134
<211> LENGTH: 11
<212> TYPE: PRT
<213> ORGANISM: Homo sapiens

<400> SEQUENCE: 134

Phe Met Ile Asp Ala Ser Val His Pro Thr Leu
1               5                   10

<210> SEQ ID NO 135
<211> LENGTH: 9
<212> TYPE: PRT
<213> ORGANISM: Homo sapiens

<400> SEQUENCE: 135

Ser Leu Met Met Thr Ile Ile Asn Leu
1               5

<210> SEQ ID NO 136
<211> LENGTH: 11
<212> TYPE: PRT
<213> ORGANISM: Homo sapiens

<400> SEQUENCE: 136

Phe Leu Pro Pro Glu His Thr Ile Val Tyr Ile
1               5                   10

<210> SEQ ID NO 137
<211> LENGTH: 9
<212> TYPE: PRT
<213> ORGANISM: Homo sapiens

<400> SEQUENCE: 137

Asn Leu Leu Glu Leu Phe Val Gln Leu
1               5

<210> SEQ ID NO 138
<211> LENGTH: 11
<212> TYPE: PRT
<213> ORGANISM: Homo sapiens

<400> SEQUENCE: 138

Arg Leu Leu Asp Phe Pro Glu Ala Met Val Leu
1               5                   10

<210> SEQ ID NO 139
<211> LENGTH: 9
<212> TYPE: PRT
<213> ORGANISM: Homo sapiens

<400> SEQUENCE: 139

Phe Leu Ser Ser Val Thr Tyr Asn Leu
1               5

<210> SEQ ID NO 140

```
<211> LENGTH: 9
<212> TYPE: PRT
<213> ORGANISM: Homo sapiens

<400> SEQUENCE: 140

Gly Leu Leu Glu Val Met Val Asn Leu
1               5

<210> SEQ ID NO 141
<211> LENGTH: 9
<212> TYPE: PRT
<213> ORGANISM: Homo sapiens

<400> SEQUENCE: 141

Asn Leu Pro Glu Tyr Leu Pro Phe Val
1               5

<210> SEQ ID NO 142
<211> LENGTH: 10
<212> TYPE: PRT
<213> ORGANISM: Homo sapiens

<400> SEQUENCE: 142

Glu Leu Ala Gly Ile Gly Ile Leu Thr Val
1               5                   10

<210> SEQ ID NO 143
<211> LENGTH: 9
<212> TYPE: PRT
<213> ORGANISM: Homo sapiens

<400> SEQUENCE: 143

Tyr Leu Leu Pro Ala Ile Val His Ile
1               5

<210> SEQ ID NO 144
<211> LENGTH: 6
<212> TYPE: PRT
<213> ORGANISM: Artificial Sequence
<220> FEATURE:
<223> OTHER INFORMATION: Linker sequence

<400> SEQUENCE: 144

Leu Leu Leu Leu Leu Leu
1               5
```

PEPTIDES AND COMBINATION OF PEPTIDES FOR USE IN IMMUNOTHERAPY AGAINST SMALL CELL LUNG CANCER AND OTHER CANCERS

CROSS REFERENCE TO RELATED APPLICATIONS

This application is a continuation of U.S. application Ser. No. 16/237,279, filed Dec. 31, 2018 (now U.S. Pat. No. 10,487,126, issued Nov. 26, 2019), which is a continuation of U.S. application Ser. No. 15/281,537, filed Sep. 30, 2016 (now U.S. Pat. No. 10,253,077, issued Apr. 9, 2019), which claims the benefit of U.S. Provisional Application Ser. No. 62/237,091, filed Oct. 5, 2015, and claims priority from Great Britain Application No. 1517538.3, filed Oct. 5, 2015, the content of each of these applications is herein incorporated by reference in their entirety.

This application also is related to PCT/EP2016/073416 filed Oct. 30, 2016, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-055007_ST25.txt" created on Sep. 23, 2019, and 22,739 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Small Cell Lung Cancer (SCLC)

Small cell lung cancer (SCLC) is named according to the size of the cancer cells when observed under a microscope and has to be differentiated from non-small cell lung cancer (NSCLC). SCLC accounts to about 10% to 15% of all lung cancers (American Cancer Society, 2015a).

Both lung cancers (SCLC and NSCLC) are the second most common cancer in both men and women. Lung cancer is leading cause of cancer death, which accounts for about 25%. Thus, more people die of lung cancer than of colon, breast, and prostate cancers combined each year. Furthermore, both lung cancers account for about 13% (more than 1.8 million) of all new cancers. Lung cancer mainly occurs in older people. The average age at the time of diagnosis is about 70. Fewer than 2% of all cases are diagnosed in people younger than 45. The treatment and prognosis of SCLC depend strongly on the diagnosed cancer stage. The staging of SCLC based on clinical results is more common than the pathologic staging. The clinical staging uses the results of the physical examination, various imaging tests and biopsies. According to the data introduced by American Cancer Society the 5-year relative survival rate accounts to 31% for stage I, 19% for stage II, 8% for stage III, and 2% for stage IV.

The standard chemo treatment of SCLC uses the combination of either etoposide or irinotecan with either cisplatin or carboplatin. The treatment is given in 4 to 6 cycles. Each cycle begins with the chemo treatment for 1 to 3 days followed by recovery period of 3 to 4 weeks.

The standard radiation therapy for treatment of SCLC is called external beam radiation therapy (EBRT) and usually given once or twice a day, 5 days a week, for 3 to 7 weeks. In the last few years, the new radiation techniques have been developed. The new techniques are three-dimensional conformal radiation therapy (3D-CRT) and intensity modulated radiation therapy (IMRT). Both of them allow the more precise targeting of radiation load towards tumor by lowering the radiation exposure to surrounding healthy tissue.

At the stage I, when SCLC is found as a single small tumor with no evidence of cancer spread in lymph nodes or elsewhere in general (less than in 1 out of 20 patients), a surgery followed by combined chemo- and radiation therapy is a standard treatment. This treatment procedure is only an option for patients with fairly good health. Mostly, by the time when SCLC is diagnosed it has already spread. Thus, the treatment by surgery is unlikely (American Cancer Society, 2015a; S3-Leitlinie Lungenkarzinom, 2011).

At the limited stage, when SCLC has spread throughout one side of the chest to the lung or nearby lymph nodes (1 out of 3 patients) the combined chemo- and radiation therapy so-called concurrent chemoradiation is a standard treatment. At this stage, the surgery is not an option. The standard chemo drugs are etoposide (VP-16) together with either cisplatin or carboplatin. The concurrent combination of chemo- with radiation therapy showed therapeutic advantages but also is followed by severe side effects compared to the chemo or radiation treatment by itself. The patients who are unlikely to tolerate the concurrent chemoradiation, chemo therapy is a standard treatment. Optionally chemo therapy can be followed by radiation therapy (American Cancer Society, 2015a; S3-Leitlinie Lungenkarzinom, 2011).

At the extensive stage, when SCLC has spread widely throughout the lung, nearby lymph nodes and other distant organs (like bone marrow) the systematic chemotherapy mostly etoposide combined with either cisplatin or carboplatin optionally followed by radiation treatment to the chest is the applied treatment (American Cancer Society, 2015a; S3-Leitlinie Lungenkarzinom, 2011).

Since SCLC is known to spread to the brain, the patients with SCLC independently on the stage will be given the prophylactic radiation therapy to the head so-called prophylactic cranial irradiation or PCI.

At the limited and extensive stage, the treatment is likely to result in significant shrinking of the cancer but in the most cases the cancer will return at some point. The change in type of chemotherapy is to consider in the cases, when cancer continues to grow in spite of applied chemotherapy. The choice of chemotherapy by reoccurring cancer depends on the duration of cancer remission phase.

Innovations occurred regarding detection, diagnosis and treatment of SCLC. It was shown that the usage of CT scans instead of x-rays for early cancer detection lowered the risk of death from lung cancer. Nowadays, the diagnosis of SCLC can be supported by fluorescence or virtual bronchoscopy, the real-time tumor imagining can be implemented by the radiation treatment. The novel anti-angiogenesis drugs like bevacizumab (Avastin), sunitinib (Sutent) and nintedanib (BIBF 1120) were shown to have therapeutic effects in treatment of SCLC (American Cancer Society, 2015a).

The immune therapy presents an excessively investigated field of cancer therapy. Various approaches are studded in the treatment of SCLC. One of the approaches targets the blocking of CTLA-4, a natural human immune suppressor. The inhibition of CTLA-4 intends to boost the immune system to combat the cancer. Recently, the development of promising immune check point inhibitors for treatment of SCLC has been started. Another approach is based on anti-cancer vaccines which is currently available for treatment of SCLC in clinical studies (American Cancer Society, 2015b; National Cancer Institute (NCI), 2011).

Considering the severe side-effects and expense associated with treating cancer, there is a need to identify factors that can be used in the treatment of cancer in general and small cell lung cancer in particular. There is also a need to identify factors representing biomarkers for cancer in general and small cell lung cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell-(CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006; Dengjel et al., 2006). Elongated (longer) peptides of the invention can function as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 126 or a variant sequence thereof which is at least 77%, preferably at least 88%, homologous (preferably at least 77% or at least 88% identical) to SEQ ID NO: 1 to SEQ ID NO: 126, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 126 or a variant thereof, which is at least 77%, preferably at least 88%, homologous (preferably at least 77% or at least 88% identical) to SEQ ID NO: 1 to SEQ ID NO: 126, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention.

| SEQ ID No | Sequence | Gene ID(s) | Official Gene Symbol(s) |
|---|---|---|---|
| 1 | AMLEEVNYI | 9134 | CCNE2 |
| 2 | VMFNFPDQATV | 26960 | NBEA |
| 3 | VLAEIDPKQLV | 28981 | IFT81 |
| 4 | GLLDPGMLVNI | 7182 | NR2C2 |
| 5 | SLQSLIISV | 7398 | USP1 |
| 6 | SIMDYVVFV | 8884 | SLC5A6 |
| 7 | GLLGDIAIHL | 84059 | GPR98 |
| 8 | VLIDDSQSIIFI | 57380 | MRS2 |
| 9 | AAAPGEALHTA | 153572 | IRX2 |
| 10 | ILAAGFDGM | 149175 | MANEAL |
| 11 | KLFAIPILL | 2328 | FMO3 |
| 12 | MLFEGLDLVSA | 56603 | CYP26B1 |
| 13 | FLTAFLVQI | 392 | ARHGAP1 |
| 14 | ILIETKLVL | 3708 | ITPR1 |
| 15 | SLLTAISEV | 55086 | CXorf57 |
| 16 | VILDLPLVI | 101060503, 10628 | TXNIP |
| 17 | SLMLVTVEL | 8546 | AP3B1 |
| 18 | ALGEISVSV | 23113 | CUL9 |
| 19 | VLLTTAVEV | 23677 | SH3BP4 |

TABLE 1-continued

Peptides according to the present invention.

| SEQ ID No | Sequence | Gene ID(s) | Official Gene Symbol(s) |
|---|---|---|---|
| 20 | MLDEILLQL | 5425 | POLD2 |
| 21 | TMEEMIFEV | 2140 | EYA3 |
| 22 | LLPEKSWEI | 6898 | TAT |
| 23 | YQIDTVINL | 50808 | AK3 |
| 24 | FLMEEVHMI | 10057 | ABCC5 |
| 25 | GLSETILAV | 9631 | NUP155 |
| 26 | KMLDEAVFQV | 89796 | NAV1 |
| 27 | SLDIITITV | 79572 | ATP13A3 |
| 28 | ILVSQLEQL | 10844 | TUBGCP2 |
| 29 | NLISQLTTV | 22979 | EFR3B |
| 30 | KMLGLTVSL | 51651 | PTRH2 |
| 31 | RLLQDPVGV | 6002 | RGS12 |
| 32 | ALTSLELEL | 163732 | CITED4 |
| 33 | GLYSKTSQSV | 27032 | ATP2C1 |
| 34 | LVFEGIMEV | 11215 | AKAP11 |
| 35 | FMGDVFINV | 23491 | CES3 |
| 36 | RMDGAVTSV | 8648 | NCOA1 |
| 37 | SLFYNELHYV | 114793 | FMNL2 |
| 38 | GLISSLNEI | 6578 | SLCO2A1 |
| 39 | GLDPTQFRV | 5422 | POLA1 |
| 40 | GLLEVQVEV | 84171 | LOXL4 |
| 41 | KAYQELLATV | 8914 | TIMELESS |
| 42 | GLLEDERALQL | 92312 | MEX3A |
| 43 | YLWSEVFSM | 57486 | NLN |
| 44 | ALIVGIPSV | 7976 | FZD3 |
| 45 | SLSGEIILHSV | 121441 | NEDD1 |
| 46 | ALWVAVPKA | 93109 | TMEM44 |
| 47 | GLLEALLKI | 57187 | THOC2 |
| 48 | SLIGLDLSSV | 9765 | ZFYVE16 |
| 49 | RLALNTPKV | 23094 | SIPA1L3 |
| 50 | FLLSQIVAL | 347051 | SLC10A5 |
| 51 | ILDEAGVKYFL | 113828 | FAM83F |
| 52 | ILASFMLTGV | 9931 | HELZ |
| 53 | LLSEEHITL | 9969 | MED13 |
| 54 | HLFDIILTSV | 79659 | DYNC2H1 |
| 55 | LLIADNPQL | 7404 | UTY |
| 56 | SLFSQMGSQYEL | 79192 | IRX1 |

TABLE 1-continued

Peptides according to the present invention.

| SEQ ID No | Sequence | Gene ID(s) | Official Gene Symbol(s) |
|---|---|---|---|
| 57 | VLIGDVLVAV | 27152 | INTU |
| 58 | VLLNINGIDL | 222484 | LNX2 |
| 59 | VLLSGLTEV | 9498 | SLC4A8 |
| 60 | VVSGATETL | 23547 | LILRA4 |
| 61 | YQAPYFLTV | 9890 | LPPR4 |
| 62 | VMLPIGAVVMV | 151258 | SLC38A11 |
| 63 | LLMSTENEL | 4602 | MYB |
| 64 | VLFHQLQEI | 25821 | MTO1 |
| 65 | VMYDLITEL | 3782 | KCNN3 |
| 66 | YLNLISTSV | 55757 | UGGT2 |
| 67 | MLYDIVPVV | 151963 | MB21D2 |
| 68 | FLFPVYPLI | 79796, 91893 | ALG9, FDXACB1 |
| 69 | KLFDRSVDL | 55957 | LIN37 |
| 70 | TLLWKLVEV | 54901 | CDKAL1 |
| 71 | FIFEQVQNV | 83852 | SETDB2 |
| 72 | KAIGSLKEV | 1894 | ECT2 |
| 73 | SLSSYTPDV | 29843 | SENP1 |
| 74 | FLDSLSPSV | 65250 | C5orf42 |
| 75 | SLDLHVPSL | 51750, 8771 | RTEL1, TNFRSF6B |
| 76 | VLTTVMITV | 166929 | SGMS2 |

TABLE 2

Additional peptides according to the present invention with no prior known cancer association.

| SEQ ID No | Sequence | Gene ID(s) | Official Gene Symbol(s) |
|---|---|---|---|
| 77 | AIIDGKIFCV | 5531 | PPP4C |
| 78 | RIIDPEDLKALL | 29994 | BAZ2B |
| 79 | RLLEPAQVQQL | 152002 | XXYLT1 |
| 80 | ILMDPSPEYA | 1786 | DNMT1 |
| 81 | LLAEIGAVTLV | 79042 | TSEN34 |
| 82 | ALSSVIKEL | 440145 | MZT1 |
| 83 | KLLEIDIDGV | 5422 | POLA1 |
| 84 | KMFENEFLL | 29 | ABR |
| 85 | FAYDGKDYLTL | 3133 | HLA-E |
| 86 | KVIDYVPGI | 25976 | TIPARP |
| 87 | LLQNNLPAV | 22948 | CCT5 |
| 88 | TLHRETFYL | 9134 | CCNE2 |
| 89 | IQHDLIFSL | 3091 | HIF1A |
| 90 | TLVDNISTMAL | 55856 | ACOT13 |
| 91 | KLQDGVHII | 51118 | UTP11L |
| 92 | YLQDYTDRV | 10946 | SF3A3 |
| 93 | ALRETVVEV | 7415 | VCP |
| 94 | ALFPVAEDISL | 84164 | ASCC2 |
| 95 | ALYSKGILL | 9631 | NUP155 |
| 96 | NLLKLIAEV | 57405 | SPC25 |
| 97 | ALLDGTVFEI | 8214, 85359 | DGCR6, DGCR6L |
| 98 | ALVDHLNVGV | 2647 | BLOC1S1 |
| 99 | QMLEAIKALEV | 7690 | ZNF131 |
| 100 | VADPETRTV | 11284 | PNKP |
| 101 | AMNSQILEV | 23036 | ZNF292 |
| 102 | ALFARPDLLLL | 55324 | ABCF3 |
| 103 | SLLEYQMLV | 23511 | NUP188 |
| 104 | TLIQFTVKL | 6775 | STAT4 |
| 105 | SMYDKVLML | 9328 | GTF3C5 |
| 106 | KMPDDVWLV | 8567 | MADD |
| 107 | AMYGTKLETI | 8573 | CASK |
| 108 | ILLDDQFQPKL | 11213 | IRAK3 |
| 109 | SLFERLVVL | 5976 | UPF1 |
| 110 | GLTETGLYRI | 29127, 83956 | RACGAP1, RACGAP1P |
| 111 | FLPEAPAEL | 4171 | MCM2 |
| 112 | LLLPGVIKTV | 3980 | LIG3 |
| 113 | LTDPDIHVL | 23335 | WDR7 |
| 114 | ALLEPGGVLTI | 23195 | MDN1 |
| 115 | ALLPSDCLQEA | 64410 | KLHL25 |
| 116 | ALLVRLQEV | 3695 | ITGB7 |
| 117 | FLLDSAPLNV | 134430 | WDR36 |
| 118 | KLPSFLANV | 2585 | GALK2 |
| 119 | SLIDDNNEINL | 65975 | STK33 |
| 120 | SLAADIPRL | 171425 | CLYBL |
| 121 | YMLEHVITL | 9735 | KNTC1 |
| 122 | SMMPDELLTSL | 9994 | CASP8AP2 |
| 123 | KLDKNPNQV | 9994 | CASP8AP2 |

TABLE 2-continued

Additional peptides according to the present invention with no prior known cancer association.

| SEQ ID No | Sequence | Gene ID(s) | Official Gene Symbol(s) |
|---|---|---|---|
| 124 | SLITDLQTI | 26005 | C2CD3 |
| 125 | LLSEPSLLRTV | 91442 | C19orf40 |
| 126 | AAASLIRLV | 3064 | HTT |

TABLE 3

Peptides useful for e.g. personalized cancer therapies.

| SEQ ID No | Sequence | Gene ID(s) | Official Gene Symbol(s) |
|---|---|---|---|
| 127 | SQAPVLDAI | 1293 | COL6A3 |
| 128 | SLAPAGVIRV | 30012 | TLX3 |
| 129 | RVADYIVKV | 201780 | SLC10A4 |
| 130 | SLYDNQITTV | 6585, 9353 | SLIT1, SLIT2 |
| 131 | ILMGTELTQV | 10439 | OLFM1 |
| 132 | NLLAEIHGV | 10570 | DPYSL4 |
| 133 | IMEDIILTL | 1656 | DDX6 |
| 134 | FMIDASVHPTL | 221960, 51622 | CCZ1, CCZ1B |
| 135 | SLMMTIINL | 7153 | TOP2A |
| 136 | FLPPEHTIVYI | 9896 | FIG4 |
| 137 | NLLELFVQL | 5297 | PI4KA |
| 138 | RLLDFPEAMVL | 23113 | CUL9 |
| 139 | FLSSVTYNL | 23312 | DMXL2 |
| 140 | GLLEVMVNL | 23001 | WDFY3 |
| 141 | NLPEYLPFV | 55832, 91689 | C22orf32, CAND1 |

TABLE 3-continued

Peptides useful for e.g. personalized cancer therapies.

| SEQ ID No | Sequence | Gene ID(s) | Official Gene Symbol(s) |
|---|---|---|---|

The present invention furthermore generally relates to the peptides according to the present invention for use in the treatment of proliferative diseases, such as, for example, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

Particularly preferred are the peptides—alone or in combination—according to the present invention selected from the group consisting of SEQ ID NO: 1 to SEQ ID NO: 126. More preferred are the peptides—alone or in combination—selected from the group consisting of SEQ ID NO: 1 to SEQ ID NO: 76 (see Table 1), and their uses in the immunotherapy of small cell lung cancer, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably small cell lung cancer.

Even more preferred are the peptides—alone or in combination—selected from the group consisting of SEQ ID NO: 7, 8, 33, 39, 40, 45, 47, 58, 59, 73, 79, 80, 81, 88, 110, 111, 112, and 115, and their uses in the immunotherapy of small cell lung cancer, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably small cell lung cancer. Most preferred is the peptide of SEQ ID NO: 72.

As shown in the following Tables 4A and B, many of the peptides according to the present invention are also found on other tumor types and can, thus, also be used in the immunotherapy of other indications. Also refer to FIGS. 1A-1P and Example 1.

TABLE 4A

Peptides according to the present invention and their specific uses in other proliferative diseases than SCLC, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Other relevant organs/diseases |
|---|---|---|
| 1 | AMLEEVNYI | PC, Leukemia |
| 2 | VMFNFPDQATV | PrC |

TABLE 4A-continued

Peptides according to the present invention and their specific uses in other proliferative diseases than SCLC, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Other relevant organs/diseases |
|---|---|---|
| 3 | VLAEIDPKQLV | HCC, OC |
| 4 | GLLDPGMLVNI | Uterine Cancer |
| 6 | SIMDYVVFV | GC, CRC, HCC, BRCA, Urinary bladder cancer, Gallbladder Cancer, Bile Duct Cancer |
| 7 | GLLGDIAIHL | Brain Cancer, BRCA, Uterine Cancer |
| 8 | VLIDDSQSIIFI | Leukemia, OC |
| 9 | AAAPGEALHTA | NSCLC, BRCA, MCC, Esophageal Cancer, Urinary bladder cancer |
| 11 | KLFAIPILL | HCC, Gallbladder Cancer, Bile Duct Cancer |
| 12 | MLFEGLDLVSA | PrC |
| 13 | FLTAFLVQI | Leukemia, Urinary bladder cancer |
| 14 | ILIETKLVL | Leukemia |
| 15 | SLLTAISEV | Brain Cancer, HCC, PC, Urinary bladder cancer, Gallbladder Cancer, Bile Duct Cancer |
| 16 | VILDLPLVI | PC, Leukemia |
| 17 | SLMLVTVEL | PC, Leukemia, BRCA, Urinary bladder cancer |
| 18 | ALGEISVSV | Leukemia |
| 19 | VLLTTAVEV | BRCA, Uterine Cancer |
| 20 | MLDEILLQL | RCC, GC, CRC, Leukemia, Urinary bladder cancer |
| 21 | TMEEMIFEV | CRC, Leukemia, Urinary bladder cancer, Gallbladder Cancer, Bile Duct Cancer |
| 22 | LLPEKSWEI | HCC |
| 23 | YQIDTVINL | PrC, Urinary bladder cancer |
| 24 | FLMEEVHMI | NSCLC, CRC, Melanoma, Gallbladder Cancer, Bile Duct Cancer |
| 25 | GLSETILAV | NSCLC, Brain Cancer, CRC, HCC, PC, PrC, Leukemia, BRCA, Melanoma, Esophageal Cancer, OC, Urinary bladder cancer, Uterine Cancer, Gallbladder Cancer, Bile Duct Cancer |
| 26 | KMLDEAVFQV | NSCLC, Brain Cancer, CRC, BRCA, Melanoma, Urinary bladder cancer |
| 27 | SLDIITITV | NSCLC, RCC, Brain Cancer, GC, HCC, PC, BRCA, Melanoma, Urinary bladder cancer, Gallbladder Cancer, Bile Duct Cancer |
| 28 | ILVSQLEQL | Gallbladder Cancer, Bile Duct Cancer |
| 29 | NLISQLTTV | Brain Cancer |
| 30 | KMLGLTVSL | CRC, BRCA, OC, Gallbladder Cancer, Bile Duct Cancer |

TABLE 4A-continued

Peptides according to the present invention and their specific uses in other proliferative diseases than SCLC, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Other relevant organs/diseases |
| --- | --- | --- |
| 31 | RLLQDPVGV | Brain Cancer, HCC, PrC, BRCA, Uterine Cancer |
| 32 | ALTSLELEL | HCC, PrC, BRCA, OC, Uterine Cancer, Gallbladder Cancer, Bile Duct Cancer |
| 33 | GLYSKTSQSV | NSCLC, HCC, Esophageal Cancer |
| 34 | LVFEGIMEV | Leukemia, Urinary bladder cancer, Uterine Cancer |
| 37 | SLFYNELHYV | Melanoma |
| 38 | GLISSLNEI | Leukemia |
| 39 | GLDPTQFRV | Urinary bladder cancer |
| 43 | YLWSEVFSM | Leukemia |
| 45 | SLSGEIILHSV | NSCLC, CRC, Melanoma, Urinary bladder cancer |
| 47 | GLLEALLKI | Leukemia |
| 49 | RLALNTPKV | HCC, Leukemia |
| 52 | ILASFMLTGV | Leukemia |
| 53 | LLSEEHITL | Leukemia, Urinary bladder cancer |
| 57 | VLIGDVLVAV | OC |
| 58 | VLLNINGIDL | Urinary bladder cancer |
| 59 | VLLSGLTEV | Brain Cancer, Leukemia |
| 61 | YQAPYFLTV | Brain Cancer, OC, Urinary bladder cancer, Uterine Cancer |
| 64 | VLFHQLQEI | Leukemia, Melanoma |
| 65 | VMYDLITEL | NSCLC, PC, BRCA, Uterine Cancer, Gallbladder Cancer, Bile Duct Cancer |
| 66 | YLNLISTSV | Urinary bladder cancer, Gallbladder Cancer, Bile Duct Cancer |
| 67 | MLYDIVPVV | NSCLC, PC, OC, Urinary bladder cancer |
| 68 | FLFPVYPLI | Brain Cancer, CRC, Melanoma, Urinary bladder cancer |
| 69 | KLFDRSVDL | NSCLC, RCC, Brain Cancer, CRC, HCC, PC, BRCA, OC, Urinary bladder cancer |
| 72 | KAIGSLKEV | OC |
| 73 | SLSSYTPDV | Leukemia |
| 76 | VLTTVMITV | PC, OC |
| 77 | AIIDGKIFCV | GC, Urinary bladder cancer |
| 78 | RIIDPEDLKALL | NSCLC, CRC, HCC, Urinary bladder cancer, Uterine Cancer |

TABLE 4A-continued

Peptides according to the present invention and their specific uses in other proliferative diseases than SCLC, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Other relevant organs/diseases |
|---|---|---|
| 79 | RLLEPAQVQQL | NSCLC, Brain Cancer, HCC, BRCA, Esophageal Cancer |
| 80 | ILMDPSPEYA | Brain Cancer, BRCA, MCC, Melanoma, Urinary bladder cancer |
| 81 | LLAEIGAVTLV | NSCLC, HCC, Melanoma, OC, Urinary bladder cancer |
| 82 | ALSSVIKEL | CRC, Esophageal Cancer, Urinary bladder cancer, Uterine Cancer |
| 83 | KLLEIDIDGV | Brain Cancer, CRC, Leukemia, BRCA, MCC, OC, Urinary bladder cancer, Uterine Cancer |
| 84 | KMFENEFLL | CRC, Leukemia, Urinary bladder cancer, Gallbladder Cancer, Bile Duct Cancer |
| 85 | FAYDGKDYLTL | RCC, Leukemia, BRCA, Esophageal Cancer |
| 86 | KVIDYVPGI | NSCLC, Brain Cancer, HCC, BRCA, Esophageal Cancer, OC, Gallbladder Cancer, Bile Duct Cancer |
| 87 | LLQNNLPAV | Leukemia, Melanoma, OC, Urinary bladder cancer |
| 88 | TLHRETFYL | OC, Urinary bladder cancer, Gallbladder Cancer, Bile Duct Cancer |
| 89 | IQHDLIFSL | GC |
| 90 | TLVDNISTMAL | CRC, OC |
| 91 | KLQDGVHII | NSCLC, Gallbladder Cancer, Bile Duct Cancer |
| 92 | YLQDYTDRV | Leukemia, OC |
| 93 | ALRETVVEV | NSCLC, Brain Cancer, Leukemia, BRCA, Esophageal Cancer, OC, Urinary bladder cancer, Gallbladder Cancer, Bile Duct Cancer |
| 94 | ALFPVAEDISL | NSCLC, Leukemia, Urinary bladder cancer |
| 95 | ALYSKG | ILL NSCLC, RCC, CRC, HCC, MCC, Esophageal Cancer, OC, Urinary bladder cancer |
| 96 | NLLKLIAEV | RCC, Brain Cancer, CRC, HCC, Melanoma, Uterine Cancer, Gallbladder Cancer, Bile Duct Cancer |
| 97 | ALLDGTVFEI | Brain Cancer, HCC, MCC, OC, Urinary bladder cancer |
| 98 | ALVDHLNVGV | Brain Cancer, HCC, PrC, Leukemia, OC, Uterine Cancer, Gallbladder Cancer, Bile Duct Cancer |
| 99 | QMLEAIKALEV | CRC, Leukemia, Melanoma, Urinary bladder cancer |
| 101 | AMNSQILEV | Brain Cancer, CRC, Leukemia, BRCA, Uterine Cancer |
| 102 | ALFARPDLLLL | Leukemia, Melanoma, OC, Urinary bladder cancer |
| 103 | SLLEYQMLV | BRCA, Urinary bladder cancer, Gallbladder Cancer, |

TABLE 4A-continued

Peptides according to the present invention and their specific uses in other proliferative diseases than SCLC, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Other relevant organs/diseases |
|---|---|---|
| | | Bile Duct Cancer |
| 105 | SMYDKVLML | MCC, OC |
| 106 | KMPDDVWLV | BRCA, Uterine Cancer |
| 107 | AMYGTKLETI | CRC, HCC, PC, OC |
| 108 | ILLDDQFQPKL | Melanoma |
| 109 | SLFERLVVL | HCC, MCC, Urinary bladder cancer |
| 110 | GLTETGLYRI | NSCLC, CRC, PC, Leukemia, Esophageal Cancer, OC, Gallbladder Cancer, Bile Duct Cancer |
| 111 | FLPEAPAEL | Leukemia, Gallbladder Cancer, Bile Duct Cancer |
| 112 | LLLPGVIKTV | Leukemia |
| 116 | ALLVRLQEV | Leukemia |
| 118 | KLPSFLANV | HCC, Uterine Cancer, Gallbladder Cancer, Bile Duct Cancer |
| 119 | SLIDDNNEINL | OC, Uterine Cancer |
| 121 | YMLEHVITL | CRC, Leukemia, MCC, Melanoma, OC, Urinary bladder cancer, Gallbladder Cancer, Bile Duct Cancer |
| 123 | KLDKNPNQV | Leukemia, Urinary bladder cancer |
| 124 | SLITDLQTI | NSCLC, Brain Cancer, CRC, BRCA, OC, Urinary bladder cancer, Uterine Cancer |
| 126 | AAASLIRLV | Leukemia, BRCA |

NSCLC = non-small cell lung cancer, RCC = kidney cancer, CRC = colon or rectum cancer, GC = stomach cancer, HCC = liver cancer, PC = pancreatic cancer, PrC = prostate cancer, leukemia, BrCa = breast cancer, MCC = Merkel cell carcinoma, OC = ovarian cancer

TABLE 4B

Peptides according to the present invention and their specific uses in other proliferative diseases, especially in other cancerous diseases (amendment of Table 4). This table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID No | Sequence | Additional Entities |
|---|---|---|
| 4 | GLLDPGMLVNI | Brain Cancer |
| 13 | FLTAFLVQI | RCC |
| 14 | ILIETKLVL | CLL, NHL |
| 16 | VILDLPLVI | CLL, HNSCC |
| 17 | SLMLVTVEL | CLL, Melanoma, NHL |
| 20 | MLDEILLQL | CLL, AML, NHL, HNSCC |
| 21 | TMEEMIFEV | CLL, Esophageal Cancer, Uterine Cancer, HNSCC |
| 24 | FLMEEVHMI | HNSCC |
| 25 | GLSETILAV | CLL, AML, NHL, HNSCC |
| 26 | KMLDEAVFQV | HNSCC |
| 27 | SLDIITITV | NHL |
| 28 | ILVSQLEQL | CLL, BRCA, NHL |
| 30 | KMLGLTVSL | RCC, Melanoma, AML, NHL |
| 32 | ALTSLELEL | HNSCC |
| 34 | LVFEGIMEV | CLL |
| 49 | RLALNTPKV | CLL, NHL |
| 58 | VLLNINGIDL | RCC, Melanoma, Uterine Cancer, NHL, HNSCC |
| 64 | VLFHQLQEI | CRC, CLL, AML, NHL |
| 68 | FLFPVYPLI | Uterine Cancer, AML, NHL, HNSCC |
| 69 | KLFDRSVDL | Uterine Cancer, AML |
| 72 | KAIGSLKEV | CRC, Esophageal Cancer, Uterine Cancer |
| 77 | AIIDGKIFCV | Uterine Cancer |
| 82 | ALSSVIKEL | NSCLC, CLL, BRCA, Melanoma, OC, Gallbladder Cancer, Bile Duct Cancer, AML, NHL, HNSCC |
| 83 | KLLEIDIDGV | Melanoma, AML, NHL, HNSCC |
| 84 | KMFENEFLL | CLL, NHL, HNSCC |
| 85 | FAYDGKDYLTL | CLL, Melanoma, Gallbladder Cancer, Bile Duct Cancer, AML |
| 86 | KVIDYVPGI | Melanoma, HNSCC |
| 87 | LLQNNLPAV | HNSCC |
| 89 | IQHDLIFSL | CLL, Melanoma, Urinary bladder cancer, AML |
| 91 | KLQDGVHII | CLL, Melanoma, AML, NHL |

TABLE 4B-continued

Peptides according to the present invention and their specific uses in other proliferative diseases, especially in other cancerous diseases (amendment of Table 4). This table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID No | Sequence | Additional Entities |
|---|---|---|
| 92 | YLQDYTDRV | CLL, NHL |
| 93 | ALRETVVEV | Melanoma, Uterine Cancer, AML, HNSCC |
| 94 | ALFPVAEDISL | RCC, CLL, BRCA, Melanoma, AML, NHL |
| 95 | ALYSKGILL | Gallbladder Cancer, Bile Duct Cancer, NHL |
| 96 | NLLKLIAEV | PC, AML, NHL |
| 97 | ALLDGTVFEI | BRCA, Uterine Cancer |
| 98 | ALVDHLNVGV | CLL |
| 99 | QMLEAIKALEV | Brain Cancer, CLL, NHL, HNSCC |
| 100 | VADPETRTV | Melanoma |
| 101 | AMNSQILEV | AML |
| 102 | ALFARPDLLLL | CLL |
| 105 | SMYDKVLML | Gallbladder Cancer, Bile Duct Cancer, AML, HNSCC |
| 107 | AMYGTKLETI | RCC, Esophageal Cancer, Gallbladder Cancer, Bile Duct Cancer, NHL |
| 108 | ILLDDQFQPKL | AML |
| 109 | SLFERLVVL | Uterine Cancer |
| 113 | LTDPDIHVL | RCC, CLL, BRCA, Melanoma, AML |
| 121 | YMLEHVITL | NSCLC, HCC, CLL, BRCA, Uterine Cancer, AML, NHL, HNSCC |
| 122 | SMMPDELLTSL | NHL |
| 124 | SLITDLQTI | AML, NHL |

NSCLC = non-small cell lung cancer, RCC = kidney cancer, CRC = colon or rectum cancer, GC = stomach cancer, HCC = liver cancer, PC = pancreatic cancer, PrC = prostate cancer, BRCA = breast cancer, OC = ovarian cancer, NHL = non-Hodgkin lymphoma, AML = acute myeloid leukemia, CLL = chronic lymphocytic leukemia, HNSCC = head and neck squamous cell carcinoma.

Thus, another aspect of the present invention relates to the use of at least one peptide according to the present invention according to any one of SEQ ID NO: 1, 15, 16, 17, 25, 27, 65, 67, 69, 76, 96, 107, and 110 for the—in one preferred embodiment combined—treatment of pancreatic cancer.

Thus, another aspect of the present invention relates to the use of at least one peptide according to the present invention according to any one of SEQ ID NO: 1, 8, 13, 14, 16, 17, 18, 20, 21, 25, 28, 30, 34, 38, 43, 47, 49, 52, 53, 59, 64, 73, 82, 83, 84, 85, 86, 87, 89, 91, 92, 93, 94, 96, 98, 99, 101, 102, 105, 108, 110, 111, 113, 112, 116, 121, 123, 124, and 126 for the—in one preferred embodiment combined—treatment of leukemia.

Thus, another aspect of the present invention relates to the use of at least one peptide according to the present invention according to any one of SEQ ID NO: 2, 12, 23, 25, 31, 32, and 98 for the—in one preferred embodiment combined—treatment of prostate cancer.

Thus, another aspect of the present invention relates to the use of at least one peptide according to the present invention according to any one of SEQ ID NO: 3, 6, 11, 15, 22, 25, 27, 31, 32, 33, 49, 69, 78, 79, 81, 86, 95, 96, 97, 98, 107, 109, 121, and 118 for the—in one preferred embodiment combined—treatment of liver cancer.

Thus, another aspect of the present invention relates to the use of at least one peptide according to the present invention according to any one of SEQ ID NO: 3, 8, 25 32, 57, 61, 67, 69, 72, 76, 81, 82, 83, 86, 87, 88, 90, 92, 93, 95, 97, 98, 102, 105, 107, 110, 119, 121, and 124 for the—in one preferred embodiment combined—treatment of ovarian cancer.

Thus, another aspect of the present invention relates to the use of at least one peptide according to the present invention according to any one of SEQ ID NO: 4, 7, 19, 21, 25, 31, 32, 34, 58, 61, 65, 68, 69, 72, 77, 78, 82, 83, 93, 96, 97, 98, 101, 106, 109, 118, 119, 121, and 124 for the—in one preferred embodiment combined—treatment of uterine cancer.

Thus, another aspect of the present invention relates to the use of at least one peptide according to the present invention according to any one of SEQ ID NO: 6, 20, 27, 77, and 89 for the—in one preferred embodiment combined—treatment of stomach cancer.

Thus, another aspect of the present invention relates to the use of at least one peptide according to the present invention according to any one of SEQ ID NO: 6, 20, 21, 24, 25, 26, 30, 45, 64, 68, 69, 72, 78, 82, 83, 84, 90, 95, 96, 99, 101, 107, 110, 121, and 124 for the—in one preferred embodiment combined—treatment of colon or rectum cancer.

Thus, another aspect of the present invention relates to the use of at least one peptide according to the present invention according to any one of SEQ ID NO: 6, 7, 9, 17, 19, 25, 26, 27, 28, 30, 31, 32, 65, 69, 79, 80, 82, 83, 84, 85, 86, 93, 94, 101, 103, 106, 121, 124, and 126 for the—in one preferred embodiment combined—treatment of breast cancer.

Thus, another aspect of the present invention relates to the use of at least one peptide according to the present invention according to any one of SEQ ID NO: 6, 9, 13, 15, 17, 20, 21, 23, 25, 26, 27, 34, 39, 45, 53, 58, 61, 66, 67, 68, 69, 77, 78, 80, 81, 82, 83, 84, 87, 88, 89, 93, 94, 95, 97, 99, 102, 103, 109, 121, 123, and 124 for the—in one preferred embodiment combined—treatment of urinary bladder cancer.

Thus, another aspect of the present invention relates to the use of at least one peptide according to the present invention according to any one of SEQ ID NO: 6, 11, 15, 21, 24, 25, 27, 28, 30, 32, 65, 66, 84, 85, 86, 87, 88, 91, 92, 93, 95, 96, 97, 98, 103, 105, 107, 110, 111, 118, and 121 for the—in one preferred embodiment combined—treatment of gallbladder cancer.

Thus, another aspect of the present invention relates to the use of at least one peptide according to the present invention according to any one of SEQ ID NO: 6, 11, 15, 21, 24, 25, 27, 28, 30, 32, 65, 66, 84, 85, 86, 87, 88, 91, 92, 93, 95, 96, 97, 98, 103, 105, 107, 110, 111, 118, and 121 for the—in one preferred embodiment combined—treatment of bile duct cancer.

Thus, another aspect of the present invention relates to the use of at least one peptide according to the present invention according to any one of SEQ ID NO: 4, 7, 15, 25, 26, 27, 29, 30, 31, 59, 61, 68, 69, 79, 80, 83, 86, 93, 96, 97, 98, 101, and 124 for the—in one preferred embodiment combined—treatment of brain cancer.

Thus, another aspect of the present invention relates to the use of at least one peptide according to the present invention according to any one of SEQ ID NO: 9, 24, 25, 26, 27, 33, 45, 65, 67, 69, 78, 79, 81, 82, 86, 91, 93, 94, 95, 110, 121, and 124 for the—in one preferred embodiment combined—treatment of NSCLC.

Thus, another aspect of the present invention relates to the use of at least one peptide according to the present invention according to any one of SEQ ID NO: 9, 80, 83, 95, 97, 105, 109, and 121 for the—in one preferred embodiment combined—treatment of Merkel cell carcinoma.

Thus, another aspect of the present invention relates to the use of at least one peptide according to the present invention according to any one of SEQ ID NO: 9, 21, 25, 33, 72, 79, 82, 85, 86, 93, 95, 107, and 110 for the—in one preferred embodiment combined—treatment of esophageal cancer.

Thus, another aspect of the present invention relates to the use of at least one peptide according to the present invention according to any one of SEQ ID NO: 17, 24, 25, 26, 27, 30, 37, 45, 58, 64, 68, 80, 81, 82, 83, 85, 86, 87, 89, 91, 93, 94, 96, 99, 100, 101, 102, 108, 113, and 121 for the—in one preferred embodiment combined—treatment of melanoma.

Thus, another aspect of the present invention relates to the use of at least one peptide according to the present invention according to any one of SEQ ID NO: 16, 20, 21, 24, 25, 26, 32, 58, 68, 82, 83, 84, 86, 87, 93, 99, 105, and 121 for the—in one preferred embodiment combined—treatment of head and neck squamous cell carcinoma.

Thus, another aspect of the present invention relates to the use of at least one peptide according to the present invention according to any one of SEQ ID NO: 14, 17, 20, 25, 27, 28, 30, 49, 58, 64, 68, 82, 83, 84, 91, 92, 94, 95, 96, 99, 107, 121, 122, and 124 for the—in one preferred embodiment combined—treatment of NHL.

Thus, another aspect of the present invention relates to the use of the peptides according to the present invention for the—preferably combined—treatment of a proliferative disease selected from the group of small cell lung cancer, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 126.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID NO: 1 to SEQ ID NO: 126, preferably containing SEQ ID NO: 1 to SEQ ID NO: 76, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are small cell lung cancer, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably small cell lung cancer cells.

The present invention further relates to biomarkers based on the peptides according to the present invention, herein called "targets", that can be used in the diagnosis of cancer, preferably small cell lung cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment. Both therapeutic and diagnostic uses against additional cancerous diseases are disclosed in the following more detailed description of the underlying expression products (polypeptides) of the peptides according to the invention.

ABCC5 is up-regulated in different cancer entities for example pancreatic cancer, in breast cancer metastasis compared to primary breast cancer and in esophageal cancer with an amplified region of chromosome 3q. ABCC5 is further frequently mutated in microsatellite instable (MSI) colorectal cancer (Mohelnikova-Duchonova et al., 2013; Chen et al., 2008; Alhopuro et al., 2012; Mourskaia et al., 2012). ABCC5 expression is influenced by the estrogen metabolism as well as elevated levels of HES1, DELTEX1 and c-Myc (Larson et al., 2009; Vendrell et al., 2004).

ABCF3 gene locus shows frequent chromosomal gains correlating with cervical cancer. Moreover, ABCF3 enhances proliferation of human liver cancer cells (Choi et al., 2007; Zhou et al., 2013b). ABCF3 binds to the tumor protein D52 family member TPD52L2 and positively regulates cell proliferation (Zhou et al., 2013b).

Deletion mapping of medulloblastoma tumors reveals loss of distal chromosome 17p13.3 sequences also in the ABR gene (McDonald et al., 1994).

AK3 is down-regulated in hepatocellular carcinomas and over-expressed in B-cell chronic lymphocytic leukemia (Carlucci et al., 2009; Melle et al., 2007).

AKAP11 is frequently altered and significantly over-expressed in oral tumors and further associated with cancer progression (Garnis et al., 2005). AKAP11 promotes cell migration in human cancer cells via suppression of GSK-3beta and interaction with cytoskeletal scaffolding proteins. AKAP11 contributes to alterations in cell cycle regulation by influencing the Rb pathway (Logue et al., 2011; Garnis et al., 2005).

The expression of ALG9 during TGFbeta-induced epithelial-to-mesenchymal transition (EMT) is significantly changed and influences the N-glycan profile of cancer cells (Tan et al., 2014).

AP3B1 is down-regulated in cervical tumors in comparison with normal tissue of the uterine cervix (Petrenko et al., 2006). AP3B1 is a target of the microRNA miR-9, which is de-regulated in many cancer types including hepatocellular and breast cancer (Zhang et al., 2015a; Selcuklu et al., 2012).

The expression of ARHGAP1 is altered in different cancer types including prostate and metastatic brain cancer (Davalieva et al., 2015; Zohrabian et al., 2007). ARHGAP1 down-regulation by miR-34a represses TGF-beta-induced tumor cell invasion. ARHGAP1 is associated with epithelial-to-mesenchymal transition (EMT) by restricting Rho activation which is necessary for detachment (Ahn et al., 2012; Clay and Halloran, 2013).

ATP13A3 expression is altered in cervical cancer (Bierkens et al., 2013).

ATP2C1 is over-expressed in cervical cancer via a common chromosomal gain of the locus. Loss of ATP2C1 in mice causes increased apoptosis and a genetic predisposition to squamous cell carcinomas of the skin and the esophagus in adult heterozygotes (Wilting et al., 2008; Okunade et al., 2007). ATP2C1 inhibition produces a pronounced alteration in the processing of the protein IGF1R, which is important for tumor progression (Grice et al., 2010).

BLOC1S1 is down-regulated in malignant prostate in comparison to normal prostate tissue (Asmann et al., 2002). BLOC1S1 is important for a proper EGFR lysosomal trafficking also via the interaction to its partners SNX2 and TSG101 (Zhang et al., 2014). C19orf40 (also called FAAP24) encodes a component of the Fanconi anemia (FA) core complex which plays a crucial role in DNA damage response (RefSeq, 2002). C19orf40 builds together with FANCM a complex important for DNA damage recognition, suppression of sister chromatid exchange as well as ATR-mediated checkpoint activation in DNA damage repair and replication to ensure chromosomal stability. Alterations of C19orf40 are associated with cancer-prone Fanconi anemia (Valeri et al., 2011; Wang et al., 2013d; Ciccia et al., 2007).

C2CD3 was shown to be associated with oropharyngeal squamous cell carcinomas (Wang et al., 2013b).

CAND1 is associated with prostate cancer and lung cancer (Zhai et al., 2014; Salon et al., 2007).

CASK is over-expressed in different cancer types including gastric and colorectal cancer as well as leukemia. Moreover, CASK is associated with cancer progression and poor prognosis (Wei et al., 2014; Zhou et al., 2014c; Al-Lamki et al., 2005). CASK is up-regulated via a PKA-dependent pathway by exendin-4 during the stimulation of beta-cell insulin secretion and by Necl-2 together with E-cadherin during wound healing processes (Giangreco et al., 2009; Zhu et al., 2014).

CASP8AP2 is de-regulated in different cancer types including down-regulation and hyper-methylation in acute lymphoblastic leukemia, hypo-methylation in early-stage liver cancer and frequent mutations in mismatch repair-deficient colorectal cancer (Park et al., 2002; Chen et al., 2012; Li et al., 2013; Juarez-Velazquez et al., 2014). CASP8AP2 is involved in the regulation of targets of the transcription factors NF-kappaB, c-Myb and Myc. Moreover, loss of function of CASP8AP2 induce the expression of the tumor suppressor gene NEFH (Hummon et al., 2012; Alm-Kristiansen et al., 2008).

CCNE2 is over-expressed in different cancer types including breast, lung, pancreatic and bladder cancer and can further be used as prognostic marker (Deng et al., 2013; Payton et al., 2002; Gudas et al., 1999; Chen et al., 2015a; Matsushita et al., 2015; Sieuwerts et al., 2006). CCNE2 is regulated by different factors including estrogen, PTEN and microRNAs. Moreover, elevated levels of CCNE2 lead to genomic instability with abnormal mitosis, micronuclei and chromosomal aberrations (Wu et al., 2009; Caldon et al., 2009; Caldon et al., 2013; Chen et al., 2015a).

CCT5 is associated with breast cancer (Campone et al., 2008). CCT5 was shown to be up-regulated in sinonasal adenocarcinoma (Tripodi et al., 2009). CCT5 is associated with overall survival in small cell lung cancer, drug resistance in gastric carcinoma and breast cancer and lymph node metastasis in esophageal squamous cell carcinoma (Niu et al., 2012; Ooe et al., 2007; Uchikado et al., 2006; Ludwig et al., 2002).

CDKAL1 is frequently amplified and over-expressed in bladder cancer and single nucleotide polymorphisms of CDKAL1 are associated with cancer risk, for example for colorectal cancer in men, in patients with diabetes (Sainz et al., 2012; Ma et al., 2014b; Hurst et al., 2008).

CES3 is often up-regulated in human colon tumor tissue with large interindividual variations (Sanghani et al., 2003).

CITED4 is down-regulated by promoter hyper-methylation in different cancer types including breast cancer and oligodendroglial tumors where it is associated with prognosis (Huang et al., 2011; Tews et al., 2007). CITED4 blocks the binding of hypoxia-inducible factor 1 alpha (HIF1alpha) to p300 and inhibits HIF1alpha transactivation and hypoxia-mediated gene activation (Huang et al., 2011; Fox et al., 2004).

COL6A3 encodes the alpha-3 chain of type VI collagen, a beaded filament collagen found in most connective tissues, playing an important role in the organization of matrix components (RefSeq, 2002). COL6A3 is alternatively spliced in colon, bladder and prostate cancer. The long isoform of COL6A3 is expressed almost exclusively in cancer samples and could potentially serve as a new cancer marker (Thorsen et al., 2008). COL6A3 is highly expressed in pancreatic ductal adenocarcinoma tissue and undergoes tumor-specific alternative splicing (Kang et al., 2014). COL6A3 has been demonstrated to correlate with high-grade ovarian cancer and contributes to cisplatin resistance. COL6A3 was observed to be frequently over-expressed in gastric cancer tissues (Xie et al., 2014). COL6A3 mutation(s) significantly predicted a better overall survival in patients with colorectal carcinoma independent of tumor differentiation and TNM staging (Yu et al., 2015b). COL6A3 expression was reported to be increased in pancreatic cancer, colon cancer, gastric cancer, mucoepidermoid carcinomas and ovarian cancer. Cancer associated transcript variants including exons 3, 4 and 6 were detected in colon cancer, bladder cancer, prostate cancer and pancreatic cancer (Arafat et al., 2011; Smith et al., 2009; Yang et al., 2007; Xie et al., 2014; Leivo et al., 2005; Sherman-Baust et al., 2003; Gardina et al., 2006; Thorsen et al., 2008). In ovarian cancer COL6A3 levels correlated with higher tumor grade and in pancreatic cancer COL6A3 was shown to represent a suitable diagnostic serum biomarker (Sherman-Baust et al., 2003; Kang et al., 2014).

CUL9-mediated degradation of cytochrome c is a strategy of cancer cells to prevent apoptosis during mitochondrial stress (Gama et al., 2014). The tumor suppressor CUL9 binds to p53 and promotes p53-mediated apoptosis. CUL9 also is a critical regulator in controlling the subcellular localization of p53 which is essential for its function. Depletion of CUL9 results in spontaneous tumor development (Pei et al., 2011; Nikolaev et al., 2003).

CXorf57 is a common viral integration site in ALV-induced B-cell lymphomas leading to a disruption of the normal gene transcription, suggesting that it could be a novel tumor suppressor (Justice et al., 2015).

Hypermethylation of CYP26B1 is a potential diagnosis marker in gastric cancer and CYB26B1 expression increases with malignancy in gliomas (Campos et al., 2011; Zheng et al., 2011). Clearance of the active metabolite all-trans-retinoic acid (atRA) by CYP26B1 influences regulation of differentiation, growth and migration of immune cells and is inhibited by TGF-beta, yet enhanced by TNF-alpha (Stevison et al., 2015).

DDX6 was found to be over-expressed in colorectal adenocarcinomas, gastric cancer, hepatocellular carcinoma, nodal marginal zone lymphoma, neuroblastoma, rhabdomyosarcoma and lung cancer cell lines (Akao et al., 1995; Nakagawa et al., 1999; Miyaji et al., 2003; Lin et al., 2008a; Stary et al., 2013; lio et al., 2013). In nodal marginal zone lymphoma, DDX6 seems to interfere with the expression of BCL6 and BCL2 in an NF-κB independent manner (Stary et al., 2013). Recent studies have shown that DDX6 post-transcriptionally down-regulated miR-143/145 expression by prompting the degradation of its host gene product, NCR143/145 RNA (Iio et al., 2013).

DGCR6 is de-regulated in metastatic breast cancer cells and a possible mediator of cell invasion (Euer et al., 2002).

DGCR6L regulates the migration of human gastric cancer cells via the formation of a PAK/DGCR6L/beta-actin complex (Li et al., 2010b).

DMXL2 was shown to be up-regulated in ER-alpha positive breast cancer (Faronato et al., 2015). DMXL2 is a functional biomarker for ER-alpha positive breast cancer (Faronato et al., 2015).

DNMT1 is associated with DNA methylation changes in cancer. Furthermore, DNMT1 is over-expressed in different cancer entities including colorectal, lung, pancreatic, prostate and liver cancer (Xu et al., 2010; He et al., 2011; Feng et al., 2014; Samaei et al., 2014; Bashtrykov and Jeltsch, 2015; Zhang et al., 2015d; Saito et al., 2003). DNMT1 stability is regulated via the Wnt-pathway, the II-6/JAK2/STAT3 signaling and pRB protein. Moreover, DNMT1 activity leads to epigenetic silencing of several tumor suppressor genes including p16INK, p53 and p21 by promoter hyper-methylation (Rhee et al., 2002; Shamma et al., 2013; Liu et al., 2015a; Song et al., 2015).

The DPYSL4 gene is localized to chromosome 10q25.2-q26 a region frequently mutated in glioblastomas and which contains many tumor suppressor genes (Honnorat et al., 1999). DPYSL4 is an apoptosis-inducible factor directly controlled by the tumor suppressor p53 in response to DNA damage (Kimura et al., 2011).

DYNC2H1 was shown to be up-regulated in glioblastoma multiforme (Yokota et al., 2006).

ECT2 is over-expressed as a result of tumor-specific gene amplifications in a variety of human tumors including lung, ovarian, gastric and pancreatic cancer. ECT2 is important for cell proliferation, migration, invasion and tumorigenicity (Fields and Justilien, 2010; Jin et al., 2014). Protein kinase C iota and ECT2 activate through MEK/ERK signaling a tumor-initiating cell phenotype in ovarian cancer (Wang et al., 2013c). Nuclear ECT2 is binding preferentially to the Rho GTPase Rac1 and leads through Rac1 activation to cellular transformation, while cytoplasmic ECT2 binds to the Rho GTPase RhoA and leads through RhoA activation to the formation of cytokinetic furrow (Su et al., 2011; Huff et al., 2013).

The increased expression of EFR3B is associated with the progression of squamous dysplasia of the esophageal mucosa (Joshi et al., 2006). The loss of EFR3B constitutes a rare copy number variation (CNV) detected in hereditary nonpolyposis colorectal cancer (Lynch syndrome) (Villacis et al., 2016).

EYA3 is highly expressed in Ewing sarcoma tumor samples and cell lines compared with mesenchymal stem cells. On the other hand, deletion of the EYA3 gene has been linked to certain pancreatic ductal adenocarcinomas (Gutierrez et al., 2011; Robin et al., 2012). Recent work has shown that over-expression of EYA3 results in increased proliferation, migration, invasion and transformation of breast cancer cells (Pandey et al., 2010).

FAM83F is up-regulated in esophageal squamous cell carcinomas. Moreover, FAM83F is a target of miR-143 which inhibits proliferation, migration and invasion. FAM83F contains as part of the family with sequence similarity 83 a highly conserved domain associated with driving cellular transformation (Cipriano et al., 2014; Mao et al., 2016).

Over-expression of FIG. 4 was found in the triple negative breast cancer compared to non-tumorigenic cells (Ikonomov et al., 2013).

FMNL2 is over-expressed in colorectal cancer, associated with invasion and migration and a target of different microRNAs (Zhu et al., 2008; Lu et al., 2015; Ren et al., 2016). FMNL2 activates the Rho/ROCK pathway, SRF transcription and actin assembly influencing cell invasion. Moreover, FMNL2 is involved in TGF-beta-induced epithelial-to-mesenchymal-transition and cell invasion via Smad3 and MAPK/MEK signaling. Furthermore, FMNL2 drives beta1-integrin internalization and thereby increases invasive motility (Li et al., 2010c; Wang et al., 2015c; Zeng et al., 2015).

FMO3 is differentially expressed when comparing tobacco-exposed lung tissue of smokers with non-smokers and with adenocarcinomas from smokers and may therefore be utilized to identify smokers with increased risk for lung cancer (Woenckhaus et al., 2006). FMO3 influences the efficacy and toxicity of different cancer drugs including daunorubicin, imatinib and sulindac (Thompson et al., 2014; Hisamuddin et al., 2005; Rochat et al., 2008). FMO3 activity can be influenced by nitric oxide donors and the recruitment of p53 to a p53 response element in the 5'-flanking region of the gene (Celius et al., 2010; Ryu et al., 2004).

FZD3 is up-regulated in different cancer types including colorectal, gastric and liver cancer as well as leukemia and is further associated with cancer progression (Wong et al., 2013; Lu et al., 2004; Bengochea et al., 2008). Binding of the ligand Wnt5a by the FZD3 receptor promotes the activation of PI3K and Akt (Kawasaki et al., 2007).

GALK2 was identified in an in-tumor genetic screen as a potential therapeutic target in ovarian carcinoma (Baratta et al., 2015). GALK2 is a kinase that is involved in the regulation of prostate cancer cell growth identified in an RNAi phenotypic screening (Whitworth et al., 2012).

GPR98 expression is increased in primary neuroendocrine tumors relative to normal tissue (Sherman et al., 2013). GPR98 was among the genes associated with survival of glioblastoma multiforme (Sadeque et al., 2012). GPR98 displays a transcript regulated by glucocorticoids which are used for the treatment of acute lymphoblastic leukemia as they lead to the induction of apoptosis (Rainer et al., 2012).

GTF3C5 is over-expressed in human ovarian carcinomas (Winter et al., 2000).

HELZ is down-regulated in different human cancer cells and located in a frequently lost chromosomal band in various human cancers. Moreover, HELZ plays a role in cancer cell growth (Nagai et al., 2003). HELZ is repressed by beta-catenin/TCF4 activity via different microRNAs in colorectal cancer cells. HELZ interacts directly with SMYD3, which is itself frequently over-expressed in human cancers, to activate transcription of oncogenes and is thereby contributing to carcinogenesis (Schepeler et al., 2012; Hamamoto et al., 2004).

HIF1A was shown to be associated with tumor necrosis in aggressive endometrial cancer. HIF1A was further described to be a potential target for the treatment of this disease (Bredholt et al., 2015). HIF1A was shown to be associated with hepatocarcinogenesis, sarcoma metastasis and nasopharyngeal carcinoma (Chen et al., 2014; El-Naggar et al., 2015; Li et al., 2015c). A single nucleotide polymorphism in HIF1A was shown to be significantly associated with clinical outcomes of aggressive hepatocellular carcinoma patients after surgery (Guo et al., 2015). Aberrant HIF1A activity together with aberrant STAT3 activity was shown to drive tumor progression in malignant peripheral nerve sheath tumor cell lines. Thus, inhibition of the STAT3/

HIF1A/VEGF-A signaling axis was described as a viable treatment strategy (Rad et al., 2015). HIF1A was described as an important target for hypoxia-driven drug resistance in multiple myeloma (Maiso et al., 2015). HIF1A was shown to be asymmetrical expressed in three different cell lines that correspond with the stages of multiple myeloma pathogenesis, suggesting that HIF1A is involved in the tumorigenesis and metastasis of multiple myeloma (Zhao et al., 2014a). The long noncoding HIF1A antisense RNA-2 was described as being up-regulated in non-papillary clear-cell renal carcinomas and gastric cancer and is associated with tumor cell proliferation and poor prognosis in gastric cancer (Chen et al., 2015d). De-regulation of the PI3K/AKT/mTOR pathway through HIF1A was described to be critical for quiescence, maintenance and survival of prostate cancer stem cells (Marhold et al., 2015). HIF1A was described as one gene of a 4-gene classifier which is prognostic for stage I lung adenocarcinoma (Okayama et al., 2014). A polymorphism of HIF1A was shown to be associated with increased susceptibility to digestive tract cancer in Asian populations (Xu et al., 2014b). HIF1A was described as a prognostic marker in sporadic male breast cancer (Deb et al., 2014).

HLA-E is over-expressed in different cancer entities including gastric, colorectal, lung and skin cancer and overexpression is associated with poor prognosis (Allard et al., 2011; Bossard et al., 2012; Ishigami et al., 2015; Talebian et al., 2016). HLA-E/NKG2A mediates resistance of tumor cells to natural killer (NK) cell mediated lysis (Enqvist et al., 2011; He et al., 2014; Talebian et al., 2016).

HTT is associated with cancer prognosis in different cancer types including breast and ovarian cancer at which wild-type HTT is down-regulated in metastatic breast cancer. Mutant HTT leads to cancer progression and metastasis and also the CAG repeat size seems to play a role for cancer prognosis (Moreira et al., 2013; Thion et al., 2015; Thion et al., 2016). p53 regulates the expression of HTT and the mutant HTT form modifies p53 and the p53-mediated signaling cascade leading to a slow accumulation of DNA damage (Illuzzi et al., 2011; Feng et al., 2006).

Down-regulation, promoter methylation and/or SNPs of IRAK3 in different cancer types including liver, prostate, pancreatic, breast and brain are associated with tumor progression and poor prognosis (Lee et al., 2009; Rajaraman et al., 2009; Caba et al., 2014; Jain et al., 2014; Kuo et al., 2015; Angulo et al., 2016). On one hand TGF-beta induces the IRAK3 expression in tumor-associated macrophages (TAMs) to circumvent the anti-tumor responses of macrophages by secreting IL-12, TNFalpha and IFN-gamma. On the other IRAK3 mediates a TLR7-induced MEKK3-dependent second wave of NF-kappaB activation to produce an immunosuppressive feedback (Standiford et al., 2011; Zhou et al., 2013a; Jain et al., 2014; del et al., 2005).

IRX1 is hyper-methylated and down-regulated in different cancer types including gastric, oral, head and neck and bladder cancer. It is further associated with cell growth and invasion (Marcinkiewicz and Gudas, 2014; Kitchen et al., 2016; Guo et al., 2010; Bennett et al., 2008b). IRX1 influences metastasis formation via BDKRB2/PAK1 and is involved in the TGFbeta signaling pathway (Jiang et al., 2011; Bennett et al., 2008b).

IRX2 is de-regulated in different cancer types including over-expression and gene amplification in sarcoma and breast cancer. On the other hand, hyper-methylation in lung cancer and loss of heterozygosity (LOH) in gastric cancer were further observed (Rauch et al., 2012; Kadota et al., 2009; Liu et al., 2014d; Yu et al., 2006; Adamowicz et al., 2006). IRX2 promotes the activation of the PI3K/Akt pathway as well as increased proliferation and invasion following the up-regulation of VEGF, MMP2 and MMP9 (Liu et al., 2014d; Liu et al., 2015c).

ITGB7 is over-expressed in different cancer types including leukemia, colorectal cancer and hepatoma cancer cells (Ortega et al., 2010; Riches et al., 2014; Liu et al., 2003; Chen et al., 1999). The oncogene c-Maf up-regulates ITGB7 and cyclin D2 leading to a malignant transformation of T-cell lymphoma cells (Morito et al., 2006).

It has been reported that the expression of ITPR1 is altered in tamoxifen resistance breast cancer cell lines (Elias et al., 2015). Researchers have postulated a role for the HIF2alpha/ITPR1 axis in regulating clear cell renal cell carcinomas cell survival. In addition, ITPR1 was significantly correlated with overall survival in breast cancer (Messai et al., 2014; Gu et al., 2016).

An unusual KCNN3 expression leads to plasma membrane hyperpolarization and enhanced cell motility of melanoma cells (Chantome et al., 2009). KCNN3 (also called TASK-1) expression was down-regulated by 17beta-estradiol in mouse neuroblastoma N2A cells and improved cell proliferation (Hao et al., 2014). KCNN3 expression was up-regulated by exposure of breast cancer organotypic culture to 1,25 dihydroxy vitamin D(3) in physiological and supra-physiological concentrations (Milani et al., 2013). KCNN3 (also called K2P3.1) together with K2P1.1 and K2P12.1, were over-expressed in a range of cancers examined using the online cancer microarray database, Oncomine (www.oncomine.org) (Williams et al., 2013).

KNTC1 is down-regulated in oral squamous cell carcinomas with higher tumor size correlating with poor prognosis. Furthermore, Frameshift mutations of KNTC1 were detected in gastric and colorectal cancer with microsatellite instability (Wang et al., 2004; Diniz et al., 2015; Kim et al., 2010).

Single nucleotide polymorphisms in the LIG3 gene modify the risk for different cancer types including lung, colorectal, esophageal and pancreatic cancer (Li et al., 2009; Corral et al., 2013; Hao et al., 2004; Landi et al., 2006). c-Myc plays a role in transcriptional activation of LIG3, leading to an increase in error-prone repair in leukemia (Muvarak et al., 2015).

A single nucleotide polymorphism in LILRA4 influences the prognosis of patients with chronic lymphocytic leukemia with regard to their response to chemotherapy and overall survival (Sellick et al., 2008). PDCs expressing LILRA4 can activate an immune-receptor tyrosine-based activation motif (ITAM)-mediated signaling pathway and interact with bone marrow stromal cell antigen 2 to assure an appropriate TLR response. by PDCs during viral infections and likely participates in PDC tumor crosstalk. Immunoglobulin-like transcript 7 ligands inhibit PDCs production of type I IFNs and ILT7/ILT7L interaction may therefore present a negative feedback following viral infection and a mechanism for the impairment of PDCs in the cancer microenvironment (Tsukamoto et al., 2009; Palma et al., 2012).

LNX2 is de-regulated in different cancer types including a detection of a genetic variant in diffuse large B-cell lymphoma and gene amplification with over-expression in colorectal carcinomas (Kumar et al., 2011; Camps et al., 2013). LNX2 increases Notch levels and up-regulates the transcription factor TCF7L2 and thereby activates Wnt signaling (Camps et al., 2013).

LOXL4 is de-regulated in different cancer types including down-regulation in liver cancer associated with poor prognosis and hyper-methylation followed by down-regulation in bladder cancer. On the other hand, over-expression in colorectal and head and neck cancer as well as up-regulation in gastric cancer associated with tumor progression, metastasis and poor prognosis were observed (Kim et al., 2009; Li et al., 2015a; Tian et al., 2015; Gorogh et al., 2016; Wu et al., 2007). TGF-beta1 induces LOXL4 following inhibition of the Ras/ERK signaling, suppression of MMP2 activity and activation of the FAK/Src pathway (Li et al., 2015a; Wu et al., 2007; Kim et al., 2008).

LPPR4 shows an aberrant DNA methylation pattern in pediatric B-cell acute lymphoblastic leukemia (Wong et al., 2012; Figueroa et al., 2013).

Over-expression of MADD has been found in many types of human tumors, including non-small cell lung cancer, lung adenocarcinoma, squamous cell carcinoma, thyroid cancer, breast cancer and ovarian cancer (Subramanian et al., 2009; Li et al., 2011a; Wei et al., 2012; Bi et al., 2013; Turner et al., 2013). Researchers have demonstrated that elevated levels of MADD in the A549 cells inhibited apoptosis and increased survival, while knock-down of MADD promoted apoptosis and reduced cell proliferation (Wei et al., 2012; Bi et al., 2013). Additionally, MADD function is regulated by PTEN-PI3K-Akt signaling pathway (Jayarama et al., 2014).

MANEAL is a cancer-related gene with aberrant methylation for example in breast cancer cells, dependent on their estrogen and progesterone status (Li et al., 2010a; Liu et al., 2011).

MB21D2 is mutated in small cell lung cancer (Peifer et al., 2012).

MCM2 has been shown to be the most sensitive marker of proliferation and prognosis in early breast cancer, renal cell carcinomas, esophageal and laryngeal squamous cell carcinoma and oligodendroglioma of the brain (Wharton et al., 2001; Going et al., 2002; Rodins et al., 2002; Gonzalez et al., 2003; Cai et al., 2012; Joshi et al., 2015).

MDN1 was described to be a candidate tumor suppressor gene, mutated in breast cancers of the luminal B type (Cornen et al., 2014).

MED13 is frequently amplified in breast cancer where an over-expression is associated with poor prognosis. Moreover, frameshift mutations in MED13 are described for colorectal and gastric cancer with microsatellite instability (Monni et al., 2001; Broude et al., 2015; Jo et al., 2016). MED13 physically links the CDK8 oncogene to the mediator complex and thereby influences the function in signal-dependent gene regulation (Davis et al., 2013; Clark et al., 2015).

MEX3A is over-expressed and the gene is amplified in Wilms tumors associated with a late relapse (Krepischi et al., 2016). MEX3A regulates CDX2 via a post-transcriptional mechanism with impact in intestinal differentiation, polarity and stemness, contributing to intestinal homeostasis and carcinogenesis (Pereira et al., 2013).

MRS2 promotes cell growth, down-regulates p27 and up-regulates cyclin D1 in multidrug-resistant gastric cancer cells (Chen et al., 2009).

MTO1 is up-regulated in breast cancer cells and the expression level inversely correlates with promoter methylation status (Kim et al., 2013).

MYB can be converted into an oncogenic transforming protein through a few mutations (Zhou and Ness, 2011). MYB is known as oncogene and is associated with apoptosis, cell cycle control, cell growth/angiogenesis and cell adhesion by regulating expression of key target genes such as cyclooxygenase-2, Bcl-2, BclX(L) and c-Myc (Ramsay et al., 2003; Stenman et al., 2010). The oncogenic fusion protein MYB-NFIB and MYB over-expression are found in adenoid cystic carcinoma of the salivary gland and breast, pediatric diffuse gliomas, acute myeloid leukemia and pancreatic cancer (Wallrapp et al., 1999; Pattabiraman and Gonda, 2013; Nobusawa et al., 2014; Chae et al., 2015; Marchio et al., 2010). By the synergy between MYB and beta-Catenin during Wnt signaling, MYB is associated with colon tumorigenesis (Burgess et al., 2011). Since MYB is a direct target of estrogen signaling anti-MYB therapy is considered for ER-positive breast tumors (Gonda et al., 2008).

The MZT1 gene is located in a chromosomal region with a putative breast cancer susceptibility gene and a common site for somatic deletions in a variety of malignant tumors (Rozenblum et al., 2002).

NAV1 is significantly hypomethylated in ER+/PR+ breast cancers and frequently mutated in neuroblastoma (Li et al., 2010a; Lasorsa et al., 2016).

NBEA is one of the common fragile site genes inactivated in different cancers including myelomas and oropharyngeal squamous cell carcinomas. NBEA shows frequent mutations with prognostic relevance in gastric cancer (Li et al., 2016; O'Neal et al., 2009; Nagoshi et al., 2012; Gao et al., 2014; McAvoy et al., 2007).

NCOA1 is frequently overexpressed and further associated with cancer progression and prognosis in different cancer types including breast, prostate and head and neck cancer (Qin et al., 2011; Qin et al., 2014; Pavon et al., 2016; Luef et al., 2016). NCOA1 promotes breast cancer metastasis by enhancing CSF1 promoter activity via an AP1 binding site and upregulation of ITGA5 expression (Qin et al., 2011; Qin et al., 2014).

NR2C2 is associated with invasion and metastasis in different cancer types including prostate and lung cancer (Ding et al., 2015; Qiu et al., 2015; Zhang et al., 2015b). NR2C2 influences carcinogenesis via cross-talk with other nuclear receptor pathways like PPARgamma and RAR and increases invasion and metastasis through activation of the TGFbetaR2/p-Smad3 signaling (Liu et al., 2014c; Qiu et al., 2015; Lee et al., 2004).

NUP155 was described as a potential epigenetic bio-marker of white blood cell's DNA which is associated with breast cancer predisposition (Khakpour et al., 2015). NUP155 was described as strictly required for the proliferation and survival of NUP214-ABL1-positive T-cell acute lymphoblastic leukemia cells and thus constitutes a potential drug target in this disease (De et al., 2014).

siRNAs targeting MAPK inhibit cervical cancer cell line growth and lead to a down-regulation of NUP188 (Huang et al., 2008; Yuan et al., 2010). NUP188 seems to be a target of the tumor suppressor gene BRCA1 in breast cancer (Bennett et al., 2008a). NUP188 is required for the chromosome alignment in mitosis through K-fiber formation and recruitment of NUMA to the spindle poles (Itoh et al., 2013).

OLFM1 is deregulated in different cancer types including endometrial cancer and lung adenocarcinomas (Wu et al., 2010; Wong et al., 2007). Up-regulation of the OLFM1 gene suppresses the activities of extracellular inhibitors of the Wnt signaling pathway and this may promote cell proliferation (Tong et al., 2014).

Elevated levels of PI4KA were observed in hepatocellular carcinoma versus normal liver tissue. In addition, the PI4KA gene was detected in pancreatic cancer cell line (Ishikawa et al., 2003; Ilboudo et al., 2014). Patients suffering from hepatocellular carcinoma with higher PI4KA mRNA concentrations had a higher risk of tumor recurrence as well as shorter disease-specific survival (Ilboudo et al., 2014). Recently, PI4KA has been identified to be involved in cell proliferation and resistance to cisplatin treatment in a medulloblastoma cell line. Others have revealed that PI4KA plays a crucial role in invasion and metastasis in pancreatic cancer (Ishikawa et al., 2003; Guerreiro et al., 2011).

POLA1 is up-regulated in tumors and high-grade intra-epithelial lesions of the uterine cervix (Arvanitis and Spandidos, 2008). Increased SIX1 expression up-regulates POLA1 and promotes the proliferation and growth of cervical cancer. Moreover, the tumor suppressor microRNA miR-206 regulates POLA1 expression in lung cancer cells (Liu et al., 2014b; Cui et al., 2013).

POLD2 amplification and RPA3 deletion on 7p are correlated with DNA stability and a longer survival of patients of ovarian cancer (Sankaranarayanan et al., 2015). The expression of POLD2 and 6 other landscape genes of a network model is associated with the duration of survival for patients with glioblastomas (Bredel et al., 2009).

PPP4C is over-expressed in different cancer types such as colorectal and pancreatic cancer and is further associated with invasion, metastasis and poor prognosis (Weng et al., 2012; Li et al., 2015b). Inhibition of the MEK/ERK pathway activates PPP4C as part of PP4 and enhances NF-kappaB signaling via inactivation of the IKK complex whereas phosphorylated Akt is required for PPP4C-mediated up-regulation of MMP-2 and MMP-9 (Brechmann et al., 2012; Li et al., 2015b; Yeh et al., 2004).

PTRH2 is de-regulated in different cancer types including down-regulation in lung and breast cancer associated with metastasis and up-regulation in esophageal squamous cell carcinomas and ovarian adenocarcinomas associated with tumor progression (Karmali et al., 2011; Kim et al., 1998; Hua et al., 2013; Fan et al., 2014; Yao et al., 2014). Down-regulation of PTRH2 mediated by E2 binding to ERalpha is accomplished mainly through the PI3K/Akt pathway and leads to an anti-anoikis effect (Zheng et al., 2014a).

Plk1 phosphorylates RACGAP1 during cytokinesis to create a binding site for Ect2 leading to an activation of the Rho/ERK signaling axis which can promote metastasis (Kim et al., 2014; Chen et al., 2015b). RACGAP1 is over-expressed in different cancer entities including colorectal, breast, liver and lung cancer. RACGAP1 is further associated with progression and poor prognosis in breast and hepatocellular carcinoma (Wang et al., 2011; Pliarchopoulou et al., 2013; Liang et al., 2013; Imaoka et al., 2015).

Four variants of RACGAP1P were detectable in 16 families densely affected by colorectal cancer (DeRycke et al., 2013).

RGS12 is de-regulated in different cancer types. A single nucleotide polymorphism (SNP) in the RGS12 gene is associated with overall survival in late-stage non-small lung cancer and a nonsense-mediated decay (NMD)-resistant frameshift mutation is further associated with microsatellite instability (MSI) high colorectal cancer (Williams et al., 2010; Dai et al., 2011; Potocnik et al., 2003). Gbetagamma is acting via PI3-kinase gamma and cSrc to activate the tyrosine phosphorylation of Galphai1/2/3 and subsequent association with RGS12 resulting in a rapid deactivation of Gaplphai (Huang et al., 2014).

Single nucleotide polymorphisms in RTEL1 are associated with a risk for brain tumors, such as gliomas. The RTEL1 locus is frequently amplified in multiple human cancers including hepatocellular carcinomas and gastrointestinal tract tumors (Wu et al., 2012; Zhao et al., 2014b; Adel et al., 2015). RTEL1 antagonizes homologous recombination by promoting the disassembly of D loop recombination intermediates in an ATP-dependent reaction to eliminate inappropriate recombination events and thereby ensures maintenance of genomic integrity (Barber et al., 2008).

SENP1 expression is up-regulated in different cancer types including prostate, liver and lung cancer and is further associated with cancer progression and cell proliferation (Bawa-Khalfe et al., 2010; Wang et al., 2013a; Burdelski et al., 2015; Zhang et al., 2016). HGF/c-Met and IL-6 induce SENP1 leading to activation of NFkappaB signaling and epithelial-to-mesenchymal transition (EMT) subsequently resulting in cell proliferation and migration (Xu et al., 2015; Zhang et al., 2016).

SETDB2 is frequently deleted or down-regulated in different cancer types including deletions in breast cancer associated with poor prognosis, frameshift mutations in colorectal cancer and deletions of the chromosomal region in chronic lymphocytic leukemia associated with cancer progression (Mabuchi et al., 2001; Parker et al., 2011; Choi et al., 2014; Liu et al., 2015b).

SIPA1 L3 is differentially expressed between normal breast epithelium and ductal carcinoma in situ and may be associated with regulation of cell proliferation (Abba et al., 2004).

An NHE (Na—H exchange) inhibition suppresses the proliferation of gastric cancer cells via up-regulation of p21 through a SLC4A8-induced reduction of chloride concentration without changes in pH (Hosogi et al., 2012).

The biotin uptake of SLC5A6 in cancer cells, such as human breast cancer cells, is higher than in normal cells possibly for maintaining the high proliferative status and thus provides a chance for an anti-cancer drug delivery system (Vadlapudi et al., 2013).

SLCO2A1 is de-regulated in different cancer types including a down-regulation in head and neck squamous cell carcinomas and colorectal cancer and an over-expression in pancreatic and liver cancer (Wlcek et al., 2011; Zolk et al., 2013; Hays et al., 2013; Shang et al., 2015). SLCO2A1 as part of the Cox-2/PGE2 pathway affects especially the PGE2 secretion which plays a role in tumorigenesis of colorectal cancer cells. SLCO2A1 further mediates the invasion and apoptosis of lung cancer cells via the PI3K/Akt/mTOR pathway (Greenhough et al., 2009; Zhu et al., 2015; Kasai et al., 2016).

SLIT1 is hyper-methylated and down-regulated in different cancer types including cervical, brain, gastric, colorectal and hepatocellular cancer (Zheng et al., 2009; Ghoshal et al., 2010; Kim et al., 2016; Dickinson et al., 2004; Narayan et al., 2006). SLIT1 is a target of the DNA methyltransferase DNMT3B resulting in promoter hyper-methylation. SLIT1 is also a target of the WNT/beta-catenin signaling pathway (Ghoshal et al., 2010; Katoh and Katoh, 2005).

SLIT2 is down-regulated in different tumor entities including breast and renal cancer and it has been described as tumor suppressor. On the other hand, also over-expression of SLIT2 in different cancer types including skin and gastric cancer and an association with cancer progression was found. Thus, effects of the SLIT2/Robo1 signaling axis on tumor growth and metastasis seem to be dependent on the cellular context (Alvarez et al., 2013; Shi et al., 2013; Ma et al., 2014c; Qi et al., 2014; Yuan et al., 2016; Prasad et al., 2008). Activation of the SLIT2/Robo1 signaling axis promotes tumorigenesis through activation of Src signaling, down-regulation of E-cadherin and induction of the Wnt/beta-catenin pathway. Moreover, the tumor-suppressive effects seem to be mediated by the regulation of the beta-catenin and PI3K signaling pathways resulting in an enhanced beta-catenin/E-cadherin-mediated cell-cell adhesion (Zhang et al., 2015c; Prasad et al., 2008).

SPC25, together with CDCA1, KNTC2 and APC24, is over-expressed in colorectal and gastric cancers when compared to normal mucosae (Kaneko et al., 2009).

STAT4 is de-regulated in different cancer types including a down-regulation in hepatocellular carcinomas and lymphomas associated with poor prognosis and an over-expression in colorectal and gastric cancer linked with invasion (Zhou et al., 2014b; Litvinov et al., 2014; Wang et al., 2015a; Cheng et al., 2015). The induction of cytotoxic CD4+ T cells via up-regulation of the JAK2/STAT4/perforin pathway can inhibit tumor cell growth (Zhou et al., 2014a).

STK33 is de-regulated in different cancer types including over-expression in hypopharyngeal and liver cancer as well as an association with cancer progression and hyper-methylation in colorectal cancer (Moon et al., 2014; Yang et al., 2016; Huang et al., 2015b). STK33 can promote cell migration, invasion and epithelial-to-mesenchymal transition (EMT) via suppressing of p53, caspase-3 and E-cadherin (Huang et al., 2015b; Wang et al., 2015b).

TAT is down-regulated, hyper-methylated and located at a frequently deleted region in hepatocellular carcinomas and shows tumor suppressive ability associated with its pro-apoptotic role in a mitochondrial-dependent manner by promoting cytochrome-c release and activating caspase-9 and PARP (Fu et al., 2010).

Some researchers have reported over-expression of TIMELESS protein and mRNA in hepatocellular carcinoma as well as in colorectal cancer, cervical cancer, lung cancer and prostate cancer. On the other hand, another study reported down-regulation of TIMELESS in hepatocellular carcinomas. In addition, single nucleotide polymorphism in the TIMELESS gene were not associated with risk of prostate cancer but correlated with breast cancer risk (Lin et al., 2008b; Fu et al., 2012; Mazzoccoli et al., 2011; Yoshida et al., 2013; Mao et al., 2013; Markt et al., 2015; Elgohary et al., 2015). In lung cancer, elevated levels of TIMELESS were associated with poor overall survival (Yoshida et al., 2013).

TIPARP is frequently amplified during oral squamous cell carcinoma progression and the gene lies on a locus associated with susceptibility for ovarian cancer (Goode et al., 2010; Cha et al., 2011).

TLX3 expression associated with T-cell acute lymphoblastic leukemia is mediated by genomic rearrangements, but its prognostic relevance is under discussion (Ballerini et al., 2008; Ma et al., 2014a; Su et al., 2004). Other genetic lesions that are detectable in TLX3 rearranged T-ALL cases are deletion of WT1 and FBXW7, an U3-ubiquitin ligase mediating the degradation of Notch1, Myc, Jun and Cyclin E (Van et al., 2008). TMEM44 encodes a multi-transmembrane protein enriched in the bottom portion of taste buds and associated with developmentally immature taste cells (Moyer et al., 2009).

TNFRSF6B is over-expressed in different cancer types including breast, cervical, bladder, gastric and liver cancer and is further associated with tumor progression (Yang et al., 2010; Lin and Hsieh, 2011; Jiang et al., 2014; Zheng et al., 2014b; Jiang et al., 2016). Down-regulation of TNFRSF6B induces Fas-ligand-mediated apoptosis by the activation of FADD, caspase-3, -8, -9 and additionally reduces ERK1/2 phosphorylation (Zhou et al., 2013c; Zhang et al., 2015e; Hu et al., 2016).

TOP2A was shown to be up-regulated in adenosquamous carcinoma of the pancreas (Borazanci et al., 2015). TOP2A was described as commonly altered at both gene copy number and gene expression level in cancer cells, and may play a critical role in chromosome instability in human cancers (Chen et al., 2015c). Alongside with other genes, TOP2A was shown to be genomically and molecularly aberrated in malignant peripheral nerve sheath tumors and exhibits great promise as a personalized therapeutic target (Yang and Du, 2013). TOP2A was described as a de-regulated gene in malignant pleural mesothelioma which may also be associated with resistance to cisplatin (Melaiu et al., 2012). TOP2A was described as an oncogene whose amplification is related to a significant response to anthracycline-based chemotherapy in breast cancer (Zhang and Yu, 2011). TOP2A deletions and amplifications were described to be prevalent in HER-2 amplified and primary breast tumors and associated with poor prognosis (Pritchard et al., 2008; Jarvinen and Liu, 2003). TOP2A gene copy numbers were also shown to be elevated in a mismatch repair-proficient colorectal cancer subgroup compared to a mismatch repair-deficient subgroup, which may provide a survival advantage selectively in mismatch repair-proficient tumors (Sonderstrup et al., 2015). TOP2A was described as a potential target for well differentiated and de-differentiated liposarcoma (Crago and Singer, 2011). TOP2A expression in non-small cell lung cancer was shown to be associated with tumor histological type and inversely correlated with 2-year brain metastases free survival (Huang et al., 2015a). TOP2A was shown to be associated with increased risk of developing brain metastases in non-small cell lung cancer (Huang et al., 2015a). TOP2A expression was shown to be associated with lower overall and disease-free survival in patients with endometrial cancer who received adjuvant taxane-platinum regimens after surgery (Ito et al., 2016). TOP2A was shown to promote prostate cancer aggressiveness by inducing chromosomal rearrangements of genes that contribute to a more invasive phenotype (Schaefer-Klein et al., 2015). TOP2A was shown to be related with the androgen receptor signaling pathway in a way that contributes to prostate cancer progression and confers sensitivity to treatments (Schaefer-Klein et al., 2015).

TUBGCP2 was shown to be up-regulated in a taxol-resistant ovarian cancer cell line and was described to be associated with the sensitization of the non-small cell lung carcinoma cell line NCI-H1155 to taxol (Huang and Chao, 2015). TUBGCP2 was shown to be up-regulated in glioblastoma, where its over-expression antagonized the inhibitory effect of the CDK5 regulatory subunit-associated tumor suppressor protein 3 on DNA damage G2/M checkpoint activity (Draberova et al., 2015).

TXNIP is a tumor suppressor gene which is down-regulated and hyper-methylated in various cancer entities including breast, lung, stomach and colorectal cancer. It is further associated with tumor progression and prognosis (Zhou et al., 2011; Zhou and Chng, 2013; Le et al., 2006). TXNIP increases the production of ROS and oxidative stress resulting in cell apoptosis and TXNIP cross-talk with many intracellular signaling pathways including the cellular glucose uptake as well as c-Myc, p53, HER-2 and p38MAPK/ERK (Zhou and Chng, 2013; Suh et al., 2013; Li et al., 2014; Nie et al., 2015; Shen et al., 2015; Hong and Hagen, 2015).

UPF1 is part of the nonsense-mediated mRNA decay (NMD) machinery and may have a functional role in prostate cancer progression and metastasis (Yang et al., 2013). Further the UPF1 RNA surveillance gene is commonly mutated in pancreatic adenosquamous carcinoma (Liu et al., 2014a).

USP1 is over-expressed in different cancer types including cervical, lung and gastric cancer, melanoma and sarcoma (Williams et al., 2011; Garcia-Santisteban et al., 2013; Jung et al., 2016). PDGF signaling up-regulates USP1 which de-ubiquitinates and thereby stabilizes the inhibitor of DNA-binding (ID) proteins that are essential factors for proliferation and cancer progression. The same pathway is potentially also involved in the control of chromosome duplication (Wrighton, 2011; Mistry et al., 2013; Jung et al., 2016; Rahme et al., 2016).

A de-regulated expression of UTY is associated with different cancer types including head and neck, prostate and nasal cancer (Dasari et al., 2001; Lau and Zhang, 2000; Sethi et al., 2009; Llorente et al., 2008). UTY catalyzes the de-methylation of H3K27 peptides and may thereby work as transcriptional repressor (Walport et al., 2014).

Over-expression of VCP in different cancer types including breast, lung, liver, prostate and colorectal cancer is associated with tumor progression and poor prognosis (Valle et al., 2011; Yamamoto et al., 2003; Cui et al., 2015; Yamamoto et al., 2004; Tsujimoto et al., 2004). The Aurora-B and the Akt kinase can phosphorylate VCP which can then directly regulate his downstream targets like p53 and NF-kappaB and thereby influence cell proliferation and survival (Valle et al., 2011; He et al., 2015; Vandermoere et al., 2006; Braun and Zischka, 2008).

WDFY3 was shown to be down-regulated in colorectal cancer (Piepoli et al., 2012).

WDR36 is a target of several cancer-related microRNAs in colorectal cancer (Li et al., 2011b). Loos of WDR36 function leads to an activation of the p53 stress-response pathway, up-regulation of mRNA for Bax, p53 and CDNK1A and further causes apoptotic cell death (Gallenberger et al., 2011; Skarie and Link, 2008).

WDR7 expression is de-regulated by copy number alterations in gastric cancer and shows an elevated expression in numerous malignant cell lines (Junnila et al., 2010; Sanders et al., 2000).

Genome-wide association studies identified gene polymorphisms in XXYLT1. It has been proposed that these polymorphisms are susceptibility loci for non-small cell lung cancer development (Zhang et al., 2012).

ZFYVE16 is a phosphorylation target of EGF signaling and can interact with Smad2 to facilitate TGF-beta signaling thereby playing an important role in the regulation of cell growth and proliferation of cancer cells (Chen et al., 2007b; Chen et al., 2007a).

SUMO modification potentiates the negative effect of ZNF131 on estrogen signaling and consequently attenuates estrogen-induced cell growth in breast cancer cells (Oh and Chung, 2012).

Changes in ZNF292 were described as chronic lymphocytic leukemia driver alterations (Puente et al., 2015). ZNF292 was described as a tumor-suppressor gene in colorectal cancer (Takeda et al., 2015). ZNF292 was described as an immunogenic antigen with clinical relevance in head and neck squamous cell carcinoma (Heubeck et al., 2013).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (elongated variants of the peptides of the invention) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 126 or a variant thereof which is 88% homologous to SEQ ID NO: 1 to SEQ ID NO: 126, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 126. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 126, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 1, 3, and 8

| Position | 1 | 2 | 3 | 4 | 5 | 6 | 7 | 8 | 9 | 10 | 11 | 12 |
|---|---|---|---|---|---|---|---|---|---|---|---|---|
| SEQ ID No 1 | A | M | L | E | E | V | N | Y | I | | | |
| Variants | | L | | | | | | | V | | | |
| | | L | | | | | | | | | | |
| | | L | | | | | | | L | | | |
| | | L | | | | | | | A | | | |
| | | L | | | | | | | V | | | |
| | | | | | | | | | L | | | |
| | | | | | | | | | A | | | |
| | | A | | | | | | | V | | | |
| | | A | | | | | | | | | | |
| | | A | | | | | | | L | | | |
| | | A | | | | | | | A | | | |
| | | V | | | | | | | V | | | |
| | | V | | | | | | | | | | |
| | | V | | | | | | | L | | | |
| | | V | | | | | | | A | | | |
| | | T | | | | | | | V | | | |
| | | T | | | | | | | | | | |
| | | T | | | | | | | L | | | |
| | | T | | | | | | | A | | | |
| | | Q | | | | | | | V | | | |
| | | Q | | | | | | | | | | |
| | | Q | | | | | | | A | | | |
| | | Q | | | | | | | V | | | |

| Position | 1 | 2 | 3 | 4 | 5 | 6 | 7 | 8 | 9 | 10 | 11 | 12 |
|---|---|---|---|---|---|---|---|---|---|---|---|---|
| SEQ ID No 3 | V | L | A | E | I | D | P | K | Q | L | V | |
| Variants | | | | | | | | | | | I | |
| | | | | | | | | | | | L | |
| | | | | | | | | | | | A | |
| | | M | | | | | | | | | | |
| | | M | | | | | | | | | I | |
| | | M | | | | | | | | | L | |
| | | M | | | | | | | | | A | |
| | | A | | | | | | | | | | |
| | | A | | | | | | | | | I | |
| | | A | | | | | | | | | L | |
| | | A | | | | | | | | | A | |
| | | V | | | | | | | | | | |
| | | V | | | | | | | | | I | |
| | | V | | | | | | | | | L | |
| | | V | | | | | | | | | A | |
| | | T | | | | | | | | | | |
| | | T | | | | | | | | | I | |
| | | T | | | | | | | | | L | |
| | | T | | | | | | | | | A | |
| | | Q | | | | | | | | | | |
| | | Q | | | | | | | | | I | |
| | | Q | | | | | | | | | L | |
| | | Q | | | | | | | | | A | |

| Position | 1 | 2 | 3 | 4 | 5 | 6 | 7 | 8 | 9 | 10 | 11 | 12 |
|---|---|---|---|---|---|---|---|---|---|---|---|---|
| SEQ ID No 8 | V | L | I | D | D | S | Q | S | I | I | F | I |
| Variants | | | | | | | | | | | | V |
| | | | | | | | | | | | | L |
| | | | | | | | | | | | | A |
| | | | | | | | | | | | | V |
| | | M | | | | | | | | | | |
| | | M | | | | | | | | | | L |
| | | M | | | | | | | | | | A |
| | | M | | | | | | | | | | V |
| | | A | | | | | | | | | | |
| | | A | | | | | | | | | | L |
| | | A | | | | | | | | | | A |
| | | A | | | | | | | | | | V |
| | | V | | | | | | | | | | |
| | | V | | | | | | | | | | L |
| | | V | | | | | | | | | | A |

TABLE 6-continued

Variants and motif of the peptides according to SEQ ID NO: 1, 3, and 8

| | |
|---|---|
| V | V |
| T | |
| T | L |
| T | A |
| T | V |
| Q | |
| Q | L |
| Q | A |
| Q | V |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |

| C-terminus | N-terminus |
|---|---|
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 126.

"Consisting essentially of" shall mean that a peptide according to the present invention, in addition to the sequence according to any of SEQ ID NO: 1 to SEQ ID NO 126 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —$CH_2$—NH, —$CH_2$S—, —$CH_2CH_2$—, —CH=CH—, —$COCH_2$—, —CH(OH)$CH_2$—, and —$CH_2$SO—. U.S. Pat. No. 4,897,445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of $NaCNBH_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Another embodiment of the present invention relates to a non-naturally occurring peptide wherein said peptide consists or consists essentially of an amino acid sequence according to SEQ ID No: 1 to SEQ ID No: 141 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, KCl, KBr, KNOB, $KClO_4$, KI, KSCN, $Na_3PO_4$, $Na_2HPO_4$, $NaH_2PO_4$, $Na_2SO_4$, $NaCH_3COO$, NaCl, NaBr, NaNO$_3$, NaClO$_4$, NaI, NaSCN, ZnCl$_2$ Cs$_3$PO$_4$, Cs$_2$HPO$_4$, CsH$_2$PO$_4$, Cs$_2$SO$_4$, CsCH$_3$COO, CsCl, CsBr, CsNO$_3$, CsClO$_4$, CsI, CsSCN, Li$_3$PO$_4$, Li$_2$HPO$_4$, LiH$_2$PO$_4$, Li$_2$SO$_4$, LiCH$_3$COO, LiCl, LiBr, LiNO$_3$, LiClO$_4$, LiI, LiSCN, Cu$_2$SO$_4$, Mg$_3$(PO$_4$)$_2$, Mg$_2$HPO$_4$, Mg(H$_2$PO$_4$)$_2$, Mg$_2$SO$_4$, Mg(CH$_3$COO)$_2$, MgCl$_2$, MgBr$_2$, Mg(NO$_3$)$_2$, Mg(ClO$_4$)$_2$, MgI$_2$, Mg(SCN)$_2$, MnCl$_2$, Ca$_3$(PO$_4$), Ca$_2$HPO$_4$, Ca(H$_2$PO$_4$)$_2$, CaSO$_4$, Ca(CH$_3$COO)$_2$, CaCl$_2$), CaBr$_2$, Ca(NO$_3$)$_2$, Ca(ClO$_4$)$_2$, CaI$_2$, Ca(SCN)$_2$, Ba$_3$(PO$_4$)$_2$, Ba$_2$HPO$_4$, Ba(H$_2$PO$_4$)$_2$, BaSO$_4$, Ba(CH$_3$COO)$_2$, BaCl$_2$, BaBr$_2$, Ba(NO$_3$)$_2$, Ba(ClO$_4$)$_2$, BaI$_2$, and Ba(SCN)$_2$. Particularly preferred are NH acetate, MgCl$_2$, KH$_2$PO$_4$, Na$_2$SO$_4$, KCl, NaCl, and CaCl$_2$), such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1, FIGS. 1A-1P).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from small cell lung cancer samples (N=19 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 14 small cell lung cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from small cell lung cancer tissue samples were purified and HLA-associated peptides were isolated and analyzed by LC-MS (see examples). All TUMAPs contained in the present application were identified with this approach on primary small cell lung cancer samples confirming their presentation on primary small cell lung cancer.

TUMAPs identified on multiple small cell lung cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Besides over-presentation of the peptide, mRNA expression of the underlying gene was tested. mRNA data were obtained via RNASeq analyses of normal tissues and cancer tissues (cf. Example 2, FIGS. 3A and 3B). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

The present invention provides peptides that are useful in treating cancers/tumors, preferably small cell lung cancer that over- or exclusively present the peptides of the invention. These peptides were shown by mass spectrometry to be naturally presented by HLA molecules on primary human small cell lung cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy lung cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from small cell lung cancer, but not on normal tissues (see Example 1).

HLA-bound peptides can be recognized by the immune system, specifically T lymphocytes. T cells can destroy the cells presenting the recognized HLA/peptide complex, e.g. small cell lung cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according to the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus.

The recombinant viruses are generated and then tested for functionality, such as antigen specificity and functional avidity. An aliquot of the final product is then used to transduce the target T-cell population (generally purified from patient PBMCs), which is expanded before infusion into the patient. In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed. In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID NO: 1 to SEQ ID NO: 126, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL (SEQ ID NO: 144), or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 126, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 126, or a variant thereof which is at least 88% homologous (preferably identical) to SEQ ID NO: 1 to SEQ ID NO: 126 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 126 or a variant thereof which is at least 88% homologous (preferably identical) to SEQ ID NO: 1 to SEQ ID NO: 126, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 126.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of small cell lung cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 126 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are small cell lung cancer cells or other solid or hematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The present invention further relates to particular marker proteins and biomarkers based on the peptides according to the present invention, herein called "targets" that can be used in the diagnosis and/or prognosis of small cell lung cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a small cell lung cancer marker (poly)peptide, delivery of a toxin to a small cell lung cancer cell expressing a cancer marker gene at an increased level, and/or inhibiting the activity of a small cell lung cancer marker polypeptide) according to the invention.

Whenever possible, the antibodies of the invention may be purchased from commercial sources. The antibodies of the invention may also be generated using well-known methods. The skilled artisan will understand that either full length small cell lung cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 126 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the small cell lung cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain.

Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating small cell lung cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×100.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 126, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 126.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from small cell lung cancer, the medicament of the invention is preferably used to treat small cell lung cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of small cell lung cancer patients with various HLA-A HLA-B and HLA-C alleles. It may contain MHC class I and MHC class II peptides or elongated MHC class I peptides. In addition to the tumor associated peptides collected from several small cell lung cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, small cell lung cancer samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (small cell lung cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from small cell lung cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO.

The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from small cell lung cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for small cell lung cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

FIGS. 1A to 1E show the over-presentation of various peptides in normal tissues (white bars) and small cell lung cancer (black bars). FIG. 1A) CCNE2, Peptide: AMLEEVNYI (SEQ ID NO: 1)—Tissues from left to right: 2 adipose tissues, 3 adrenal glands, 4 blood cells, 10 blood vessels, 6 bone marrows, 7 brains, 5 breasts, 2 cartilages, 3 gallbladders, 5 hearts, 14 kidneys, 19 large intestines, 20 livers, 45 lungs, 4 lymph nodes, 7 nerves, 3 ovaries, 10 pancreas, 1 peritoneum, 5 pituitary glands, 6 placentas, 3 pleuras, 3 prostates, 7 salivary glands, 5 skeletal muscles, 6 skins, 3 small intestines, 4 spleens, 5 stomachs, 6 testis, 3 thymi, 3 thyroid glands, 9 tracheas, 2 ureters, 6 urinary bladders, 2 uteri, 6 esophagi, 19 SCLC cancer samples. The peptide has additionally been detected on 2/17 chronic lymphocytic leukemias, 1/20 pancreatic cancer cell lines, 1/27 colorectal cancer, 4/16 Non-Hodgkin lymphomas, 3/19 pancreatic cancers. FIG. 1B) IFT81, Peptide: VLAEIDP-KQLV (SEQ ID NO: 3)—Tissues from left to right: 2 adipose tissues, 3 adrenal glands, 4 blood cells, 10 blood vessels, 6 bone marrows, 7 brains, 5 breasts, 2 cartilages, 3 gallbladders, 5 hearts, 14 kidneys, 19 large intestines, 20 livers, 45 lungs, 4 lymph nodes, 7 nerves, 3 ovaries, 10 pancreas, 1 peritoneum, 5 pituitary glands, 6 placentas, 3 pleuras, 3 prostates, 7 salivary glands, 5 skeletal muscles, 6 skins, 3 small intestines, 4 spleens, 5 stomachs, 6 testis, 3 thymi, 3 thyroid glands, 9 tracheas, 2 ureters, 6 urinary bladders, 2 uteri, 6 esophagi, 19 SCLC cancer samples. The peptide has additionally been detected on 2/16 liver cancers, 2/20 ovarian cancers, 1/20 esophageal cancer. FIG. 1C) POLA1, Peptide: GLDPTQFRV (SEQ ID NO: 39) Tissues from left to right: 2 adipose tissues, 3 adrenal glands, 4 blood cells, 10 blood vessels, 6 bone marrows, 7 brains, 6 breasts, 2 cartilages, 1 eye, 3 gallbladders, 5 hearts, 14 kidneys, 19 large intestines, 20 livers, 45 lungs, 4 lymph nodes, 7 nerves, 3 ovaries, 10 pancreases, 1 peritoneum, 5 pituitary glands, 6 placentas, 3 pleuras, 3 prostates, 7 salivary glands, 5 skeletal muscles, 6 skins, 3 small intestines, 4 spleens, 5 stomachs, 6 testis, 3 thymi, 3 thyroid glands, 9 tracheas, 3 ureters, 6 urinary bladders, 2 uteri, 6 esophagi, 19 SCLC cancer samples. The peptide has additionally been detected on 1/20 pancreatic cancer cell line, 1/16 Non-Hodgkin lymphoma, 1/20 ovarian cancer, 1/20 urinary bladder cancer. FIG. 1D) LOXL4, Peptide: GLLEVQVEV (SEQ ID NO: 40)—Tissues from left to right: 2 adipose tissues, 3 adrenal glands, 4 blood cells, 10 blood vessels, 6 bone marrows, 7 brains, 6 breasts, 2 cartilages, 1 eye, 3 gallbladders, 5 hearts, 14 kidneys, 19 large intestines, 20 livers, 45 lungs, 4 lymph nodes, 7 nerves, 3 ovaries, 10 pancreases, 1 peritoneum, 5 pituitary glands, 6 placentas, 3 pleuras, 3 prostates, 7 salivary glands, 5 skeletal muscles, 6 skins, 3 small intestines, 4 spleens, 5 stomachs, 6 testis, 3 thymi, 3 thyroid glands, 9 tracheas, 3 ureters, 6 urinary bladders, 2 uteri, 6 esophagi, 19 SCLC cancer samples. The peptide has additionally been detected on 1/20 pancreatic cancer cell line, 1/20 ovarian cancer. FIG. 1E) USP1, Peptide: SLQSLIISV (SEQ ID NO: 5)—Samples from left to right: 3 cell-lines (1 blood, 1 pancreatic), 2 normal tissues (1 lymph node, 1 spleen), 24 cancer tissues (2 leukocytic leukemia cancers, 1 breast cancer, 1 gallbladder cancer, 5 lung cancers, 6 lymph node cancers, 2 ovarian cancers, 2 prostate cancers, 2 skin cancers, 1 urinary bladder cancer, 2 uterine cancers). FIGS. 1F to P show the over-presentation of various peptides in normal tissues (white bars) and cancer (black bars). FIG. 1F) Gene Symbol: GPR98, Peptide: GLLGDIAIHL (SEQ ID NO.: 7)—Tissues from left to right: 1 cell line (blood cells), 2 normal tissues (1 brain, 1 pituitary gland), 35 cancer tissues (27 brain cancers, 1 breast cancer, 1 liver cancer, 4 lung cancers, 2 uterus cancers). FIG. 1G) Gene Symbol: ITPR1, Peptide: ILIETKLVL (SEQ ID NO.: 14)—Tissues from left to right: 2 cell lines (1 prostate, 1 skin), 2 normal tissues (1 lymph node, 1 spleen), 26 cancer tissues (11 leukocytic leukemia cancers, 1 kidney cancer, 6 lung cancers, 4 lymph node cancers, 1 ovarian cancer, 1 prostate cancer, 1 stomach cancer, 1 testis cancer). FIG. 1H) Gene Symbol: ATP2C1, Peptide: GLYSKTSQSV (SEQ ID NO.: 33)—Tissues from left to right: 2 cell lines (1 blood cells, 1 pancreas), 4 normal tissues (1 adrenal gland, 1 colon, 2 lungs), 41 cancer tissues (1 leukocytic leukemia cancer, 2 breast cancers, 3 esophageal cancers, 5 head-and-neck cancers, 1 colon cancer, 1 liver cancer, 14 lung cancers, 3 lymph node cancers, 5 ovarian cancers, 1 prostate cancer, 3 urinary bladder cancers, 2 uterus cancers). FIG. 1I) Gene Symbol: NEDD1, Peptide: SLSGEIILHSV (SEQ ID NO.: 45)—Tissues from left to right: 3 cell lines (2 pancreases, 1 skin), 14 cancer tissues (2 breast cancers, 3 head-and-neck cancers, 1 colon cancer, 5 lung cancers, 1 skin cancer, 2 urinary bladder cancers). FIG. 1J) Gene Symbol: SLC4A8, Peptide: VLLSGLTEV (SEQ ID NO.: 59)—Tissues from left to right: 8 cancer tissues (1 leukocytic leukemia cancer, 4 brain cancers, 2 lung cancers, 1 rectum cancer). FIG. 1K) Gene Symbol: ECT2, Peptide: KAIGSLKEV (SEQ ID NO.: 72)—Tissues from left to right: 1 cell line (1 pancreas), 12 cancer tissues (1 esophageal cancer, 1 colon cancer, 1 rectum cancer, 5 lung cancers, 2 ovarian cancers, 1 stomach cancer, 1 uterus cancer). FIG. 1L) Gene Symbol: XXYLT1, Peptide: RLLEPAQVQQL (SEQ ID NO.: 79)—Tissues from left to right: 4 cell lines (1 blood cells, 2 pancreases, 1 skin), 2 normal tissues (1 colon, 1 spleen), 29 cancer tissues (2 brain cancers, 1 breast cancer, 2 esophageal cancers, 1 head-and-neck cancer, 1 rectum cancer, 1 liver cancer, 8 lung cancers, 4 lymph node cancers, 4 ovarian cancers, 1 skin cancer, 2 urinary bladder cancers, 2 uterus cancers). FIG. 1M) Gene Symbol: TSEN34, Peptide: LLAEIGAVTLV (SEQ ID NO.: 81)—Tissues from left to right: 8 cell lines (5 blood cells, 1 pancreas, 2 skin), 30 cancer tissues (1 bile duct cancer, 1 myeloid cells cancer, 1 leukocytic leukemia cancer, 2 breast cancers, 2 head-and-neck cancers, 1 colon cancer, 2 liver cancers, 11 lung cancers, 1 lymph node cancer, 3 ovarian cancers, 1 prostate cancer, 2 skin cancers, 2 urinary bladder cancers). FIG. 1N) Gene Symbol: MCM2, Peptide: FLPEAPAEL (SEQ ID NO.: 111)—Tissues from left to right: 5 cell lines (5 blood cells), 19 cancer tissues (5 leukocytic leukemia cancers, 1 myeloid cells cancer, 1 bone marrow cancer, 1 gallbladder cancer, 1 lung cancer, 8 lymph node cancers, 1 stomach cancer, 1 uterus cancer). FIG. 1O) Gene Symbol: LIG3, Peptide: LLLPGVIKTV (SEQ ID NO.: 112)—Tissues from left to right: 1 cell line (1 blood cells), 10 cancer tissues (1 leukocytic leukemia cancer, 1 colon cancer, 4 lung cancers, 3 ovarian cancers, 1 urinary bladder cancer). FIG. 1P) Gene Symbol: STK33, Peptide: SLIDDNNEINL (SEQ ID NO.: 119)—Tissues from left to right: 3 cell lines (3 blood cells), 1 normal tissue (1 trachea), 13 cancer tissues (3 brain cancers, 2 lung cancers, 2 lymph node cancers, 3 ovarian cancers, 1 prostate cancer, 2 uterus cancers).

FIGS. 2A to 2D show exemplary expression profiles of source genes of the present invention that are highly overexpressed or exclusively expressed in small cell lung cancer in a panel of normal tissues (white bars) and 10 small cell lung cancer samples (black bars). FIG. 2A. Genesymbol: MEX3A; FIG. 2B Genesymbol: ECT2; FIG. 2C: Genesymbol: CCNE2; FIG. 2D: Genesymbol: TIMELESS.

(FIG. 3A): Gene symbol: SLIT1, SLIT2, Peptide: SLYDNQITTV (SEQ ID NO: 130); (FIG. 3B): Gene symbol: TLX3, Peptide: SLAPAGVIRV (SEQ ID NO: 128).

EXAMPLES

Example 1

Figure 1A:
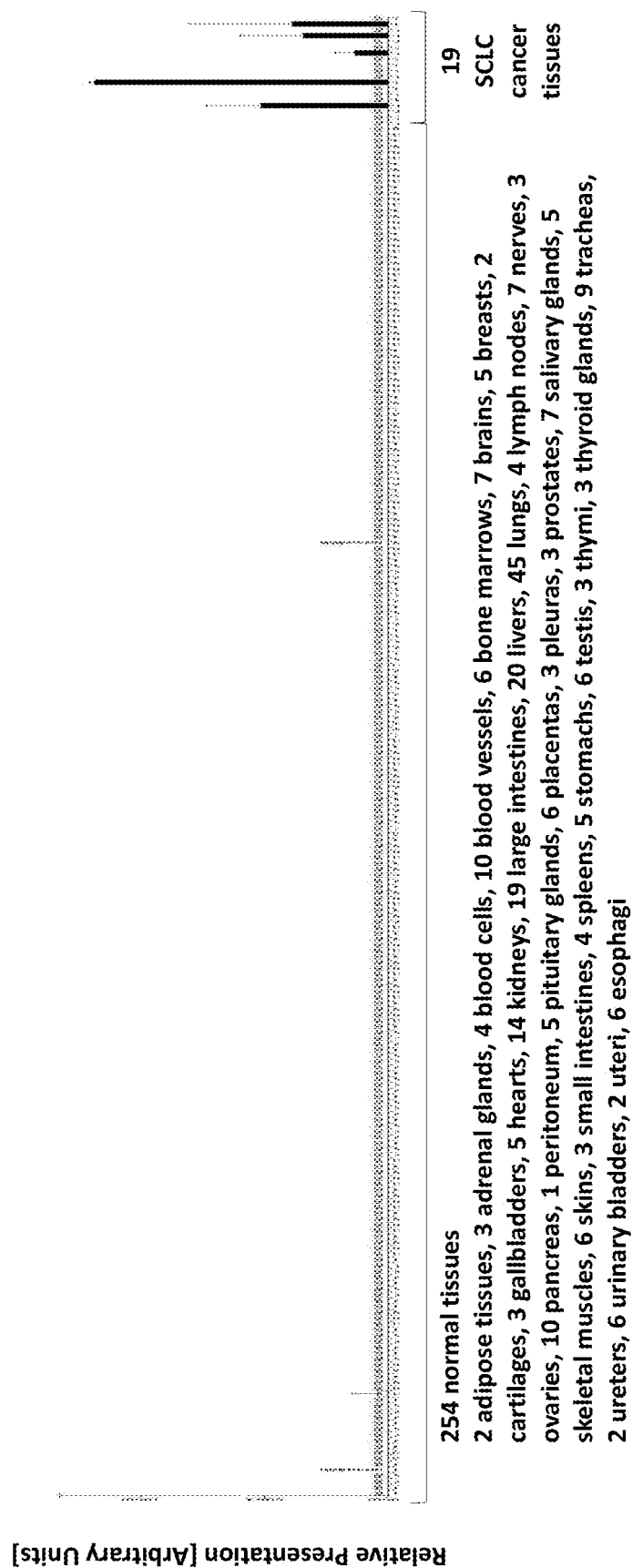
FIGS. 1A to 1P show the over-presentation of various peptides in normal tissues (white bars) and cancer (black bars).
Figure 1B:
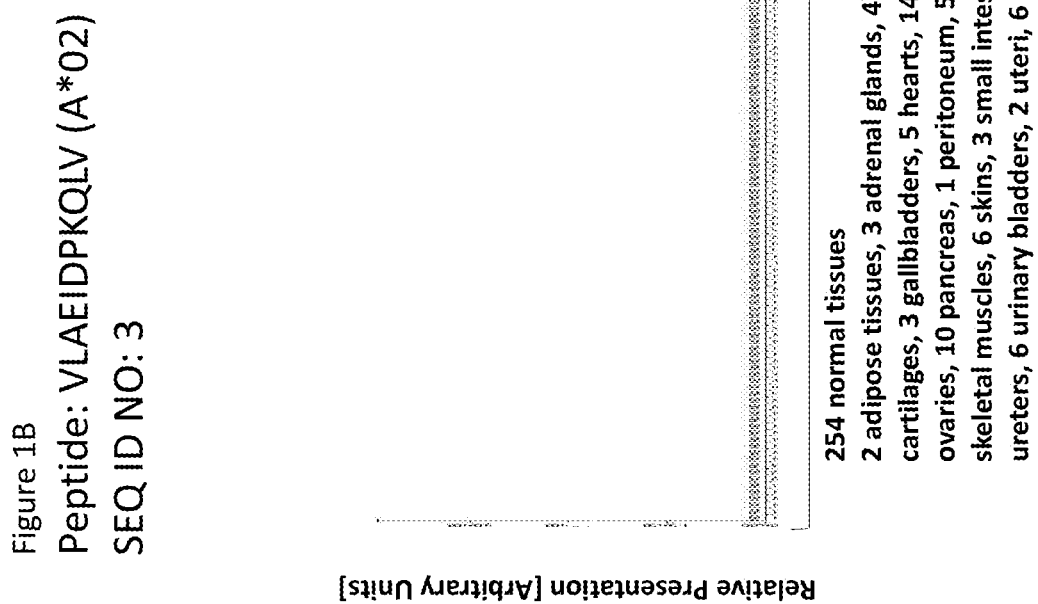
Figure 1D:
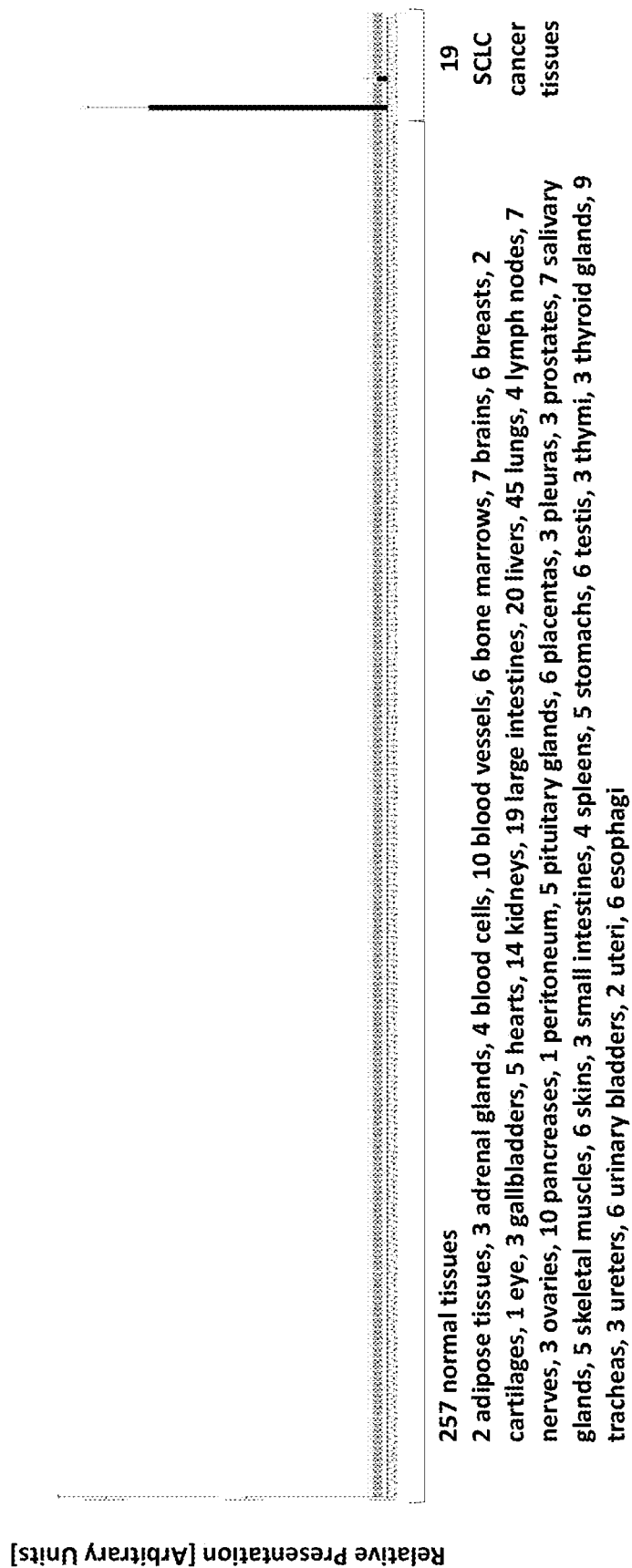
Figure 1E:
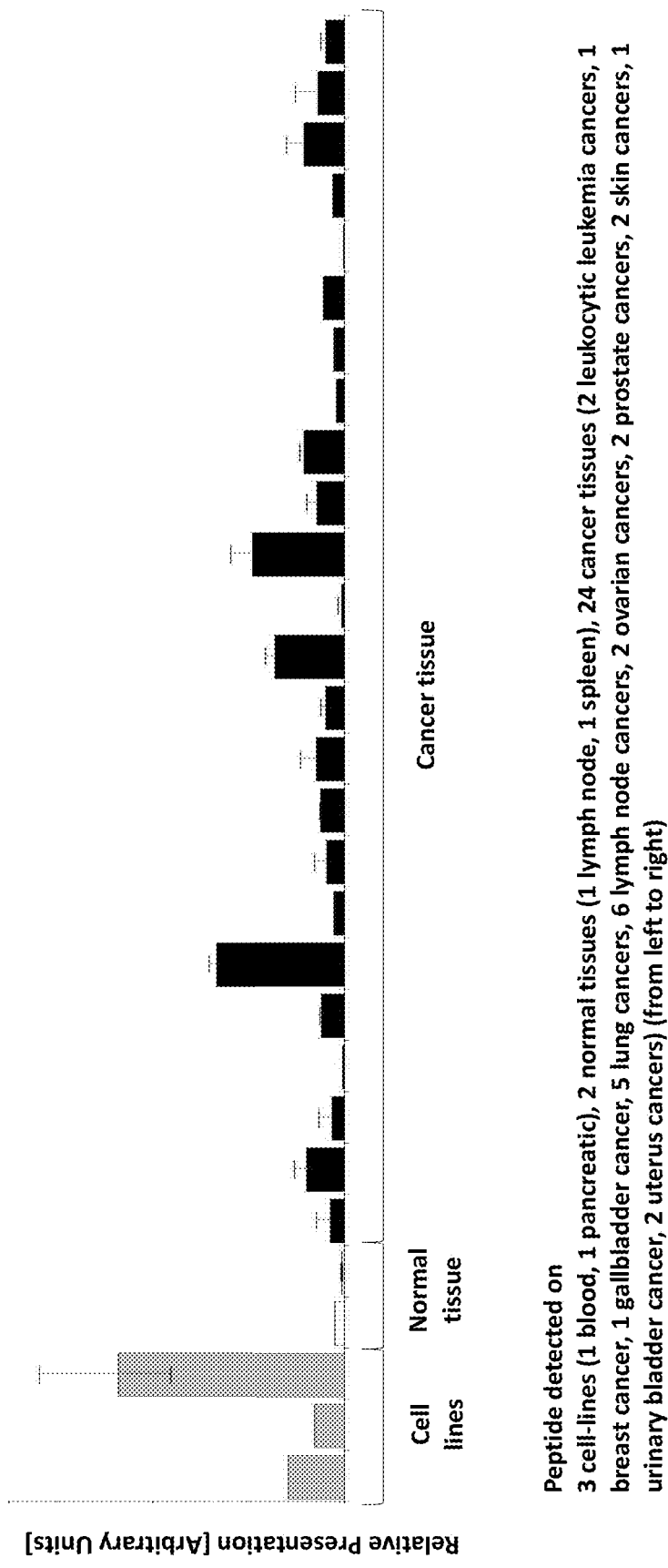
Figure 1F:
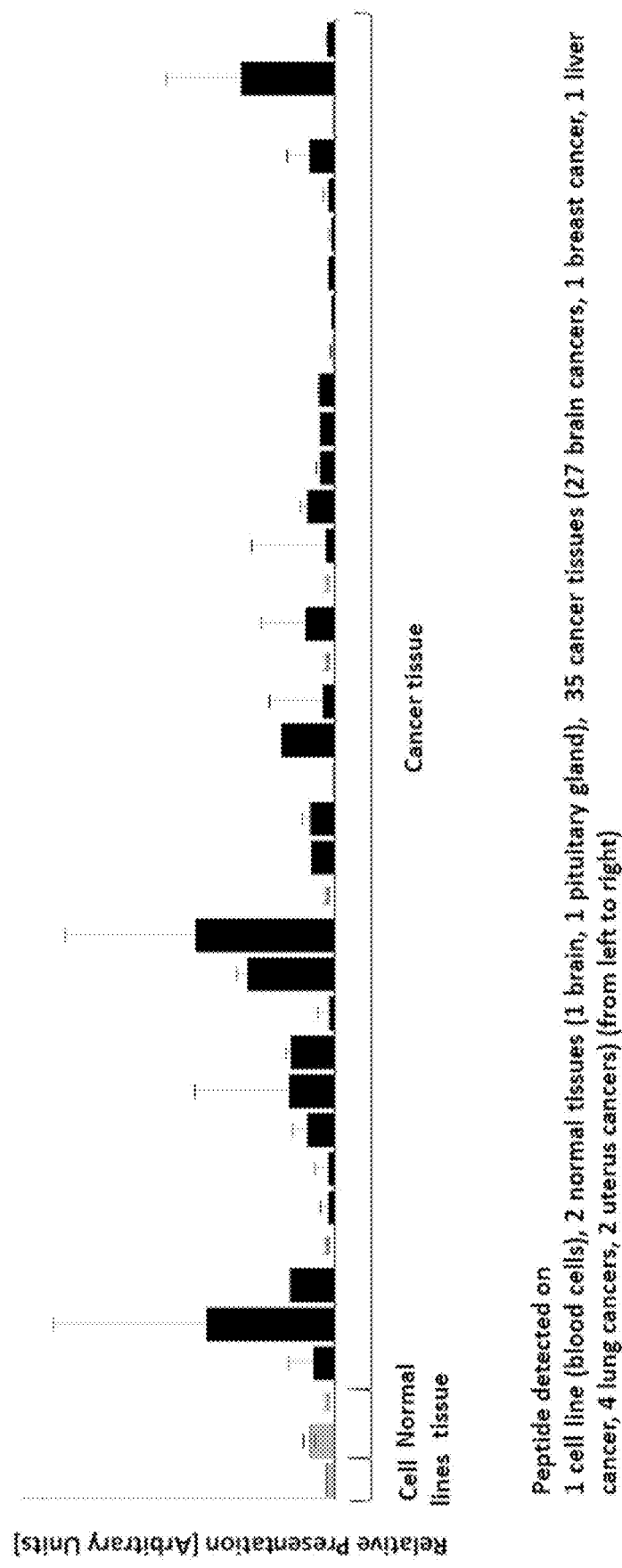
Figure 1H:
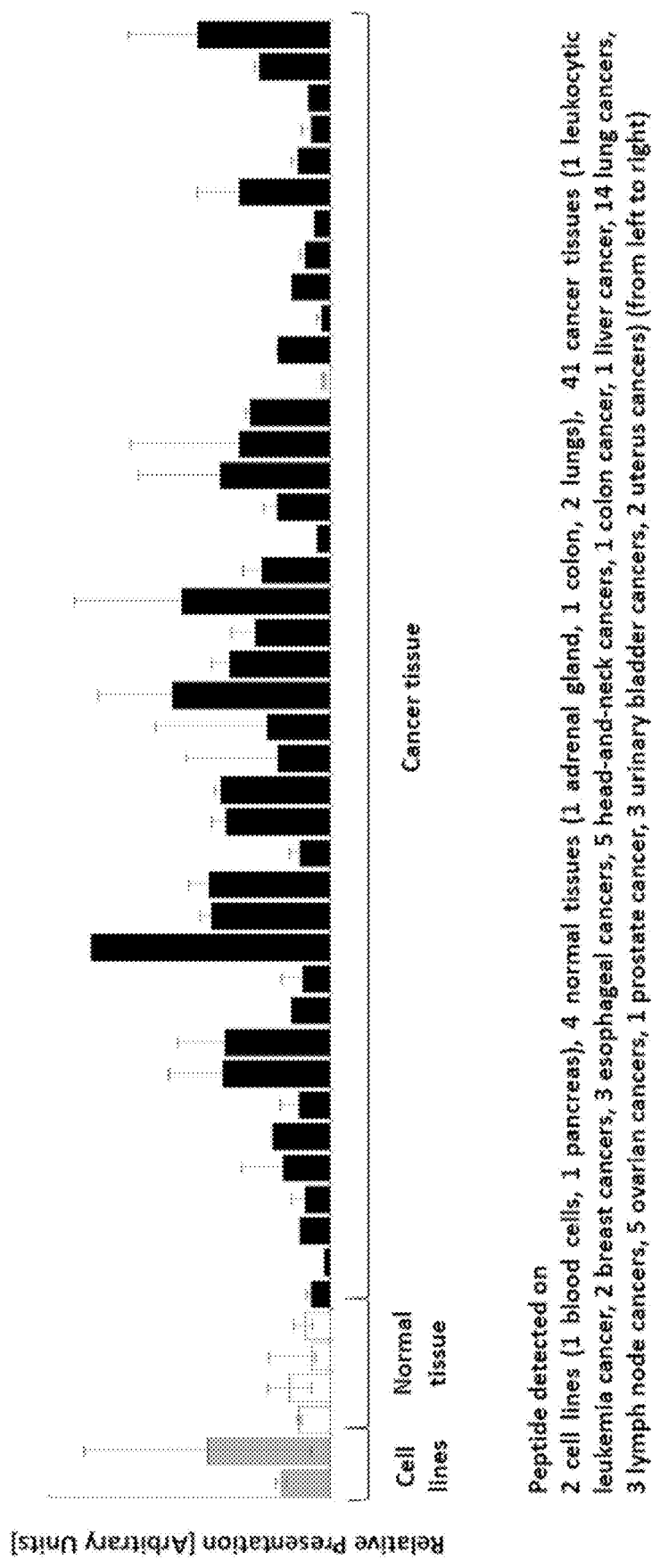
Figure 1J:
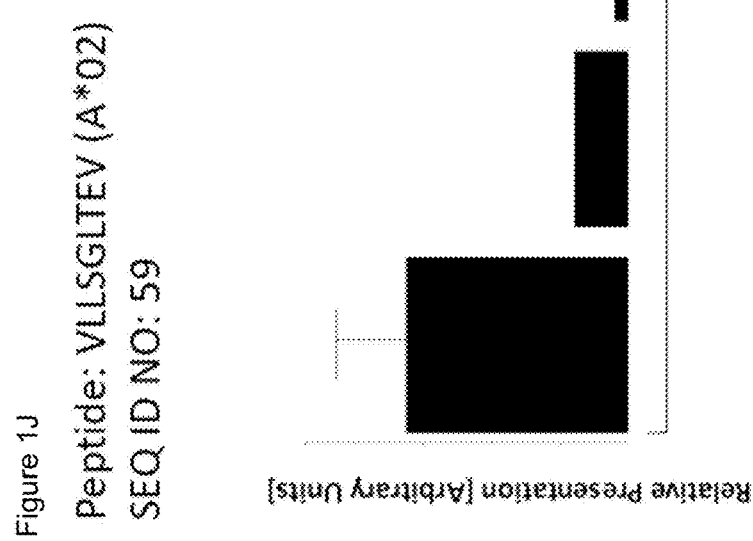
Figure 1K:
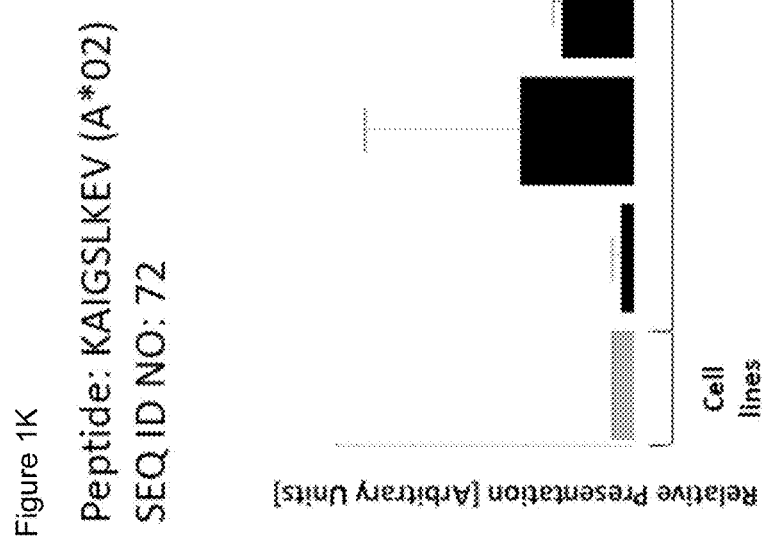
Figure 1M:
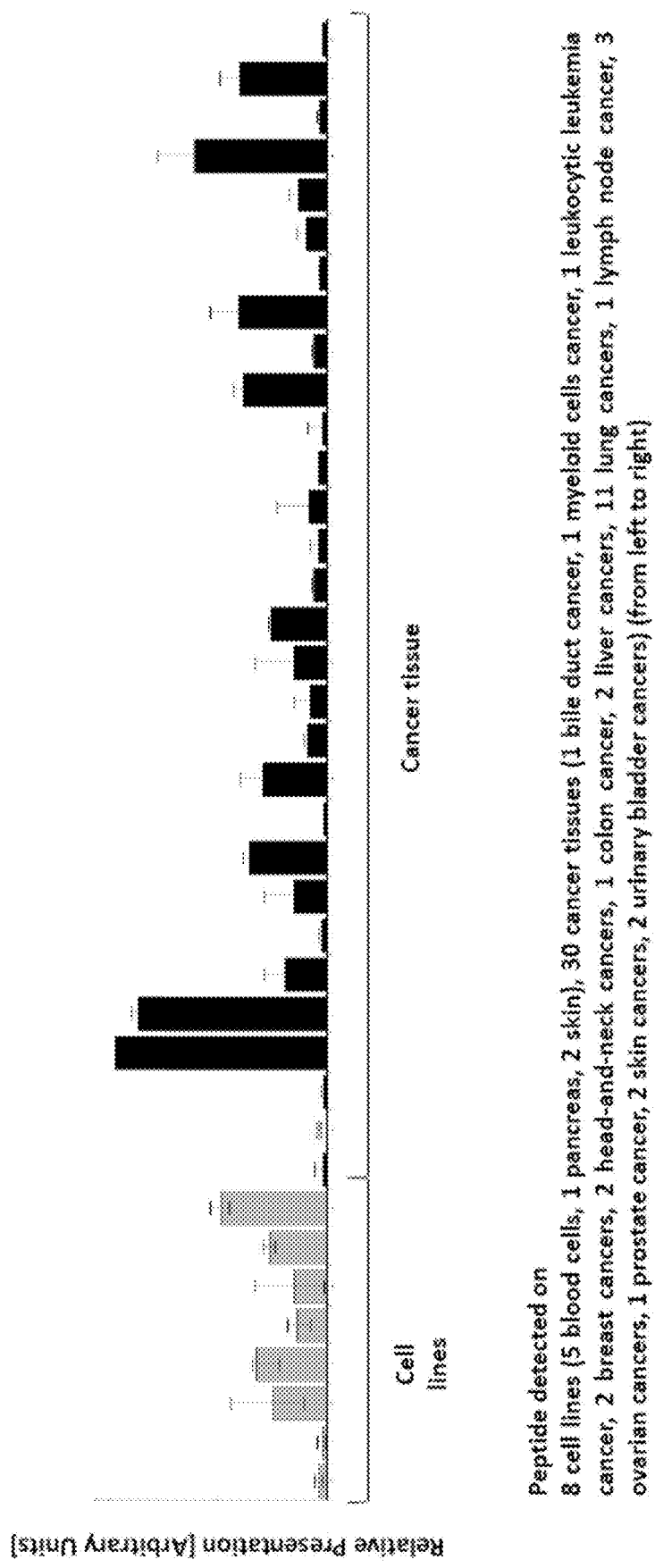

Identification and Quantitation of Tumor Associated Peptides Presented on the Cell Surface Tissue Samples Patients' tumor tissues were obtained from: Asterand (Detroit, Mich., USA & Royston, Herts, UK); Bio-Options Inc. (Brea, Calif., USA); ProteoGenex Inc. (Culver City, Calif., USA) Tissue Solutions Ltd (Glasgow, UK).

Normal tissues were obtained from Asterand (Detroit, Mich., USA & Royston, Herts, UK); Bio-Options Inc. (Brea, Calif., USA); BioServe (Beltsville, Md., USA); Capital BioScience Inc. (Rockville, Md., USA); Geneticist Inc. (Glendale, Calif., USA); Kyoto Prefectural University of Medicine (KPUM) (Kyoto, Japan); ProteoGenex Inc. (Culver City, Calif., USA); Tissue Solutions Ltd (Glasgow, UK); University Hospital Geneva (Geneva, Switzerland); University Hospital Heidelberg (Heidelberg, Germany); University Hospital Munich (Munich, Germany); University Hospital Tübingen (Tübingen, Germany)

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, —B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Figure 1P:
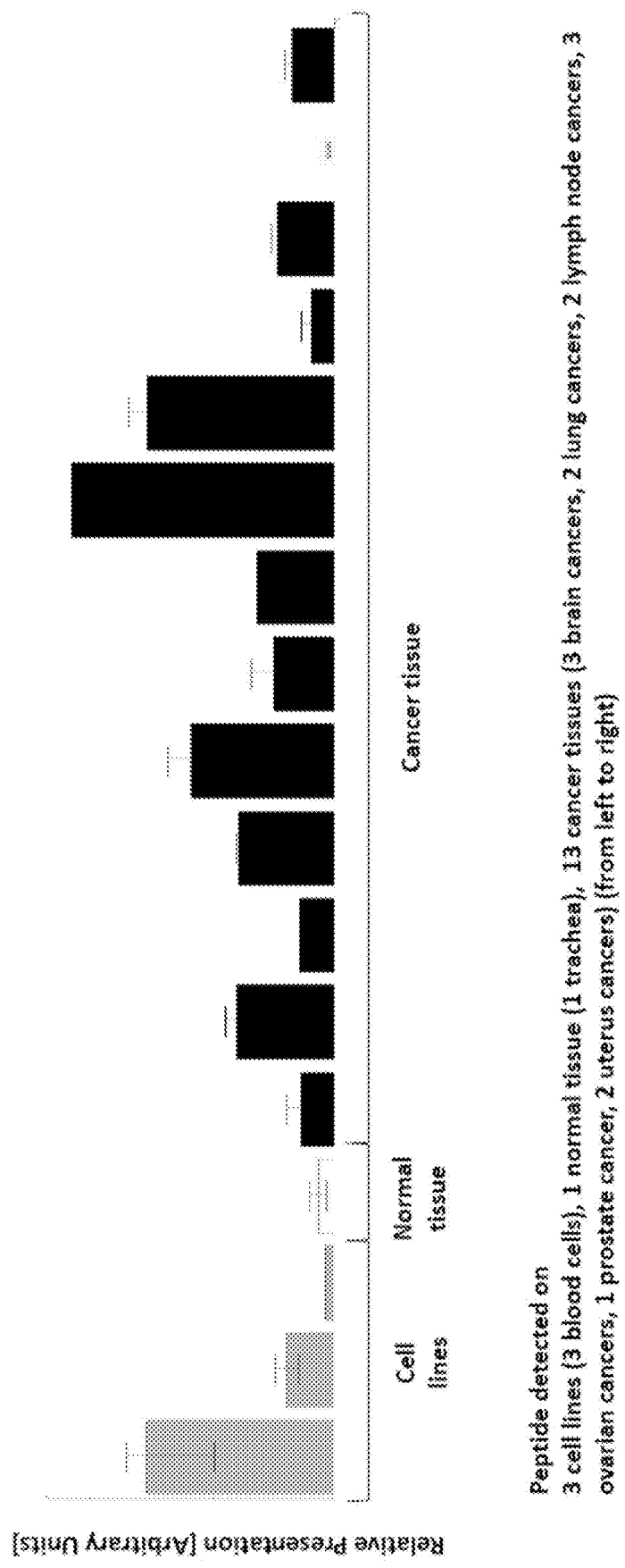
Figure 2A:
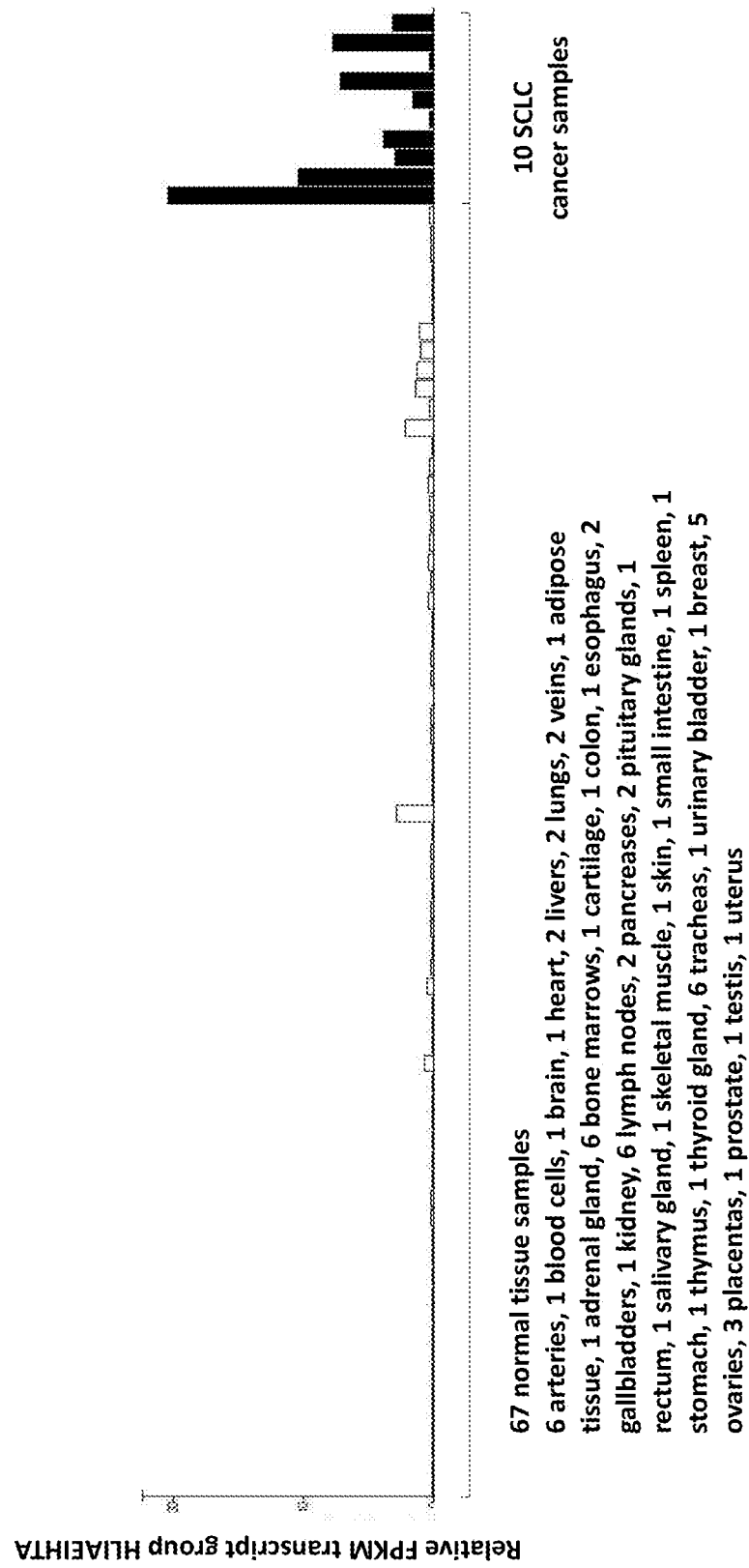
Figure 2B:
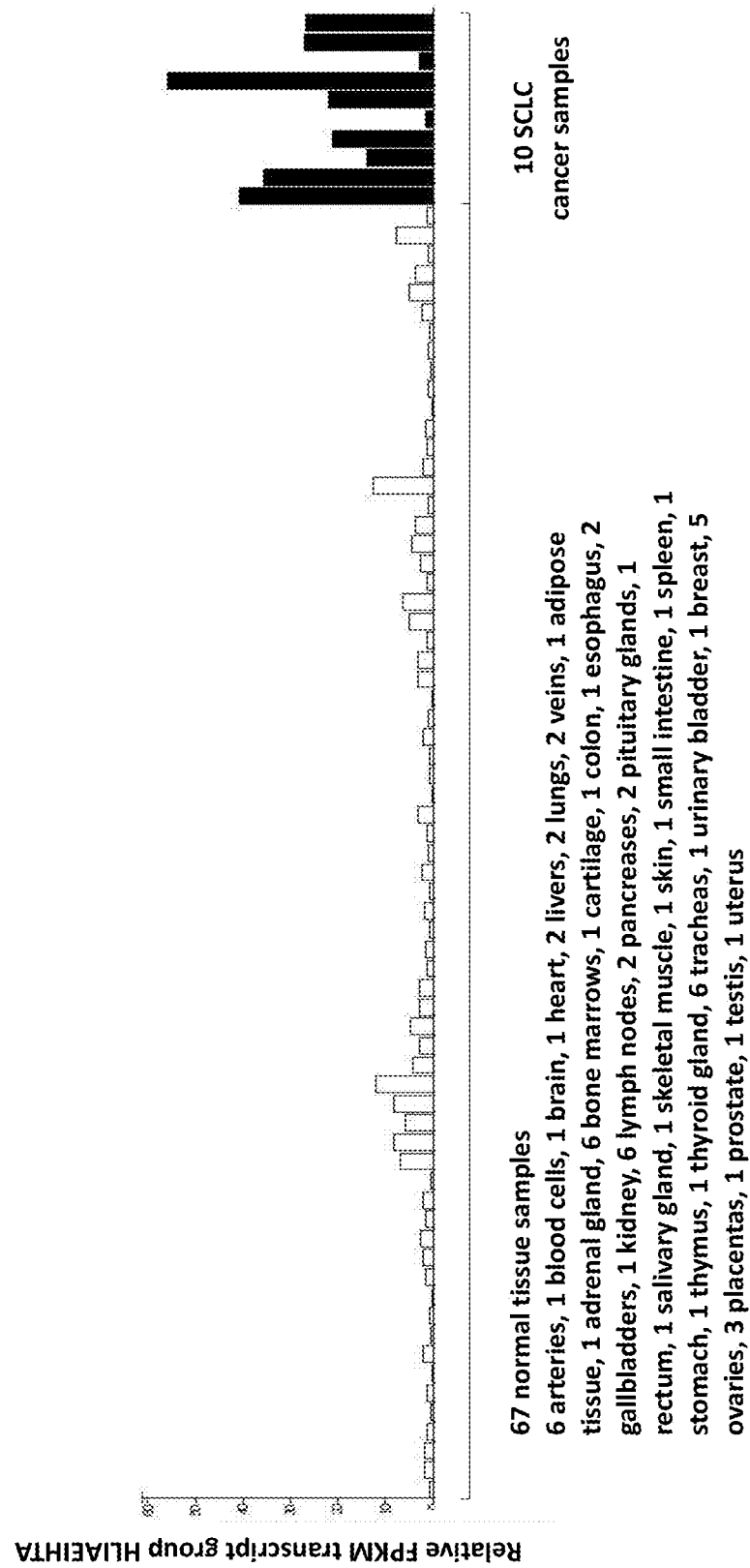
Figure 2D:
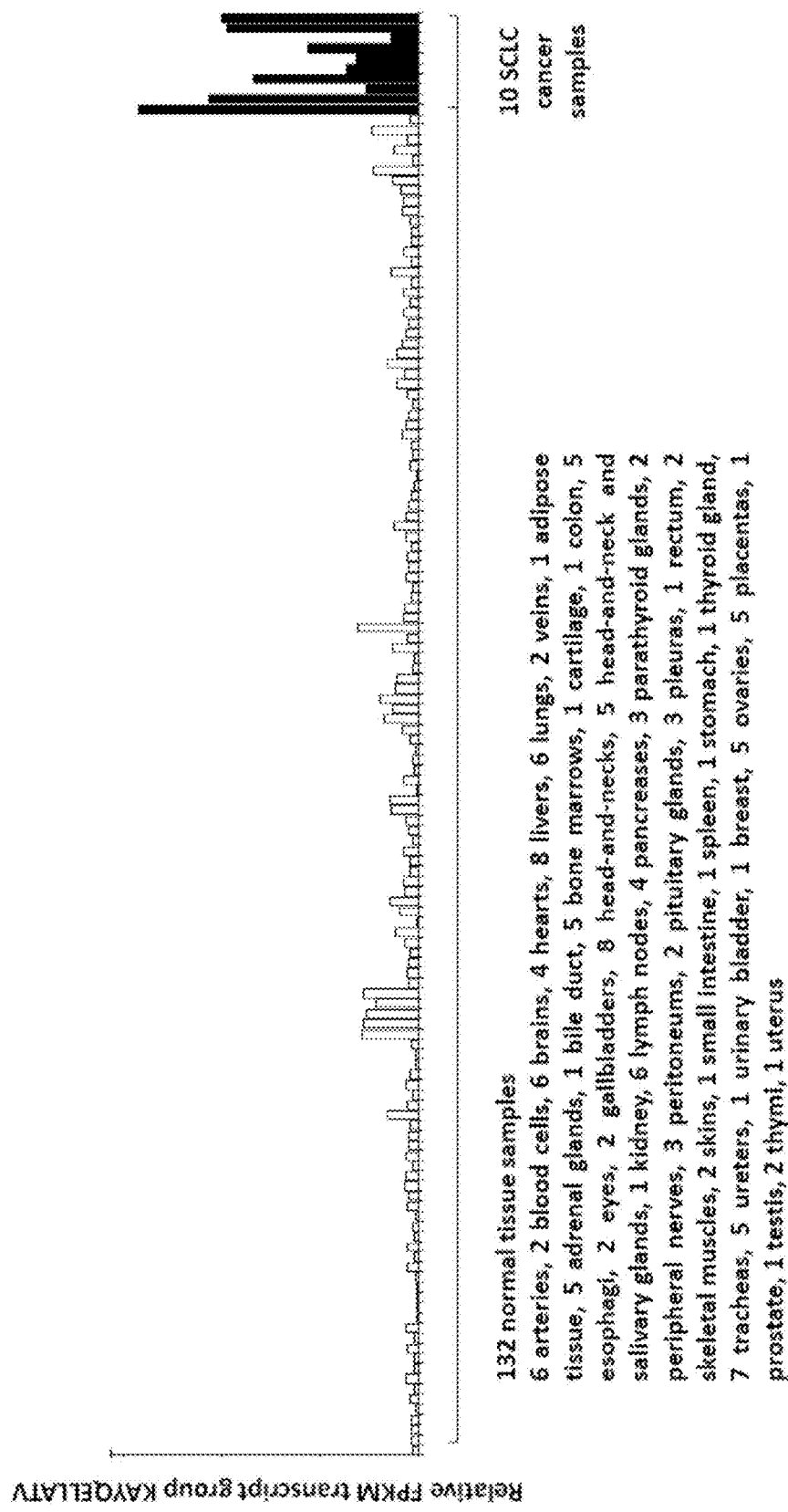

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose small cell lung cancer samples to a baseline of normal tissue samples. Presentation profiles of exemplary over-presented peptides are shown in FIGS. 1A-1P. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).The panel of normal tissues considered relevant for comparison with tumors consisted of: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Peptide Presentation |
|---|---|---|
| 1 | AMLEEVNYI | +++ |
| 2 | VMFNFPDQATV | ++ |
| 3 | VLAEIDPKQLV | +++ |
| 4 | GLLDPGMLVNI | + |
| 5 | SLQSLIISV | + |
| 6 | SIMDYVVFV | ++ |
| 7 | GLLGDIAIHL | +++ |
| 8 | VLIDDSQSIIFI | +++ |
| 9 | AAAPGEALHTA | + |
| 10 | ILAAGFDGM | + |
| 11 | KLFAIPILL | +++ |
| 15 | SLLTAISEV | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID NO: | Sequence | Peptide Presentation |
|---|---|---|
| 16 | VILDLPLVI | +++ |
| 17 | SLMLVTVEL | + |
| 19 | VLLTTAVEV | + |
| 20 | MLDEILLQL | + |
| 23 | YQIDTVINL | + |
| 24 | FLMEEVHMI | + |
| 26 | KMLDEAVFQV | + |
| 27 | SLDIITITV | +++ |
| 29 | NLISQLTTV | ++ |
| 31 | RLLQDPVGV | + |
| 35 | FMGDVFINV | + |
| 37 | SLFYNELHYV | + |
| 39 | GLDPTQFRV | +++ |
| 40 | GLLEVQVEV | +++ |
| 41 | KAYQELLATV | +++ |
| 42 | GLLEDERALQL | +++ |
| 43 | YLWSEVFSM | +++ |
| 44 | ALIVGIPSV | +++ |
| 45 | SLSGEIILHSV | +++ |
| 46 | ALWVAVPKA | +++ |
| 47 | GLLEALLKI | +++ |
| 49 | RLALNTPKV | ++ |
| 50 | FLLSQIVAL | +++ |
| 51 | ILDEAGVKYFL | +++ |
| 52 | ILASFMLTGV | +++ |
| 54 | HLFDIILTSV | ++ |
| 55 | LLIADNPQL | +++ |
| 56 | SLFSQMGSQYEL | +++ |
| 57 | VLIGDVLVAV | +++ |
| 58 | VLLNINGIDL | +++ |
| 59 | VLLSGLTEV | +++ |
| 60 | VVSGATETL | +++ |
| 61 | YQAPYFLTV | +++ |
| 62 | VMLPIGAVVMV | +++ |
| 63 | LLMSTENEL | ++ |
| 64 | VLFHQLQEI | + |
| 65 | VMYDLITEL | ++ |
| 66 | YLNLISTSV | +++ |
| 67 | MLYDIVPVV | + |
| 68 | FLFPVYPLI | + |
| 69 | KLFDRSVDL | ++ |
| 70 | TLLWKLVEV | +++ |
| 72 | KAIGSLKEV | +++ |
| 73 | SLSSYTPDV | +++ |
| 74 | FLDSLSPSV | +++ |
| 75 | SLDLHVPSL | +++ |
| 76 | VLTTVMITV | +++ |
| 78 | RIIDPEDLKALL | +++ |
| 79 | RLLEPAQVQQL | ++ |
| 80 | ILMDPSPEYA | +++ |
| 81 | LLAEIGAVTLV | ++ |
| 82 | ALSSVIKEL | + |
| 83 | KLLEIDIDGV | + |
| 84 | KMFENEFLL | + |
| 85 | FAYDGKDYLTL | + |
| 86 | KVIDYVPGI | + |
| 87 | LLQNNLPAV | + |
| 88 | TLHRETFYL | +++ |
| 89 | IQHDLIFSL | + |
| 90 | TLVDNISTMAL | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gallbladder, heart, kidney, large intestine, liver, lung, lymph node, nerve, pancreas, parathyroid gland, pituitary, pleura, salivary gland, skeletal muscle, skin, small intestine, spleen, stomach, thymus, thyroid gland, trachea, ureter, urinary bladder.

| SEQ ID NO: | Sequence | Peptide Presentation |
|---|---|---|
| 95 | ALYSKGILL | + |
| 96 | NLLKLIAEV | + |
| 97 | ALLDGTVFEI | ++ |
| 98 | ALVDHLNVGV | + |
| 99 | QMLEAIKALEV | ++ |
| 100 | VADPETRTV | + |
| 101 | AMNSQILEV | + |
| 103 | SLLEYQMLV | + |
| 105 | SMYDKVLML | + |
| 106 | KMPDDVWLV | + |
| 107 | AMYGTKLETI | + |
| 110 | GLTETGLYRI | +++ |
| 111 | FLPEAPAEL | +++ |
| 112 | LLLPGVIKTV | +++ |
| 114 | ALLEPGGVLTI | +++ |
| 115 | ALLPSDCLQEA | +++ |
| 116 | ALLVRLQEV | +++ |
| 117 | FLLDSAPLNV | + |
| 118 | KLPSFLANV | +++ |
| 119 | SLIDDNNEINL | + |
| 120 | SLAADIPRL | ++ |
| 121 | YMLEHVITL | + |
| 124 | SLITDLQTI | ++ |
| 125 | LLSEPSLLRTV | +++ |
| 126 | AAASLIRLV | +++ |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, Mich., USA & Royston, Herts, UK); Bio-Options Inc. (Brea, Calif., USA); Geneticist Inc. (Glendale, Calif., USA); ProteoGenex Inc. (Culver City, Calif., USA); Tissue Solutions Ltd (Glasgow, UK)

Total RNA from tumor tissues for RNASeq experiments was obtained from: Asterand (Detroit, Mich., USA & Royston, Herts, UK); BioCat GmbH (Heidelberg, Germany); BioServe (Beltsville, Md., USA); Geneticist Inc. (Glendale, Calif., USA); Istituto Nazionale Tumori "Pascale" (Naples, Italy); ProteoGenex Inc. (Culver City, Calif., USA); University Hospital Heidelberg (Heidelberg, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values. Exemplary expression profiles of source genes of the present invention that are highly over-expressed or exclusively expressed in small cell lung cancer are shown in FIGS. 2A-2D. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, artery, blood cells, bone marrow, brain, cartilage, colon, esophagus, gallbladder, heart, kidney, liver, lung, lymph node, pancreas, pituitary, rectum, salivary gland, skeletal muscle, skin, small intestine, spleen, stomach, thymus, thyroid gland, trachea, urinary bladder, vein. In case expression data for several samples of the same tissue type were available, the arithmetic mean of all respective samples was used for the calculation.

| SEQ ID No | Sequence | Gene Expression |
|---|---|---|
| 1 | AMLEEVNYI | +++ |
| 10 | ILAAGFDGM | ++ |
| 25 | GLSETILAV | ++ |
| 39 | GLDPTQFRV | ++ |
| 41 | KAYQELLATV | +++ |
| 42 | GLLEDERALQL | +++ |
| 51 | ILDEAGVKYFL | + |
| 70 | TLLWKLVEV | +++ |
| 72 | KAIGSLKEV | +++ |
| 83 | KLLEIDIDGV | ++ |
| 88 | TLHRETFYL | +++ |
| 91 | KLQDGVHII | + |
| 92 | YLQDYTDRV | +++ |
| 95 | ALYSKGILL | ++ |
| 96 | NLLKLIAEV | ++ |
| 110 | GLTETGLYRI | + |
| 111 | FLPEAPAEL | +++ |
| 121 | YMLEHVITL | ++ |
| 122 | SMMPDELLTSL | + |
| 123 | KLDKNPNQV | + |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO: 142) from modified Melan-A/MART-1) and A*0201/DDX5-001 (YLLPAIVHI from DDX5, SEQ ID NO: 143), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Small Cell Lung Cancer Peptides

Figure 3A:
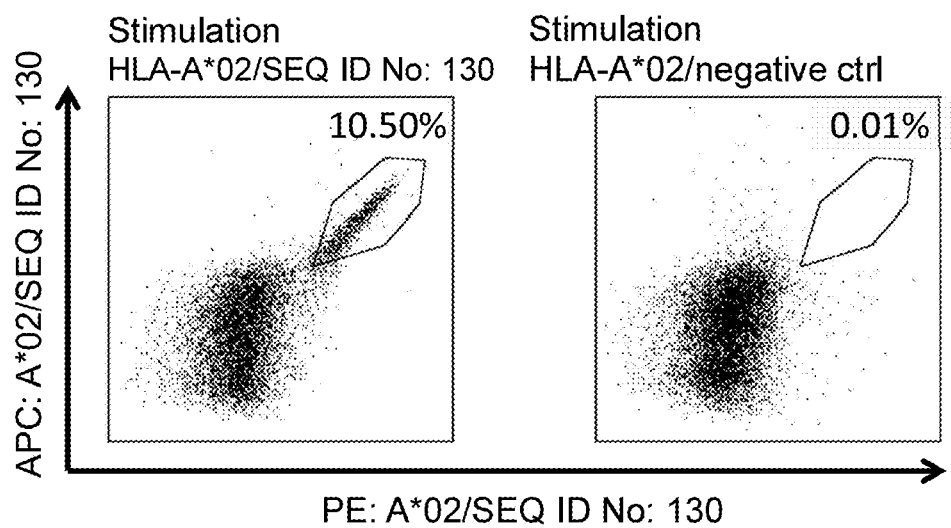
FIGS. 3A-3B shows exemplary immunogenicity data: flow cytometry results after peptide-specific multimer staining.
Figure 3B:
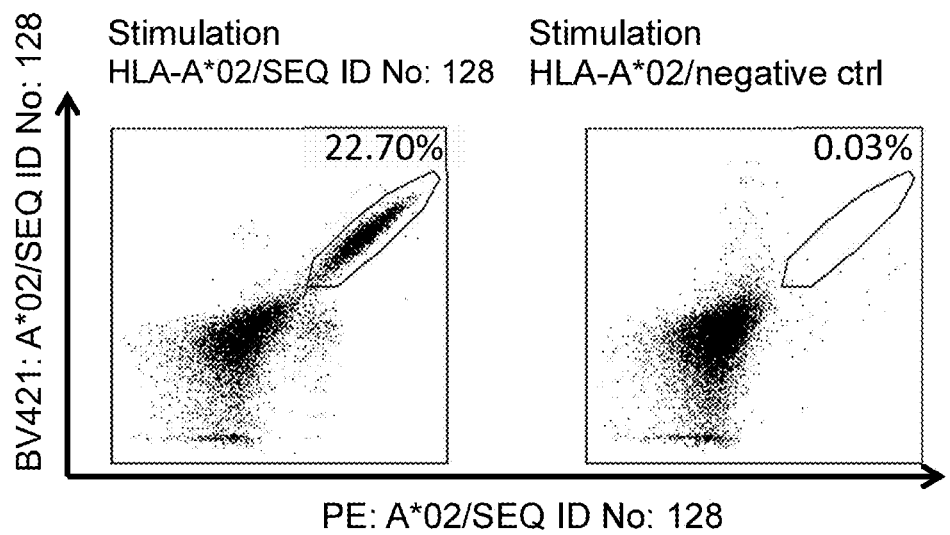
Figure 4A:
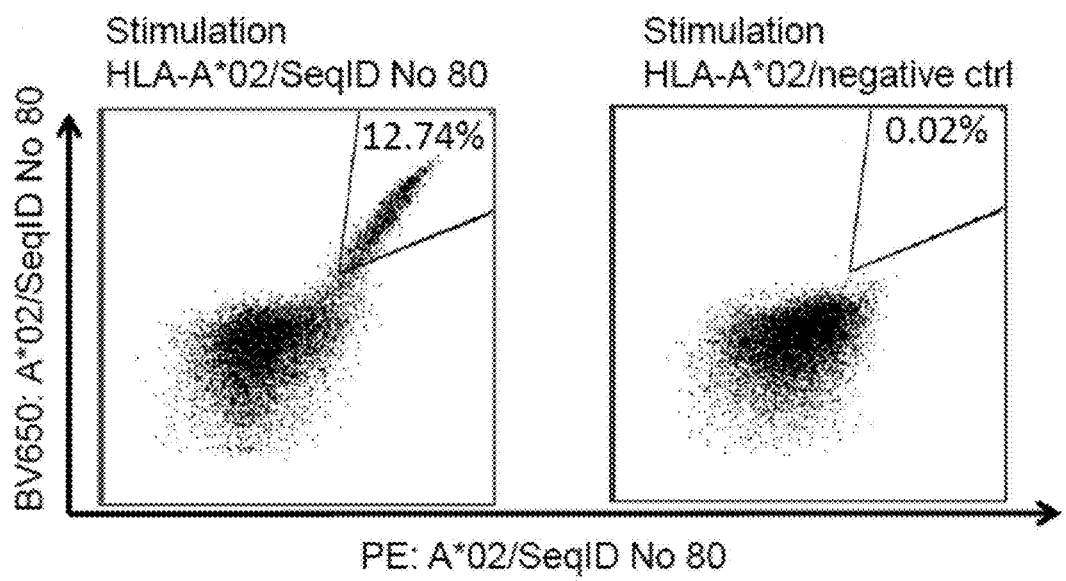
FIGS. 4A-4C shows exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 80 peptide ILMDPSPEYA (FIG. 4A, left panel), SeqID No 82 peptide ALSSVIKEL (FIG. 4B, left panel) and SeqID No 110 peptide GLTETGLYRI (FIG. 4C, left panel), respectively. After three cycles of stimulation, the detection of peptide-reactive cells was performed by 2D multimer staining with A*02/SeqID No 80 (FIG. 4A), A*02/SeqID No 82 (FIG. 4B) or A*02/SeqID No 110 (FIG. 4C). Right panels (FIGS. 4A, 4B and 4C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 4B:
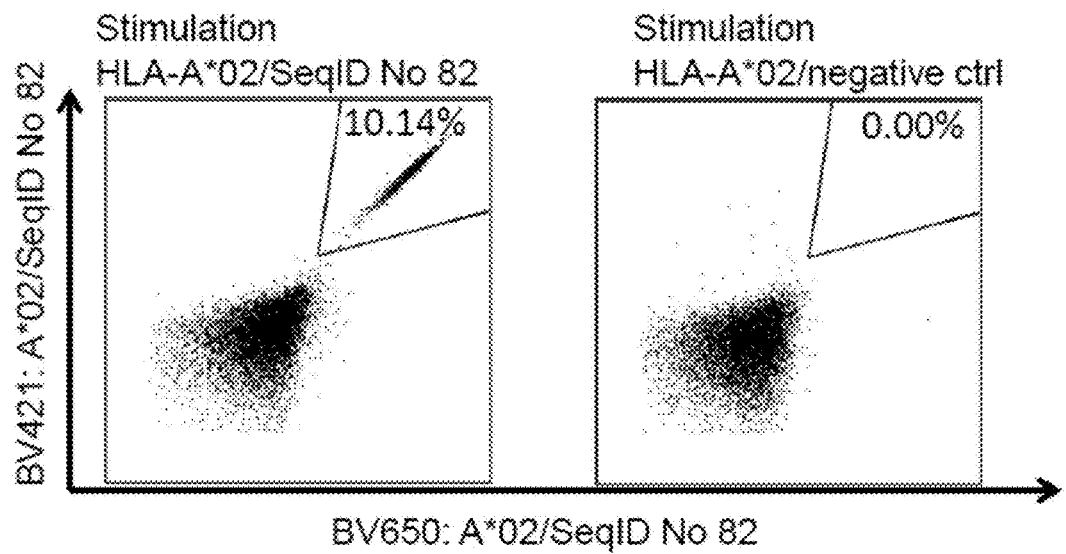
Figure 4C:
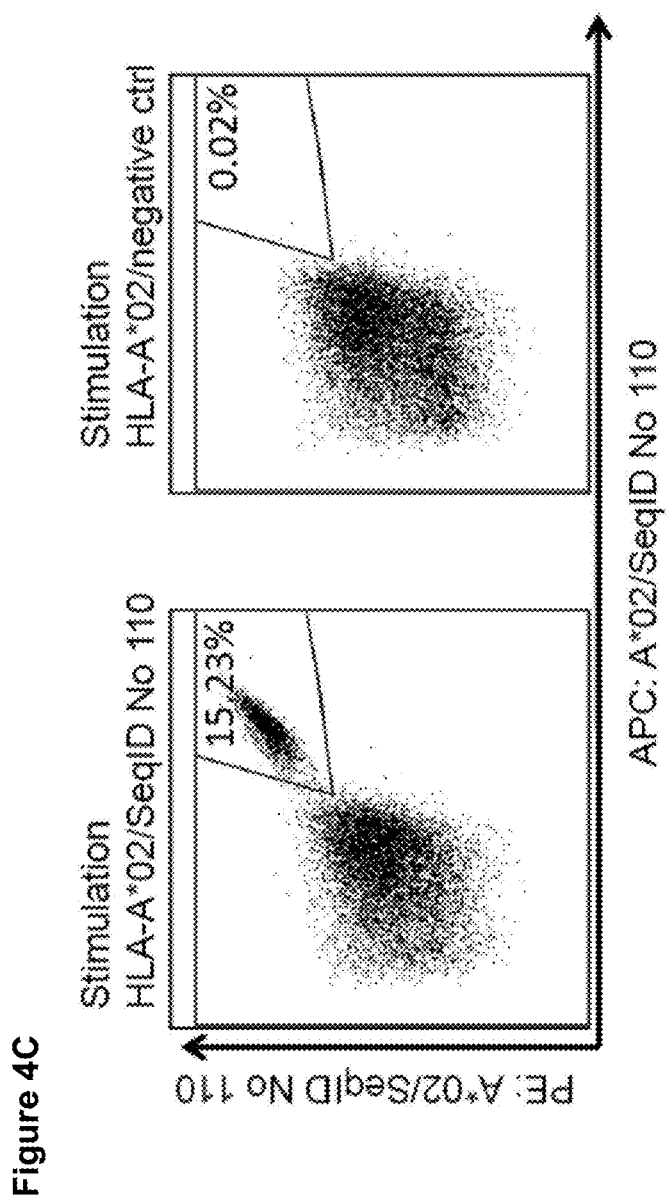

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A and 3B together with corresponding negative controls. Results for 4 peptides from the invention are summarized in Table 10.

TABLE 10A in vitro immunogenicity of HLA class I peptides of the invention
Exemplary results of in vitro immunogenicity experiments conducted by the applicant for the peptides of the invention. <20% = +; 20%-49% = ++; 50%-69% = +++; > = 70% = ++++

| Seq ID | Sequence | wells |
|---|---|---|
| 128 | SLAPAGVIRV | + |
| 129 | RVADYIVKV | + |
| 130 | SLYDNQITTV | ++ |
| 132 | NLLAEIHGV | + |

TABLE 10B in vitro immunogenicity of HLA class I peptides of the invention
Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; > = 70% = ++++

| Seq ID No | Sequence | Wells positive [%] |
|---|---|---|
| 2 | VMFNFPDQATV | + |
| 4 | GLLDPGMLVNI | ++ |
| 6 | SIMDYVVFV | + |
| 11 | KLFAIPILL | ++++ |
| 39 | GLDPTQFRV | ++++ |
| 80 | ILMDPSPEYA | +++ |
| 82 | ALSSVIKEL | + |
| 110 | GLTETGLYRI | +++ |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores.
Binding of HLA-class I restricted peptides to HLA-A*02:01 was ranged by peptide exchange yield:
≥10% = +; ≥20% = ++; ≥50 = +++; ≥75% = ++++

| Seq ID No | Sequence | Peptide exchange |
|---|---|---|
| 1 | AMLEEVNYI | +++ |
| 2 | VMFNFPDQATV | +++ |
| 3 | VLAEIDPKQLV | +++ |
| 4 | GLLDPGMLVNI | +++ |
| 5 | SLQSLIISV | ++++ |
| 6 | SIMDYVVFV | ++++ |
| 7 | GLLGDIAIHL | +++ |
| 9 | AAAPGEALHTA | ++ |
| 11 | KLFAIPILL | +++ |
| 12 | MLFEGLDLVSA | +++ |
| 13 | FLTAFLVQI | +++ |
| 14 | ILIETKLVL | +++ |
| 15 | SLLTAISEV | +++ |

TABLE 11-continued

MHC class I binding scores.
Binding of HLA-class I restricted peptides to
HLA-A*02:01 was ranged by peptide exchange yield:
≥10% = +; ≥20% = ++; ≥50% = +++; ≥75% = ++++

| Seq ID No | Sequence | Peptide exchange |
|---|---|---|
| 16 | VILDLPLVI | +++ |
| 17 | SLMLVTVEL | +++ |
| 18 | ALGEISVSV | +++ |
| 19 | VLLTTAVEV | +++ |
| 20 | MLDEILLQL | +++ |
| 21 | TMEEMIFEV | +++ |
| 22 | LLPEKSWEI | +++ |
| 23 | YQIDTVINL | +++ |
| 24 | FLMEEVHMI | +++ |
| 25 | GLSETILAV | ++++ |
| 26 | KMLDEAVFQV | ++++ |
| 27 | SLDIITITV | ++++ |
| 28 | ILVSQLEQL | ++++ |
| 30 | KMLGLTVSL | +++ |
| 31 | RLLQDPVGV | ++++ |
| 32 | ALTSLELEL | +++ |
| 34 | LVFEGIMEV | +++ |
| 35 | FMGDVFINV | ++++ |
| 36 | RMDGAVTSV | +++ |
| 37 | SLFYNELHYV | +++ |
| 38 | GLISSLNEI | ++++ |
| 39 | GLDPTQFRV | +++ |
| 40 | GLLEVQVEV | +++ |
| 41 | KAYQELLATV | +++ |
| 42 | GLLEDERALQL | +++ |
| 43 | YLWSEVFSM | +++ |
| 44 | ALIVGIPSV | ++++ |
| 45 | SLSGEIILHSV | ++ |
| 46 | ALWVAVPKA | +++ |
| 47 | GLLEALLKI | +++ |
| 48 | SLIGLDLSSV | +++ |
| 49 | RLALNTPKV | ++ |
| 50 | FLLSQIVAL | +++ |
| 51 | ILDEAGVKYFL | +++ |
| 52 | ILASFMLTGV | ++++ |
| 53 | LLSEEHITL | ++++ |
| 54 | HLFDIILTSV | ++++ |
| 55 | LLIADNPQL | ++++ |
| 56 | SLFSQMGSQYEL | +++ |
| 57 | VLIGDVLVAV | ++++ |
| 58 | VLLNINGIDL | ++++ |
| 59 | VLLSGLTEV | ++++ |
| 60 | VVSGATETL | ++++ |
| 61 | YQAPYFLTV | +++ |
| 62 | VMLPIGAVVMV | +++ |
| 63 | LLMSTENEL | +++ |
| 64 | VLFHQLQEI | +++ |
| 65 | VMYDLITEL | +++ |
| 66 | YLNLISTSV | +++ |
| 67 | MLYDIVPVV | +++ |
| 68 | FLFPVYPLI | +++ |
| 69 | KLFDRSVDL | ++ |
| 70 | TLLWKLVEV | ++ |
| 71 | FIFEQVQNV | +++ |
| 72 | KAIGSLKEV | +++ |
| 73 | SLSSYTPDV | +++ |
| 74 | FLDSLSPSV | +++ |
| 75 | SLDLHVPSL | +++ |
| 77 | AIIDGKIFCV | +++ |
| 78 | RIIDPEDLKALL | ++++ |
| 79 | RLLEPAQVQQL | +++ |
| 80 | ILMDPSPEYA | +++ |
| 81 | LLAEIGAVTLV | +++ |
| 82 | ALSSVIKEL | +++ |
| 83 | KLLEIDIDGV | +++ |
| 84 | KMFENEFLL | +++ |
| 85 | FAYDGKDYLTL | +++ |
| 86 | KVIDYVPGI | +++ |
| 87 | LLQNNLPAV | ++++ |
| 88 | TLHRETFYL | ++++ |
| 89 | IQHDLIFSL | +++ |
| 90 | TLVDNISTMAL | +++ |
| 91 | KLQDGVHII | +++ |

TABLE 11-continued

MHC class I binding scores.
Binding of HLA-class I restricted peptides to
HLA-A*02:01 was ranged by peptide exchange yield:
≥10% = +; ≥20% = ++; ≥50 = +++; ≥75% = ++++

| Seq ID No | Sequence | Peptide exchange |
|---|---|---|
| 92 | YLQDYTDRV | +++ |
| 93 | ALRETVVEV | +++ |
| 94 | ALFPVAEDISL | +++ |
| 95 | ALYSKGILL | ++++ |
| 96 | NLLKLIAEV | ++++ |
| 97 | ALLDGTVFEI | +++ |
| 98 | ALVDHLNVGV | +++ |
| 99 | QMLEAIKALEV | ++++ |
| 100 | VADPETRTV | + |
| 101 | AMNSQILEV | +++ |
| 102 | ALFARPDLLLL | ++++ |
| 103 | SLLEYQMLV | ++++ |
| 104 | TLIQFTVKL | +++ |
| 105 | SMYDKVLML | ++++ |
| 106 | KMPDDVWLV | ++++ |
| 107 | AMYGTKLETI | ++++ |
| 108 | ILLDDQFQPKL | ++++ |
| 109 | SLFERLVVL | ++++ |
| 110 | GLTETGLYRI | +++ |
| 111 | FLPEAPAEL | +++ |
| 112 | LLLPGVIKTV | +++ |
| 114 | ALLEPGGVLTI | +++ |
| 115 | ALLPSDCLQEA | +++ |
| 116 | ALLVRLQEV | ++++ |
| 117 | FLLDSAPLNV | ++++ |
| 118 | KLPSFLANV | +++ |
| 120 | SLAADIPRL | +++ |
| 121 | YMLEHVITL | +++ |
| 122 | SMMPDELLTSL | +++ |
| 123 | KLDKNPNQV | +++ |
| 124 | SLITDLQTI | +++ |
| 125 | LLSEPSLLRTV | +++ |
| 126 | AAASLIRLV | + |

REFERENCE LIST

Abba, M. C. et al., Breast Cancer Res 6 (2004): R499-R513
Adamowicz, M. et al., Genes Chromosomes. Cancer 45 (2006): 829-838
Adel, Fahmideh M. et al., Carcinogenesis 36 (2015): 876-882
Ahn, Y. H. et al., J Clin Invest 122 (2012): 3170-3183
Akao, Y. et al., Cancer Res 55 (1995): 3444-3449
Al-Lamki, Z. et al., Pediatr. Hematol. Oncol 22 (2005): 629-643
Alhopuro, P. et al., Int. J Cancer 130 (2012): 1558-1566
Allard, M. et al., PLoS. One. 6 (2011): e21118
Allison, J. P. et al., Science 270 (1995): 932-933
Alm-Kristiansen, A. H. et al., Oncogene 27 (2008): 4644-4656
Alvarez, C. et al., Mol. Carcinog 52 (2013): 475-487
American Cancer Society, (2015a), www.cancer.org
American Cancer Society, (2015b), www.cancer.org
Andersen, R. S. et al., Nat. Protoc. 7 (2012): 891-902
Angulo, J. C. et al., J Urol. 195 (2016): 619-626
Appay, V. et al., Eur. J Immunol. 36 (2006): 1805-1814
Arafat, H. et al., Surgery 150 (2011): 306-315
Arvanitis, D. A. et al., Oncol Rep. 20 (2008): 751-760
Asmann, Y. W. et al., Cancer Res 62 (2002): 3308-3314
Balamurugan, K. et al., Am. J Physiol Gastrointest. Liver Physiol 285 (2003): G73-G77
Ballerini, P. et al., Haematologica 93 (2008): 1658-1665
Banchereau, J. et al., Cell 106 (2001): 271-274
Baratta, M. G. et al., Proc. Natl. Acad. Sci. U.S.A 112 (2015): 232-237
Barber, L. J. et al., Cell 135 (2008): 261-271
Bashtrykov, P. et al., Cell Cycle 14 (2015): 5
Bawa-Khalfe, T. et al., J Biol Chem 285 (2010): 25859-25866
Beatty, G. et al., J Immunol 166 (2001): 2276-2282
Beggs, J. D., Nature 275 (1978): 104-109
Bengochea, A. et al., Br. J Cancer 99 (2008): 143-150
Benjamini, Y. et al., Journal of the Royal Statistical Society. Series B (Methodological), Vol. 57 (1995): 289-300
Bennett, C. B. et al., PLoS. One. 3 (2008a): e1448
Bennett, K. L. et al., Cancer Res 68 (2008b): 4494-4499
Bhogaraju, S. et al., Science 341 (2013): 1009-1012
Bi, W. et al., Oncol Rep. 29 (2013): 1533-1539
Bierkens, M. et al., Genes Chromosomes. Cancer 52 (2013): 56-68
Bojjireddy, N. et al., J Cell Sci. (2014)
Borazanci, E. et al., World J Gastrointest. Oncol 7 (2015): 132-140
Bossard, C. et al., Int. J Cancer 131 (2012): 855-863
Boulter, J. M. et al., Protein Eng 16 (2003): 707-711
Braumuller, H. et al., Nature (2013)
Braun, R. J. et al., Biochim. Biophys. Acta 1783 (2008): 1418-1435
Brechmann, M. et al., Immunity. 37 (2012): 697-708
Bredel, M. et al., JAMA 302 (2009): 261-275
Bredholt, G. et al., Oncotarget. 6 (2015): 39676-39691
Brossart, P. et al., Blood 90 (1997): 1594-1599
Broude, E. V. et al., Curr. Cancer Drug Targets. 15 (2015): 739-749
Bruckdorfer, T. et al., Curr. Pharm. Biotechnol. 5 (2004): 29-43
Buchet-Poyau, K. et al., Nucleic Acids Res 35 (2007): 1289-1300
Burdelski, C. et al., BMC. Cancer 15 (2015): 538
Burgess, A. W. et al., Exp. Cell Res 317 (2011): 2748-2758
Caba, O. et al., Dig. Dis. Sci. 59 (2014): 2714-2720
Cai, K. et al., Lin. Chung Er. Bi Yan. Hou Tou. Jing. Wai Ke. Za Zhi. 26 (2012): 425-428
Caldon, C. E. et al., Cell Cycle 12 (2013): 606-617
Caldon, C. E. et al., Mol. Cell Biol 29 (2009): 4623-4639

Campone, M. et al., Breast Cancer Res Treat. 109 (2008): 491-501
Campos, B. et al., Am. J Pathol. 178 (2011): 1953-1964
Camps, J. et al., Cancer Res 73 (2013): 2003-2013
Card, K. F. et al., Cancer Immunol Immunother. 53 (2004): 345-357
Carlsen, E. O. et al., Am. J Med Genet. A 167A (2015): 1890-1896
Carlucci, F. et al., Biomed. Pharmacother. 63 (2009): 663-671
Celius, T. et al., Toxicol. Appl. Pharmacol. 247 (2010): 60-69
Cha, J. D. et al., Oral Surg. Oral Med Oral Pathol. Oral Radiol. Endod. 111 (2011): 594-607
Chae, Y. K. et al., Oncotarget. 6 (2015): 37117-37134
Chanock, S. J. et al., Hum. Immunol. 65 (2004): 1211-1223
Chantome, A. et al., Exp. Cell Res 315 (2009): 3620-3630
Chen, D. et al., Cancer Lett. 362 (2015a): 208-217
Chen, H. et al., J Clin Immunol. 19 (1999): 186-193
Chen, J. et al., Int. J Cancer 122 (2008): 2249-2254
Chen, J. et al., J Hepatol. 62 (2015b): 1287-1295
Chen, T. et al., Oncogene 34 (2015c): 4019-4031
Chen, W. M. et al., Dig. Dis. Sci. 60 (2015d): 1655-1662
Chen, Y. et al., Med. Oncol 31 (2014): 304
Chen, Y. et al., Proteomics. 7 (2007a): 2384-2397
Chen, Y. et al., Cancer Biol Ther. 8 (2009): 607-614
Chen, Y. G. et al., J Biol Chem 282 (2007b): 9688-9695
Chen, Y. L. et al., Biochem. Biophys. Res Commun. 425 (2012): 290-296
Cheng, J. M. et al., J Biol Regul. Homeost. Agents 29 (2015): 85-92
Choi, Y. J. et al., Hum. Pathol. 45 (2014): 1674-1681
Choi, Y. W. et al., Int. J Gynecol. Cancer 17 (2007): 687-696
Chuang, T. H. et al., Proc. Natl. Acad. Sci. U.S.A 92 (1995): 10282-10286
Ciccia, A. et al., Mol. Cell 25 (2007): 331-343
Cipriano, R. et al., Mol. Cancer Res 12 (2014): 1156-1165
Clark, A. D. et al., Crit Rev Biochem. Mol. Biol 50 (2015): 393-426
Claro da, Silva T. et al., Mol Aspects Med. 34 (2013): 252-269
Clay, M. R. et al., Development 140 (2013): 3198-3209
Cohen, C. J. et al., J Mol Recognit. 16 (2003a): 324-332
Cohen, C. J. et al., J Immunol 170 (2003b): 4349-4361
Coligan, J. E. et al., Current Protocols in Protein Science (1995)
Colombetti, S. et al., J Immunol. 176 (2006): 2730-2738
Cornen, S. et al., PLoS. One. 9 (2014): e81843
Corral, R. et al., PLoS. One. 8 (2013): e71211
Crago, A. M. et al., Curr. Opin. Oncol 23 (2011): 373-378
Cui, Y. et al., Tumour. Biol 36 (2015): 9919-9927
Cui, Y. et al., Biosci. Trends 7 (2013): 259-263
Cunnick, J. M. et al., Mol. Cell Biol 29 (2009): 5742-5750
Dai, J. et al., PLoS. One. 6 (2011): e21120
Dasari, V. K. et al., J Urol. 165 (2001): 1335-1341
Davalieva, K. et al., Prostate 75 (2015): 1586-1600
Davis, M. A. et al., Genes Dev. 27 (2013): 151-156
De, Keersmaecker K. et al., Haematologica 99 (2014): 85-93
Dean, M. et al., Genome Res 11 (2001): 1156-1166
Deb, S. et al., Mod. Pathol. 27 (2014): 1223-1230
del, Fresno C. et al., J Immunol. 174 (2005): 3032-3040
Deng, J. et al., PLoS. One. 8 (2013): e76450
Dengjel, J. et al., Clin Cancer Res 12 (2006): 4163-4170
Denkberg, G. et al., J Immunol 171 (2003): 2197-2207
DeRycke, M. S. et al., Cancer Epidemiol. Biomarkers Prev. 22 (2013): 1239-1251
Dhanoa, B. S. et al., Hum. Genomics 7 (2013): 13
Di, K. et al., Oncogene 32 (2013): 5038-5047
Dickinson, R. E. et al., Br. J Cancer 91 (2004): 2071-2078
Ding, X. et al., Int. J Cancer 136 (2015): 955-964
Diniz, M. G. et al., Tumour. Biol (2015)
Draberova, E. et al., J Neuropathol. Exp. Neurol. 74 (2015): 723-742
El-Naggar, A. M. et al., Cancer Cell 27 (2015): 682-697
Elgohary, N. et al., Int. J Oncol 46 (2015): 597-606
Elias, D. et al., Oncogene 34 (2015): 1919-1927
Enqvist, M. et al., J Immunol. 187 (2011): 3546-3554
Euer, N. et al., Anticancer Res 22 (2002): 733-740
Falk, K. et al., Nature 351 (1991): 290-296
Fan, T. et al., Tumour. Biol 35 (2014): 519-527
Faronato, M. et al., Oncotarget. (2015)
Feng, Y. et al., Zhonghua Yi. Xue. Za Zhi. 94 (2014): 596-598
Feng, Z. et al., Oncogene 25 (2006): 1-7
Fernandes, C. F. et al., Biochem. Biophys. Res Commun. 361 (2007): 26-32
Fields, A. P. et al., Adv. Enzyme Regul. 50 (2010): 190-200
Figueroa, M. E. et al., J Clin Invest 123 (2013): 3099-3111
Fong, L. et al., Proc. Natl. Acad. Sci. U.S.A 98 (2001): 8809-8814
Fox, S. B. et al., Cancer Res 64 (2004): 6075-6081
Francavilla, C. et al., Mol. Cell 51 (2013): 707-722
Fu, A. et al., Mol. Carcinog 51 (2012): 923-929
Fu, L. et al., Hepatology 51(2010): 1624-1634
Fujita, T. et al., Cancer Sci. 104 (2013): 214-222
Gabrilovich, D. I. et al., Nat Med. 2 (1996): 1096-1103
Gallenberger, M. et al., Hum. Mol. Genet. 20 (2011): 422-435
Gama, V. et al., Sci. Signal. 7 (2014): ra67
Gao, G. et al., Genes Chromosomes. Cancer 53 (2014): 392-401
Garcia-Santisteban, I. et al., Mol. Cancer 12 (2013): 91
Gardina, P. J. et al., BMC. Genomics 7 (2006): 325
Garnis, C. et al., Int. J Cancer 116 (2005): 813-819
Gattinoni, L. et al., Nat Rev. Immunol 6 (2006): 383-393
Ghosal, A. et al., Biochim. Biophys. Acta 1808 (2011): 2073-2080
Ghoshal, K. et al., PLoS. One. 5 (2010): e10338
Giangreco, A. et al., Development 136 (2009): 3505-3514
Gnjatic, S. et al., Proc Natl. Acad. Sci. U.S.A 100 (2003): 8862-8867
Godkin, A. et al., Int. Immunol 9 (1997): 905-911
Going, J. J. et al., Gut 50 (2002): 373-377
Gomez-Ferreria, M. A. et al., J Cell Sci. 125 (2012): 3745-3751
Gonda, T. J. et al., Expert. Opin. Biol Ther. 8 (2008): 713-717
Gonzalez, M. A. et al., J Clin Oncol 21 (2003): 4306-4313
Goode, E. L. et al., Nat Genet. 42 (2010): 874-879
Gorogh, T. et al., Int. J Cancer 138 (2016): 2529-2538
Green, M. R. et al., Molecular Cloning, A Laboratory Manual 4th (2012)
Greenfield, E. A., Antibodies: A Laboratory Manual 2nd (2014)
Greenhough, A. et al., Carcinogenesis 30 (2009): 377-386
Grice, D. M. et al., J Biol Chem 285 (2010): 37458-37466
Gu, Y. et al., Mol. Carcinog 55 (2016): 292-299
Gudas, J. M. et al., Mol. Cell Biol 19 (1999): 612-622
Guerreiro, A. S. et al., Mol. Cancer Res 9 (2011): 925-935
Guo, X. et al., Sci. Rep. 5 (2015): 11846
Guo, X. et al., Oncogene 29 (2010): 3908-3920
Gutierrez, M. L. et al., PLoS. One. 6 (2011): e22315
Hailemariam, T. K. et al., Arterioscler. Thromb. Vasc. Biol 28 (2008): 1519-1526

Hamamoto, R. et al., Nat Cell Biol 6 (2004): 731-740
Hao, B. et al., Cancer Res 64 (2004): 4378-4384
Hao, X. et al., J Membr. Biol. 247 (2014): 273-279
Hays, A. et al., Pharm. Res 30 (2013): 2260-2269
He, J. Y. et al., Tumour. Biol 36 (2015): 3895-3902
He, S. et al., PLoS. One. 6 (2011): e27684
He, W. et al., J Proteome. Res 13 (2014): 2272-2281
Heese, K. et al., Eur. J Neurosci. 15 (2002): 79-86
Heubeck, B. et al., Eur. J Cancer 49 (2013): e1-e7
Hisamuddin, I. M. et al., Cancer Epidemiol. Biomarkers Prev. 14 (2005): 2366-2369
Hong, S. Y. et al., Biochem. Biophys. Res Commun. 465 (2015): 838-844
Honnorat, J. et al., Eur. J Neurosci. 11 (1999): 4226-4232
Hosogi, S. et al., Cell Physiol Biochem. 30 (2012): 1241-1253
Hsieh, Y. J. et al., Mol. Cell Biol 19 (1999): 4944-4952
Hu, R. et al., Oncol Lett. 11 (2016): 1835-1840
Hua, W. et al., Neoplasma 60 (2013): 143-150
Huang, C. et al., Cell Biol Int. 32 (2008): 1081-1090
Huang, H. et al., Int. J Clin Exp. Pathol. 8 (2015a): 11537-11542
Huang, J. et al., Am. J Physiol Gastrointest. Liver Physiol 306 (2014): G802-G810
Huang, K. T. et al., Breast Cancer Res Treat. 130 (2011): 319-329
Huang, L. et al., BMC. Cancer 15 (2015b): 13
Huang, S. L. et al., Cancers (Basel) 7 (2015): 1052-1071
Huff, L. P. et al., Genes Cancer 4 (2013): 460-475
Hummon, A. B. et al., Mol. Cancer 11 (2012): 1
Hurst, C. D. et al., Oncogene 27 (2008): 2716-2727
Hwang, M. L. et al., J Immunol. 179 (2007): 5829-5838
Iio, A. et al., Biochim. Biophys. Acta 1829 (2013): 1102-1110
Ikonomov, O. C. et al., Biochem. Biophys. Res Commun. 440 (2013): 342-347
Ilboudo, A. et al., BMC. Cancer 14 (2014): 7
Illuzzi, J. L. et al., J Mol. Neurosci. 45 (2011): 256-268
Imaoka, H. et al., Carcinogenesis 36 (2015): 346-354
Ishigami, S. et al., Anticancer Res 35 (2015): 2279-2285
Ishikawa, S. et al., J Exp. Clin Cancer Res 22 (2003): 299-306
Ito, F. et al., Int. J Gynecol. Cancer 26 (2016): 325-330
Itoh, G. et al., Cancer Sci. 104 (2013): 871-879
Jain, A. et al., Front Immunol. 5 (2014): 553
Jarvinen, T. A. et al., Cytopathology 14 (2003): 309-313
Jayarama, S. et al., J Cell Biochem. 115 (2014): 261-270
Jiang, J. et al., Oncogene 30 (2011): 4498-4508
Jiang, M. et al., Med Sci. Monit. 22 (2016): 1850-1857
Jiang, Y. Q. et al., Asian Pac. J Cancer Prev. 15 (2014): 9137-9142
Jin, Y. et al., Int. J Clin Exp. Pathol. 7 (2014): 8724-8731
Jo, Y. S. et al., Pathol. Oncol Res (2016)
Jones, M. H. et al., Genomics 63 (2000): 40-45
Joshi, N. et al., Cancer Res 66 (2006): 6851-6860
Joshi, S. et al., BMC. Cancer 15 (2015): 546
Juarez-Velazquez, R. et al., Leuk. Lymphoma 55 (2014): 2305-2311
Jung, D. J. et al., Mol. Cell Biol 22 (2002): 5203-5211
Jung, G. et al., Proc Natl Acad Sci USA 84 (1987): 4611-4615
Jung, J. K. et al., Cell Cycle 15 (2016): 584-592
Junnila, S. et al., BMC. Cancer 10 (2010): 73
Justice, J. F. et al., MBio. 6 (2015): e01863-15
Kadota, M. et al., Cancer Res 69 (2009): 7357-7365
Kaneko, N. et al., Biochem. Biophys. Res. Commun. 390 (2009): 1235-1240
Kang, C. Y. et al., J Gastrointest. Surg. 18 (2014): 7-15
Karmali, P. P. et al., PLoS. One. 6 (2011): e23840
Kasai, T. et al., Exp. Cell Res 341 (2016): 123-131
Katoh, Y. et al., Oncol Rep. 14 (2005): 1351-1355
Kawasaki, A. et al., Cell Signal. 19 (2007): 2498-2506
Khakpour, G. et al., Tumour. Biol 36 (2015): 4905-4912
Khanobdee, K. et al., Mol. Vis. 10 (2004): 933-942
Kibbe, A. H., Handbook of Pharmaceutical Excipients rd (2000)
Kim, D. J. et al., Biochem. Biophys. Res Commun. 373 (2008): 521-527
Kim, H. et al., Cell Cycle 13 (2014): 2952-2961
Kim, M. et al., Int. J Oncol 48 (2016): 2497-2507
Kim, S. K. et al., Oncogene 16 (1998): 89-93
Kim, T. W. et al., BMC. Cancer 13 (2013): 502
Kim, Y. et al., Oncol Rep. 22 (2009): 799-804
Kim, Y. R. et al., Tumori 96 (2010): 1004-1009
Kimura, J. et al., Int. J Cancer 128 (2011): 1524-1531
Kitchen, M. O. et al., Epigenetics. 11 (2016): 237-246
Krepischi, A. C. et al., Mol. Cytogenet. 9 (2016): 20
Krieg, A. M., Nat Rev. Drug Discov. 5 (2006): 471-484
Kumar, V. et al., J Hum. Genet. 56 (2011): 436-439
Kuo, C. C. et al., World J Gastroenterol. 21 (2015): 3960-3969
Landi, S. et al., Cancer Res 66 (2006): 11062-11069
Larson, Gedman A. et al., Leukemia 23 (2009): 1417-1425
Lasorsa, V. A. et al., Oncotarget. 7 (2016): 21840-21852
Lau, Y. F. et al., Mol. Carcinog 27 (2000): 308-321
Le, Jan S. et al., FEBS Lett. 580 (2006): 3395-3400
Lee, J. Y. et al., Carcinogenesis 30 (2009): 1528-1531
Lee, Y. F. et al., Biochem. Biophys. Res Commun. 323 (2004): 876-883
Leivo, I. et al., Cancer Genet. Cytogenet. 156 (2005): 104-113
Li, D. et al., Clin Cancer Res 15 (2009): 740-746
Li, L. et al., Hum. Mol. Genet. 19 (2010a): 4273-4277
Li, L. C. et al., Am. J Obstet. Gynecol. 205 (2011a): 362-25
Li, R. K. et al., J Cancer Res Clin Oncol 141 (2015a): 269-281
Li, W. et al., Curr. Cancer Drug Targets. 14 (2014): 348-356
Li, X. et al., BMC. Med Genomics 4 (2011b): 44
Li, X. et al., Int. J Biochem. Cell Biol 42 (2010b): 70-79
Li, X. et al., Mol. Cancer 14 (2015b): 95
Li, X. et al., Cancer Res (2016)
Li, Y. et al., Cell Rep. 12 (2015c): 388-395
Li, Y. et al., Mol. Cancer Res 8 (2010c): 1579-1590
Li, Z. G. et al., Leuk. Res 37 (2013): 1287-1293
Liang, Y. et al., Genes Chromosomes. Cancer 52 (2013): 305-315
Lin, F. et al., Cancer Biol Ther. 7 (2008a): 1669-1676
Lin, W. W. et al., Biochem. Pharmacol. 81 (2011): 838-847
Lin, Y. M. et al., Mol. Carcinog 47 (2008b): 925-933
Litvinov, I. V. et al., Cell Cycle 13 (2014): 2975-2982
Liu, C. et al., Nat Med. 20 (2014a): 596-598
Liu, C. C. et al., Int. J Cancer 136 (2015a): 547-559
Liu, D. et al., Int. J Oncol. 45 (2014b): 1232-1240
Liu, H. et al., BMC. Syst. Biol 5 (2011): 158
Liu, J. et al., Cell Cycle 11 (2012): 2643-2649
Liu, L. et al., Oncotarget. 6 (2015b): 2466-2482
Liu, L. X. et al., World J Gastroenterol. 9 (2003): 683-687
Liu, S. et al., Endocr. Relat Cancer 21 (2014c): R279-R300
Liu, T. et al., Mol. Med Rep. 12 (2015c): 4346-4351
Liu, T. et al., Mol. Med Rep. 10 (2014d): 169-174
Ljunggren, H. G. et al., J Exp. Med. 162 (1985): 1745-1759
Llorente, J. L. et al., Acta Otorrinolaringol. Esp. 59 (2008): 151-158
Logue, J. S. et al., J Biol Chem 286 (2011): 39269-39281

Longenecker, B. M. et al., Ann N.Y. Acad. Sci. 690 (1993): 276-291
Lonsdale, J., Nat. Genet. 45 (2013): 580-585
Lopez, J. et al., Sci. Signal. 7 (2014): e17
Lu, D. et al., Proc. Natl. Acad. Sci. U.S.A 101 (2004): 3118-3123
Lu, G. et al., Exp. Mol. Pathol. 99 (2015): 173-179
Ludwig, A. et al., Anticancer Res 22 (2002): 3213-3221
Luef, B. et al., Endocr. Relat Cancer (2016)
Lukas, T. J. et al., Proc. Natl. Acad. Sci. U.S.A 78 (1981): 2791-2795
Lundblad, R. L., Chemical Reagents for Protein Modification 3rd (2004)
Ma, J. et al., Tumour. Biol 35 (2014a): 8439-8443
Ma, R. C. et al., Diabetes Res Clin Pract. 103 (2014b): 328-337
Ma, W. J. et al., Med Oncol 31 (2014c): 768
Mabuchi, H. et al., Cancer Res 61 (2001): 2870-2877
Maiso, P. et al., Cancer Res 75 (2015): 2071-2082
Mao, Y. et al., BMC. Cancer 13 (2013): 498
Mao, Y. et al., Tumour. Biol (2016)
Marchio, C. et al., J Clin Pathol. 63 (2010): 220-228
Marcinkiewicz, K. M. et al., Exp. Cell Res 320 (2014): 128-143
Marhold, M. et al., Mol. Cancer Res 13 (2015): 556-564
Markt, S. C. et al., Cancer Causes Control 26 (2015): 25-33
Masuda, H. et al., Mol. Biol Cell 24 (2013): 2894-2906
Masuda, H. et al., Mol. Biol Cell 27 (2016): 1753-1763
Matsushita, R. et al., Br. J Cancer 113 (2015): 282-289
Mazzoccoli, G. et al., Chronobiol. Int. 28 (2011): 841-851
McAvoy, S. et al., Cytogenet. Genome Res 118 (2007): 260-269
McDonald, J. D. et al., Genomics 23 (1994): 229-232
Mehraj, V. et al., FEMS Immunol. Med Microbiol. 64 (2012): 98-100
Melaiu, O. et al., Mutat. Res 750 (2012): 132-140
Melle, C. et al., J Proteome. Res 6 (2007): 306-315
Mereniuk, T. R. et al., Mol. Cancer Ther. 12 (2013): 2135-2144
Mereniuk, T. R. et al., Cancer Res 72 (2012): 5934-5944
Messai, Y. et al., Cancer Res 74 (2014): 6820-6832
Meziere, C. et al., J Immunol 159 (1997): 3230-3237
Milani, C. et al., BMC. Cancer 13 (2013): 119
Mistry, H. et al., Mol. Cancer Ther. 12 (2013): 2651-2662
Miyaji, K. et al., J Viral Hepat. 10 (2003): 241-248
Mohelnikova-Duchonova, B. et al., Pancreas 42 (2013): 707-716
Monni, O. et al., Proc. Natl. Acad. Sci. U.S.A 98 (2001): 5711-5716
Moon, J. W. et al., J Exp. Clin Cancer Res. 33 (2014): 4
Moreira, Sousa C. et al., EMBO Mol. Med 5 (2013): 309-325
Morgan, R. A. et al., Science 314 (2006): 126-129
Mori, M. et al., Transplantation 64 (1997): 1017-1027
Morito, N. et al., Cancer Res 66 (2006): 812-819
Mortara, L. et al., Clin Cancer Res. 12 (2006): 3435-3443
Mourskaia, A. A. et al., Breast Cancer Res 14 (2012): R149
Moyer, B. D. et al., PLoS. One. 4 (2009): e7682
Mueller, L. N. et al., J Proteome. Res 7 (2008): 51-61
Mueller, L. N. et al., Proteomics. 7 (2007): 3470-3480
Mujica, A. O. et al., FEBS J 272 (2005): 4884-4898
Mumberg, D. et al., Proc. Natl. Acad. Sci. U.S.A 96 (1999): 8633-8638
Muvarak, N. et al., Mol. Cancer Res 13 (2015): 699-712
Nagai, H. et al., Cancer Lett. 193 (2003): 41-47
Nagoshi, H. et al., Cancer Res 72 (2012): 4954-4962
Nakada, S. et al., EMBO Rep. 9 (2008): 1019-1026
Nakagawa, Y. et al., Br. J Cancer 80 (1999): 914-917
Narayan, G. et al., Mol. Cancer 5 (2006): 16
National Cancer Institute (NCI), (19-1-2011), www.cancer.gov/cancertopics/wyntk/kidney/page3
Nayak, D. et al., Oncotarget. 6 (2015): 34342-34357
Nie, W. et al., Oncotarget. 6 (2015): 3003-3012
Nikolaev, A. Y. et al., Cell 112 (2003): 29-40
Niu, N. et al., BMC. Cancer 12 (2012): 422
Nobusawa, S. et al., Brain Tumor Pathol. 31 (2014): 229-233
O'Neal, J. et al., Exp. Hematol. 37 (2009): 234-244
Oh, Y. et al., J Biol. Chem 287 (2012): 17517-17529
Okayama, H. et al., Cancer Epidemiol. Biomarkers Prev. 23 (2014): 2884-2894
Okunade, G. W. et al., J Biol Chem 282 (2007): 26517-26527
Ooe, A. et al., Breast Cancer Res Treat. 101 (2007): 305-315
Ortega, P. et al., Int. J Oncol 36 (2010): 1209-1215
Palma, G. et al., Biochim. Biophys. Acta 1826 (2012): 407-414
Pandey, R. N. et al., Oncogene 29 (2010): 3715-3722
Park, J. et al., Cancer Res 62 (2002): 1284-1288
Park, T. J. et al., Nat Genet. 38 (2006): 303-311
Parker, H. et al., Leukemia 25 (2011): 489-497
Pattabiraman, D. R. et al., Leukemia 27 (2013): 269-277
Pavon, M. A. et al., Head Neck 38 Suppl 1 (2016): E1392-E1403
Payton, M. et al., Oncogene 21 (2002): 8529-8534
Pei, X. H. et al., Cancer Res 71 (2011): 2969-2977
Peifer, M. et al., Nat Genet. 44 (2012): 1104-1110
Pereira, B. et al., Nucleic Acids Res 41 (2013): 3986-3999
Petrenko, A. A. et al., Biochemistry (Mosc.) 71 (2006): 1153-1160
Piepoli, A. et al., Exp. Biol Med. (Maywood.) 237 (2012): 1123-1128
Pinheiro, J. et al., nlme: Linear and Nonlinear Mixed Effects Models (CRAN.R-project.org/packe=nlme) (2015)
Piskacek, M. et al., J Cell Mol. Med 13 (2009): 693-700
Plebanski, M. et al., Eur. J Immunol 25 (1995): 1783-1787
Pliarchopoulou, K. et al., Cancer Chemother. Pharmacol. 71 (2013): 245-255
Porta, C. et al., Virology 202 (1994): 949-955
Potocnik, U. et al., Genes Chromosomes. Cancer 36 (2003): 48-56
Prasad, A. et al., J Biol Chem 283 (2008): 26624-26633
Pritchard, K. I. et al., J Clin Oncol 26 (2008): 736-744
Puente, X. S. et al., Nature 526 (2015): 519-524
Qi, C. et al., Lab Invest 94 (2014): 766-776
Qin, L. et al., Cancer Res 71 (2011): 1742-1751
Qin, L. et al., Cancer Res 74 (2014): 3477-3488
Qiu, X. et al., Oncotarget. 6 (2015): 15397-15409
Rad, E. et al., Mol. Cancer Res 13 (2015): 1149-1160
Rahme, G. J. et al., Cancer Res 76 (2016): 2964-2976
Rainer, J. et al., Mol. Endocrinol. 26 (2012): 178-193
Rajaraman, P. et al., Cancer Epidemiol. Biomarkers Prev. 18 (2009): 1651-1658
Rammensee, H. et al., Immunogenetics 50 (1999): 213-219
Ramsay, R. G. et al., Expert. Opin. Ther. Targets. 7 (2003): 235-248
Rauch, T. A. et al., Tumour. Biol 33 (2012): 287-296
RefSeq, The NCBI handbook [Internet], Chapter 18, (2002), www.ncbi.nlm.nih.gov/books/NBK21091/
Ren, X. L. et al., J Cancer Res Clin Oncol 142 (2016): 581-592
Rhee, I. et al., Nature 416 (2002): 552-556
Riches, J. C. et al., Blood 123 (2014): 4101-4110
Rini, B. I. et al., Cancer 107 (2006): 67-74
Robin, T. P. et al., Mol. Cancer Res 10 (2012): 1098-1108

Rochat, B. et al., Biopharm. Drug Dispos. 29 (2008): 103-118
Rock, K. L. et al., Science 249 (1990): 918-921
Rodenko, B. et al., Nat Protoc. 1 (2006): 1120-1132
Rodins, K. et al., Clin Cancer Res 8 (2002): 1075-1081
Rozenblum, E. et al., Hum. Genet. 110 (2002): 111-121
Ryu, S. D. et al., Life Sci. 75 (2004): 2559-2572
S3-Leitlinie Lungenkarzinom, 020/007, (2011)
Sadasivam, S. et al., Genes Dev. 26 (2012): 474-489
Sadeque, A. et al., BMC. Med. Genomics 5 (2012): 59
Saiki, R. K. et al., Science 239 (1988): 487-491
Sainz, J. et al., J Clin Endocrinol. Metab 97 (2012): E845-E851
Saito, Y. et al., Int. J Cancer 105 (2003): 527-532
Salon, C. et al., J Pathol. 213 (2007): 303-310
Samaei, N. M. et al., J Biomed. Sci. 21 (2014): 73
Sanders, S. et al., Cytogenet. Cell Genet. 88 (2000): 324-325
Sanghani, S. P. et al., Clin Cancer Res 9 (2003): 4983-4991
Sankaranarayanan, P. et al., PLoS. One. 10 (2015): e0121396
Schaefer-Klein, J. L. et al., PLoS. One. 10 (2015): e0142327
Schepeler, T. et al., Oncogene 31 (2012): 2750-2760
Schioth, H. B. et al., Mol. Aspects Med 34 (2013): 571-585
Seeger, F. H. et al., Immunogenetics 49 (1999): 571-576
Selcuklu, S. D. et al., J Biol Chem 287 (2012): 29516-29528
Sellick, G. S. et al., Blood 111 (2008): 1625-1633
Sethi, S. et al., Diagn. Mol. Pathol. 18 (2009): 81-87
Shamma, A. et al., Mol. Cell Biol 33 (2013): 3113-3124
Shang, S. et al., Zhonghua Wei Chang Wal Ke. Za Zhi. 18 (2015): 277-281
Shen, L. et al., Proc. Natl. Acad. Sci. U.S.A 112 (2015): 5425-5430
Sherman, F. et al., Laboratory Course Manual for Methods in Yeast Genetics (1986)
Sherman, S. K. et al., Surgery 154 (2013): 1206-1213
Sherman-Baust, C. A. et al., Cancer Cell 3 (2003): 377-386
Shi, R. et al., Oncol Rep. 30 (2013): 1883-1889
Sieuwerts, A. M. et al., Clin Cancer Res 12 (2006): 3319-3328
Singh-Jasuja, H. et al., Cancer Immunol. Immunother. 53 (2004): 187-195
Skarie, J. M. et al., Hum. Mol. Genet. 17 (2008): 2474-2485
Small, E. J. et al., J Clin Oncol. 24 (2006): 3089-3094
Smith, M. J. et al., Br. J Cancer 100 (2009): 1452-1464
Sonderstrup, I. M. et al., Mol. Oncol 9 (2015): 1207-1217
Song, J. et al., Mol. Cancer Res 13 (2015): 969-981
Standiford, T. J. et al., Oncogene 30 (2011): 2475-2484
Stary, S. et al., Genes Chromosomes. Cancer 52 (2013): 33-43
Stenman, G. et al., Cell Cycle 9 (2010): 2986-2995
Stevison, F. et al., Adv. Pharmacol. 74 (2015): 373-412
Strittmatter, L. et al., Hum. Mol. Genet. 23 (2014): 2313-2323
Sturm, M. et al., BMC. Bioinformatics. 9 (2008): 163
Su, K. C. et al., Dev. Cell 21 (2011): 1104-1115
Su, X. Y. et al., Genes Chromosomes. Cancer 41 (2004): 243-249
Subramanian, M. et al., J Clin Endocrinol. Metab 94 (2009): 1467-1471
Suh, H. W. et al., Biochem. Biophys. Res Commun. 438 (2013): 264-269
Tafesse, F. G. et al., J Biol Chem 282 (2007): 17537-17547
Takeda, H. et al., Nat Genet. 47 (2015): 142-150
Takeda, Y. et al., Glycobiology 24 (2014): 344-350
Talebian, Yazdi M. et al., Oncotarget. 7 (2016): 3477-3488
Tan, Z. et al., J Proteome. Res 13 (2014): 2783-2795
Teufel, R. et al., Cell Mol Life Sci. 62 (2005): 1755-1762
Tews, B. et al., Oncogene 26 (2007): 5010-5016
Thion, M. S. et al., J Natl. Cancer Inst. 107 (2015)
Thion, M. S. et al., Eur. J Hum. Genet. (2016)
Thompson, P. et al., Cancer Chemother. Pharmacol. 74 (2014): 831-838
Thorsen, K. et al., Mol Cell Proteomics. 7 (2008): 1214-1224
Tian, M. et al., Int. J Clin Exp. Pathol. 8 (2015): 3892-3900
Tillement, V. et al., Mol. Cancer 8 (2009): 10
Tong, D. L. et al., PLoS. One. 9 (2014): e102483
Tran, T. T. et al., Photochem. Photobiol. 90 (2014): 1136-1143
Tripodi, D. et al., BMC. Med. Genomics 2 (2009): 65
Tsujimoto, Y. et al., Clin Cancer Res 10 (2004): 3007-3012
Tsukamoto, N. et al., Clin Cancer Res 15 (2009): 5733-5743
Turner, A. et al., PLoS. One. 8 (2013): e56817
Uchikado, Y. et al., Int. J Oncol 29 (2006): 1337-1347
Vadlapudi, A. D. et al., Int. J Pharm. 441 (2013): 535-543
Valeri, A. et al., Clin Transl. Oncol 13 (2011): 215-221
Valle, C. W. et al., PLoS. One. 6 (2011): e29073
Van, Vlierberghe P. et al., Leukemia 22 (2008): 762-770
Vandermoere, F. et al., J Biol Chem 281 (2006): 14307-14313
Vendrell, J. A. et al., J Mol. Endocrinol. 32 (2004): 397-414
Villacis, R. A. et al., Int. J Cancer 138 (2016): 1928-1935
Wallrapp, C. et al., Ann. Oncol 10 Suppl 4 (1999): 64-68
Walport, L. J. et al., J Biol Chem 289 (2014): 18302-18313
Walter, S. et al., J Immunol 171 (2003): 4974-4978
Walter, S. et al., Nat Med. 18 (2012): 1254-1261
Wang, G. et al., World J Gastroenterol. 21 (2015a): 3983-3993
Wang, P. et al., Acta Biochim. Biophys. Sin. (Shanghai) 47 (2015b): 214-223
Wang, R. T. et al., Exp. Ther. Med 6 (2013a): 1054-1058
Wang, S. M. et al., Clin Cancer Res 17 (2011): 6040-6051
Wang, V. W. et al., Head Neck 35 (2013b): 831-835
Wang, Y. et al., Dev. Cell 34 (2015c): 475-483
Wang, Y. et al., Mol. Cancer Res 11 (2013c): 1624-1635
Wang, Y. et al., Mol. Cell 49 (2013d): 997-1009
Wang, Z. et al., Cancer Res 64 (2004): 2998-3001
Wei, J. L. et al., Tumour. Biol 35 (2014): 9185-9194
Wei, Y. P. et al., Xi. Bao. Yu Fen. Zi. Mian. Yi. Xue. Za Zhi. 28 (2012): 354-357
Weitzdoerfer, R. et al., J Neural Transm. Suppl (2001): 95-107
Weng, S. et al., Cancer Epidemiol. Biomarkers Prev. 21 (2012): 1336-1343
Wharton, S. B. et al., Neuropathol. Appl. Neurobiol. 27 (2001): 305-313
Wheeler, H. E. et al., PLoS. Genet. 5 (2009): e1000685
Whitworth, H. et al., PLoS. One. 7 (2012): e38950
Willcox, B. E. et al., Protein Sci. 8 (1999): 2418-2423
Williams, D. S. et al., PLoS. One. 5 (2010): e16012
Williams, S. et al., PLoS. One. 8 (2013): e74589
Williams, S. A. et al., Cell 146 (2011): 918-930
Wilting, S. M. et al., Genes Chromosomes. Cancer 47 (2008): 890-905
Winter, A. G. et al., Proc. Natl. Acad. Sci. U.S.A 97 (2000): 12619-12624
Wlcek, K. et al., Cancer Biol Ther. 11 (2011): 801-811
Woenckhaus, M. et al., J Pathol. 210 (2006): 192-204
Wong, K. et al., Curr. Opin. Genet. Dev. 12 (2002): 583-591
Wong, N. C. et al., Epigenetics. 7 (2012): 535-541
Wong, S. C. et al., PLoS. One. 8 (2013): e79481
Wong, Y. F. et al., Oncogene 26 (2007): 1971-1982
Wrighton, K. H., Nat Rev Cancer 11 (2011): 757
Wu, G. et al., Cancer Res 67 (2007): 4123-4129

Wu, L. et al., Clin Cancer Res 16 (2010): 3760-3768
Wu, W. et al., Nature 400 (1999): 331-336
Wu, X. et al., Transgenic Res 21 (2012): 1109-1115
Wu, Z. et al., Neoplasia. 11 (2009): 66-76
Xie, X. et al., Oncol Lett. 7 (2014): 1537-1543
Xu, H. et al., Zhongguo Fei. Ai. Za Zhi. 13 (2010): 856-860
Xu, J. et al., Psychiatry Res 220 (2014a): 1131-1137
Xu, J. et al., Biochem. Biophys. Res Commun. 460 (2015): 409-415
Xu, J. et al., Genet. Mol. Res 13 (2014b): 5732-5744
Yamamoto, S. et al., Clin Cancer Res 10 (2004): 651-657
Yamamoto, S. et al., J Clin Oncol 21 (2003): 447-452
Yanagiya, A. et al., Mol. Cell 46 (2012): 847-858
Yang, C. et al., Virchows Arch. 463 (2013): 379-390
Yang, J. et al., Surg. Oncol 22 (2013): e53-e57
Yang, M. et al., Ups. J Med Sci. 115 (2010): 232-237
Yang, S. et al., Biochim. Biophys. Acta 1772 (2007): 1033-1040
Yang, T. et al., Gut 65 (2016): 124-133
Yao, X. et al., PLoS. One. 9 (2014): e101564
Yeh, P. Y. et al., J Biol Chem 279 (2004): 26143-26148
Yokota, T. et al., Acta Neuropathol. 111 (2006): 29-38
Yoshida, K. et al., Cancer Sci. 104 (2013): 171-177
Yu, H. et al., Nat Chem Biol 11 (2015a): 847-854
Yu, J. et al., Gut 64 (2015b): 636-645
Yu, Y. Y. et al., Zhonghua Zhong. Liu Za Zhi. 28 (2006): 84-87
Yuan, J. Y. et al., Oncol Lett. 1 (2010): 649-655
Yuan, M. et al., Int. J Oncol (2016)
Zaremba, S. et al., Cancer Res. 57 (1997): 4570-4577
Zeng, H. et al., Dev. Biol 339 (2010): 418-428
Zeng, Y. et al., Cancer Sci. 106 (2015): 1385-1393
Zhai, W. et al., Eur. Rev Med. Pharmacol. Sci. 18 (2014): 1354-1360
Zhang, A. et al., J Biol Chem 289 (2014): 29180-29194
Zhang, J. et al., Oncotarget. 6 (2015a): 42040-42052
Zhang, L. et al., Lung Cancer 89 (2015b): 320-328
Zhang, Q. Q. et al., Oncotarget. 6 (2015c): 3123-3135
Zhang, W. et al., Mol. Med Rep. 12 (2015d): 141-146
Zhang, W. et al., Tumour. Biol 37 (2016): 7741-7748
Zhang, W. et al., Int. J Mol. Sci. 12 (2011): 5672-5683
Zhang, X. et al., J Cell Sci. 122 (2009): 2240-2251
Zhang, Y. et al., Gene 497 (2012): 93-97
Zhang, Y. et al., Biochem. Biophys. Res Commun. 463 (2015e): 1144-1151
Zhao, H. et al., Gene 548 (2014a): 234-243
Zhao, W. et al., Tumour. Biol 35 (2014b): 5259-5266
Zheng, D. et al., Zhonghua Gan Zang. Bing. Za Zhi. 17 (2009): 198-202
Zheng, J. et al., DNA Cell Biol 33 (2014a): 847-853
Zheng, X. F. et al., Hepatogastroenterology 61 (2014b): 880-884
Zheng, Y. et al., Clin Biochem. 44 (2011): 1405-1411
Zhou, H. et al., EMBO J 32 (2013a): 583-596
Zhou, J. et al., Mitochondrion. 13 (2013): 163-169
Zhou, J. et al., Mol. Biol Rep. 40 (2013b): 5759-5767
Zhou, J. et al., Int. J Mol. Med 32 (2013c): 653-660
Zhou, J. et al., Asian Pac. J Cancer Prev. 15 (2014a): 2439-2445
Zhou, J. et al., Int. J Biochem. Cell Biol 43 (2011): 1668-1673
Zhou, X. et al., Cell Physiol Biochem. 33 (2014b): 1003-1012
Zhou, X. et al., Oncotarget. 5 (2014c): 11631-11640
Zhou, Y. et al., Front Biosci. (Landmark. Ed) 16 (2011): 1109-1131
Zhu, H. et al., J Cell Sci. 122 (2009): 2750-2759
Zhu, Q. et al., Int. J Clin Exp. Pathol. 8 (2015): 9175-9181
Zhu, X. L. et al., Nan. Fang Yi. Ke. Da. Xue. Xue. Bao. 28 (2008): 1775-1778
Zhu, Z. Q. et al., Metabolism 63 (2014): 120-126
Zohrabian, V. M. et al., Oncol Rep. 18 (2007): 321-328
Zolk, O. et al., Am. J Pathol. 182 (2013): 234-243

The invention claimed is:

1. A method of eliciting an immune response in a patient who has cancer, comprising administering to said patient a population of activated T cells that selectively recognize cells that aberrantly present a peptide consisting of the amino acid sequence of SEQ ID NO: 1, 2, 3, 4, 5, 6, 7, 8, 9, or 10, wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell, wherein said cancer is selected from the group consisting of lung cancer, melanoma, liver cancer, breast cancer, uterine cancer, Merkel cell carcinoma, pancreatic cancer, gallbladder cancer, bile duct cancer, colon or rectum cancer, urinary bladder cancer, kidney cancer, leukemia, ovarian cancer, esophageal cancer, brain cancer, gastric cancer, and prostate cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the population of activated T cells are administered in the form of a composition.

7. The method of claim 6, wherein the composition further comprises an adjuvant.

8. The method of claim 7, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The method of claim 1, wherein the contacting is in vitro.

10. A method of eliciting an immune response in a patient who has lung cancer, comprising administering to said patient a population of activated T cells that selectively recognize cells that aberrantly present a peptide consisting of the amino acid sequence of SEQ ID NO: 1, 2, 3, 4, 5, 6, 7, 8, 9, or 10,
wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell.

11. The method of claim 1, wherein the cancer is lung cancer.

12. The method of claim 1, wherein the cancer is breast cancer.

13. The method of claim 1, wherein the cancer is colon or rectum cancer.

14. The method of claim 1, wherein the activated T cells release a cytokine.

15. The method of claim 1, wherein the immune response is capable of killing cancer cells that present a peptide consisting of the amino acid sequence of SEQ ID NO: 1, 2, 3, 4, 5, 6, 7, 8, 9, or 10.

16. A method of eliciting an immune response in a patient who has lung cancer, melanoma, liver cancer, breast cancer, uterine cancer, Merkel cell carcinoma, pancreatic cancer, gallbladder cancer, bile duct cancer, colon or rectum cancer, urinary bladder cancer, kidney cancer, leukemia, ovarian cancer, esophageal cancer, brain cancer, gastric cancer, or prostate cancer, comprising administering to said patient a composition comprising a peptide in the form of a pharmaceutically acceptable salt and an adjuvant, wherein said peptide consists of the amino acid sequence of SEQ ID NO: 1, 2, 3, 4, 5, 6, 7, 8, 9, or 10, thereby inducing a T-cell response to the lung cancer, melanoma, liver cancer, breast cancer, uterine cancer, Merkel cell carcinoma, pancreatic cancer, gallbladder cancer, bile duct cancer, colon or rectum cancer, urinary bladder cancer, kidney cancer, leukemia, ovarian cancer, esophageal cancer, brain cancer, gastric cancer, or prostate cancer.

17. The method of claim 16, wherein the T cell response is a cytotoxic T cell response.

18. The method of claim 16, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

19. The method of claim 16, wherein the immune response is capable of killing cancer cells that present a peptide consisting of the amino acid sequence of SEQ ID NO: 1, 2, 3, 4, 5, 6, 7, 8, 9, or 10.

20. The method of claim 7, wherein the adjuvant comprises IL-21.

21. The method of claim 1, wherein the peptide consists of the amino acid sequence of SEQ ID NO: 1.

22. The method of claim 1, wherein the peptide consists of the amino acid sequence of SEQ ID NO: 2.

23. The method of claim 1, wherein the peptide consists of the amino acid sequence of SEQ ID NO: 3.

24. The method of claim 1, wherein the peptide consists of the amino acid sequence of SEQ ID NO: 4.

25. The method of claim 1, wherein the peptide consists of the amino acid sequence of SEQ ID NO: 5.

26. The method of claim 1, wherein the peptide consists of the amino acid sequence of SEQ ID NO: 6.

27. The method of claim 1, wherein the peptide consists of the amino acid sequence of SEQ ID NO: 7.

28. The method of claim 1, wherein the peptide consists of the amino acid sequence of SEQ ID NO: 8.

29. The method of claim 1, wherein the peptide consists of the amino acid sequence of SEQ ID NO: 9.

30. The method of claim 1, wherein the peptide consists of the amino acid sequence of SEQ ID NO: 10.

* * * * *